(12) United States Patent
Laufer et al.

(10) Patent No.: US 8,633,312 B2
(45) Date of Patent: Jan. 21, 2014

(54) DIBENZOCYCLOHEPTATONE DERIVATIVES AND PHARMACEUTICAL AGENTS CONTAINING SAID COMPOUNDS

(75) Inventors: Stefan Laufer, Tubingen (DE); Wolfgang Albrecht, Ulm (DE)

(73) Assignee: c-a-i-r biosciences GmbH, Tubingen (DE)

( * ) Notice: Subject to any disclaimer, the term of this patent is extended or adjusted under 35 U.S.C. 154(b) by 0 days.

(21) Appl. No.: 13/122,883

(22) PCT Filed: Oct. 9, 2009

(86) PCT No.: PCT/EP2009/063215
§ 371 (c)(1),
(2), (4) Date: Dec. 1, 2011

(87) PCT Pub. No.: WO2010/040843
PCT Pub. Date: Apr. 15, 2010

(65) Prior Publication Data
US 2012/0115862 A1 May 10, 2012

(30) Foreign Application Priority Data
Oct. 9, 2008 (EP) .................. 08166223

(51) Int. Cl.
C07D 295/03 (2006.01)
A61K 31/5375 (2006.01)

(52) U.S. Cl.
USPC .......................... 544/106; 514/185

(58) Field of Classification Search
USPC .......................... 544/106; 514/185
See application file for complete search history.

(56) References Cited

U.S. PATENT DOCUMENTS

| | | | |
|---|---|---|---|
| 3,780,061 A | 12/1973 | Allais et al. | |
| 4,576,960 A | 3/1986 | Martin et al. | |
| 5,591,752 A * | 1/1997 | Kimura et al. | 514/314 |
| 2009/0105327 A1 | 4/2009 | Laufer et al. | |

FOREIGN PATENT DOCUMENTS

| | | |
|---|---|---|
| CA | 2175287 | 10/1997 |
| DE | 2 224 655 A | 12/1972 |
| WO | WO 98/32730 A1 | 7/1998 |
| WO | WO 01/05744 A1 | 1/2001 |
| WO | WO 01/05745 A1 | 1/2001 |
| WO | WO 01/05746 A1 | 1/2001 |
| WO | WO 01/05749 A1 | 1/2001 |
| WO | WO 01/05751 A1 | 1/2001 |
| WO | WO 01/42189 A1 | 6/2001 |
| WO | WO 02/45752 A2 | 6/2002 |
| WO | WO 02/076447 A1 | 10/2002 |
| WO | WO 03/018535 A2 | 3/2003 |
| WO | WO 2006/120010 A2 | 11/2006 |

OTHER PUBLICATIONS

Database CA [Online]; "6,11-Dihydro-11-oxodibenz[b, e]oxepin derivatives", Database Accession No. 1981:174914, 2 pages.
Database [Online]; Nishizawa et al.; "Preparation of 6,11-dihdrodibenz[b, e]oxepin-11-ones", Database Accession No. 1997:702036, 1 page.
Database CA [Online], "Dibenzoxepin derivative", Database Accession No. 1994:192172, 1 page.
Donat et al., "In-Vitro Screening Assay to Evaluate Cytokine Release Inhibitors", *Arch. Pharm. Pharm. Med. Chem. 333*, Suppl. 1, 1-40, 2000.
Engelhardt et al., "Structure-Activity Relationships in the Cyproheptadine Series", *J. Med. Chem.* vol. 8, pp. 829-835, 1965.
Kluge et al., "Tricyclic Aryl-Substituted Anticoccidial Azauracils", *J. Med. Chem.* vol. 21, No. 6, pp. 529-536, 1978.
Leeson et al., "Transannular Cyclizations of 5-(Hydroxy-amino)dibenzo[a,e] cyclooctatrienes. Regioselective Synthesis of Dibenzohomotropane Analogues", *J. Org. Chem.* vol. 55(7), pp. 2094-2103, 1990.
Ottosen et al., "Synthesis and Structure—Activity Relationship of Aminobenzophenones. A Novel Class of p38 MAP Kinase Inhibitors with High Antiinflammatory Activity", *J. Med. Chem.* vol. 46, pp. 5651-5662, 2003.
Pavia et al., "Structure—Activity Studies on Benzhydrol-Containing Nipecotic Acid and Guvacine Derivatives as Potent, Orally-Active Inhibitors of GABA Uptake", *J. Med. Chem.* vol. 35, pp. 4238-4248, 1992.
Revesz et al., "SAR of benzoylpyridines and benzophenones as p38α MAP kinase inhibitors with oral activity", *Bioorganic & Medicinal Chemistry Letters 14*, pp. 3601-3605, 2004.

* cited by examiner

*Primary Examiner* — Yong Chu
*Assistant Examiner* — Sonya Wright
(74) *Attorney, Agent, or Firm* — Viksnins Harris & Padys PLLP

(57) ABSTRACT

The present invention relates to compounds of the formula I

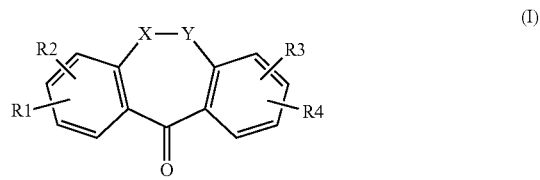

(I)

wherein R1, R2, R3, R4, X and Y have the meanings given in the description. The compounds have an action which is immunomodulating and inhibits or regulates the release of IL-1β and/or TNF-α. They can therefore be used for treatment of diseases connected with a disturbance in the immune system.

15 Claims, No Drawings

DIBENZOCYCLOHEPTATONE DERIVATIVES AND PHARMACEUTICAL AGENTS CONTAINING SAID COMPOUNDS

The present invention relates to compounds of the formula I

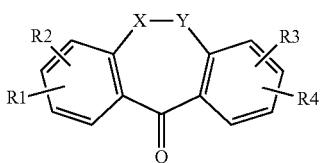

wherein X, Y and R1 to R4 have the meanings given below, and pharmaceutical compositions which contain the compounds of the formula I. The compounds are interleukin-1β (IL-1β) and tumor necrosis factor α (TNF-α) inhibitors which can be used for treatment of inflammatory diseases.

IL-1β and TNF-α protect the body against infectious agents, tumors or tissue damage. In the case of autoimmune diseases, however, an increased production of IL-1β and TNF-α occurs, which can result, for example, in the degeneration of bone and cartilage. Drugs which regulate the release of IL-β and TNF-α can therefore be used for treatment of inflammatory diseases.

One group of compounds which inhibit the release of IL-1β and TNF-α are known from WO 98/32730. They correspond to the general formula

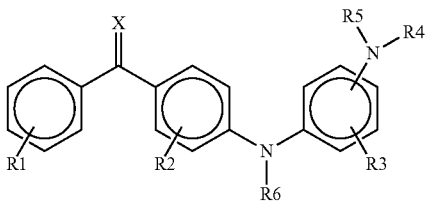

and can be used for treatment and prophylaxis of asthma, allergies, rheumatoid arthritis, spondyloarthritis, gout, atherosclerosis, chronic inflammatory bowel disease, proliferative and inflammatory skin diseases, such as psoriasis and atopic dermatitis.

Further compounds of this group are described in WO 01/05744, WO 01/05745, WO 01/05746, WO 01/05749, WO 01/05751, WO 01/42189, WO 02/45752, WO 02/076447 and WO 03/018535 and in J. Med. Chem. 2003, 46, 5651-5662 and Bioorganic & Medicinal Chemistry Letters 14 (2004) 3601-3605.

WO 2006/120010 describes dibenzocycloheptanone derivatives of the formula I

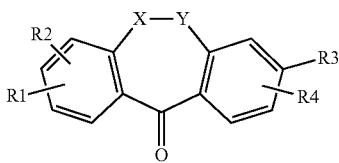

wherein one of the ring atoms X and Y represents CH$_2$ and the other represents O, S, SO, SO$_2$ or NR5; or —X—Y— represents —CH$_2$—CH$_2$— or —CH=CH—; R1 represents H or C$_1$-C$_6$-alkyl; and R2 represents H, halogen or C$_1$-C$_4$-alkyl-C≡C—, which is optionally substituted by an amino group. R3 represents halogen or an optionally substituted amino radical. The compounds are interleukin-1β (IL-1β) and tumor necrosis factor α (TNF-α) inhibitors which can be used for treatment of inflammatory diseases.

However, the action of the compounds is not satisfactory.

The present invention is therefore based on the object of providing compounds which have an anti-inflammatory action and have an improved action.

This object is achieved by the compounds of the formula I. The invention thus relates to compounds of the formula I

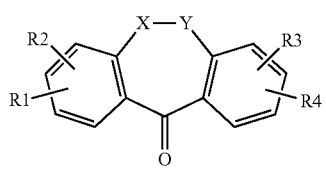

wherein
R1 is chosen from
A) RO—, wherein R is chosen from:
  a) C$_1$-C$_6$-alkyl, which is substituted by 1, 2 or 3 hydroxyl or C$_1$-C$_6$-alkoxy groups;
  b) C$_1$-C$_6$-alkyl, which is substituted by a saturated or unsaturated, aromatic or non-aromatic heterocyclic radical having 5 or 6 ring atoms, which contains 1, 2 or 3 hetero atoms which are chosen independently of each other from O, N and S, wherein the heterocyclic radical can optionally contain 1 or 2 hydroxy, C$_1$-C$_6$-alkoxy or C$_1$-C$_6$-alkyl substituents and can be condensed with a phenyl ring or a saturated or unsaturated carbocyclic radical having 5 or 6 ring atoms;
  c) a non-aromatic heterocyclic radical having 5 or 6 ring atoms, which contains 1 or 2 hetero atoms which are chosen independently of each other from O and N;
  d) C$_1$-C$_6$-alkyl;
  e) H;
  f) C$_1$-C$_6$-alkyl, which is substituted by NR6R7;
  g) CF$_3$SO$_2$—;
  h) C$_1$-C$_6$-alkylcarbonyloxy-C$_1$-C$_6$-alkyl; and
  i) (C3-C7-cycloalkyl)-C$_1$-C$_6$-alkyl, which can optionally contain 1 or 2 hydroxy, C$_1$-C$_6$-alkoxy or C$_1$-C$_6$-alkyl substituents on the cycloalkyl radical;
B) NR6R7;
C) tetrazolo; and
D) NR8CONR13R14;
R2 represents H or C$_1$-C$_6$-alkyl;
R3 is chosen from:

a)

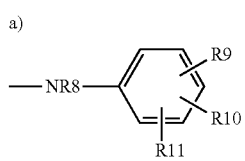

b)

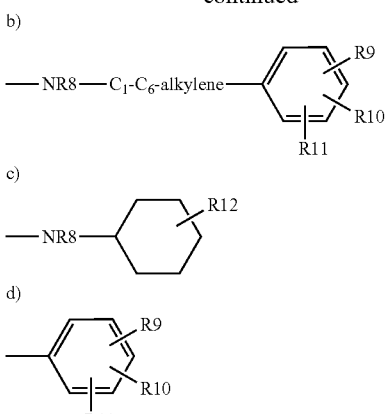

c)

—NR8—[cyclohexyl-R12]

d)

[phenyl with R9, R10, R11]

e) —NH—$C_1$-$C_6$-alkylene-NR6R7
f) tetrazolo;

R4 represents H, halogen or $C_1$-$C_6$-alkyl;

R5 represents H or $C_1$-$C_6$-alkyl, which is substituted by 1, 2 or 3 hydroxyl or $C_1$-$C_6$-alkoxy groups;

R6 and R7, which can be identical or different, represent H or $C_1$-$C_6$-alkyl, which is substituted by 1, 2 or 3 hydroxyl or $C_1$-$C_6$-alkoxy groups;

R8 represents H or $C_1$-$C_6$-alkyl;

R9, R10 and R11, which can be identical or different, are chosen from:
 a) H,
 b) $NH_2$,
 c) mono-$C_1$-$C_6$-alkylamino,
 d) di-$C_1$-$C_6$-alkylamino,
 e) $C_1$-$C_6$-alkyl,
 f) $C_1$-$C_6$-alkoxy,
 g) hydroxyl,
 h) halogen,
 i) $C_1$-$C_6$-alkyl, which is substituted by 1, 2 or 3 halogen atoms;
 j) CONR6R7; and
 k) $NO_2$;

R12 represents H or $NH_2$;

R13 and R14, which can be identical or different, represent H or $C_1$-$C_6$-alkyl, or together with the nitrogen atom to which they are bonded form a non-aromatic heterocyclic radical having 5 or 6 ring atoms, which contains 1 or 2 hetero atoms which are chosen independently of each other from O and N; and the optical isomers, physiologically acceptable salts and solvates thereof.

The expression "alkyl" (also in combination with other groups, such as alkoxy, haloalkyl etc.) includes straight-chain and branched alkyl groups having preferably 1 to 6 or 1 to 4 carbon atoms, such as methyl, ethyl, n- and i-propyl, n-, i- and t-butyl, sec-butyl, n-pentyl and n-hexyl.

The expression "halogen" stands for a fluorine, chlorine, bromine or iodine atom, in particular for a fluorine or chlorine atom.

$C_1$-$C_6$-Alkoxy which is substituted by 1, 2 or 3 hydroxyl or $C_1$-$C_6$-alkoxy groups is preferably $C_2$-$C_6$-alkoxy, in particular 2-hydroxyethoxy, 3-hydroxypropoxy, 2-hydroxypropoxy, 1,2-dihydroxyethoxy, 2,3-dihydroxypropoxy or 2,3-dimethoxypropoxy.

A saturated non-aromatic heterocyclic radical is, in particular, pyrrolidinyl, piperidinyl, hydroxypiperidinyl, piperazinyl, tetrahydropyranyl, tetrahydrofuranyl, dioxolanyl, 2,2-dimethyldioxolanyl, dioxanyl, morpholinyl or thiomorpholinyl. The piperidinyl radical can be substituted by 1, 2, 3 or 4 $C_1$-$C_4$-alkyl groups, in particular methyl groups. A preferred piperidinyl radical is 2,2,6,6-tetramethylpiperidinyl. The nitrogen-containing heterocyclic radicals can be bonded via a nitrogen atom or a carbon atom.

An unsaturated non-aromatic heterocyclic radical is, in particular, pyrrolinyl, di- or tetrahydropyridinyl.

An aromatic heterocyclic radical is, in particular, pyridyl, preferably 3- or 4-pyridyl, pyrimidinyl, pyrrolyl, imidazolyl, pyrazolyl, oxazolyl, isoxazolyl, furyl, thienyl, thiazolyl, thiadiazolyl, isothiazolyl or the corresponding benzo derivatives thereof.

R1 preferably represents the abovementioned meanings Aa), Ab), Ac), Ad) and B). According to one embodiment, R1 is in position 7 (position 1 with respect to X). According to a further embodiment, R1 is in position 8 (position 2 with respect to X). According to a further embodiment, R1 is in position 9 (position 3 with respect to X). Positions 7 and 8 and in particular position 7 are preferred.

R2 preferably represents H.

The radical R3 is preferably in position 3 (with respect to Y). According to one embodiment, R3 represents the abovementioned meanings b), e) and g).

According to a further embodiment, R3 represents the abovementioned formula (b).

According to a further embodiment, R3 represents

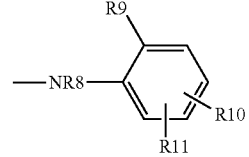

wherein R8, R9, R10 and R11 have the meanings given above. R10 and R11 are preferably in the 3- and 5-position.

According to a further embodiment, R3 represents

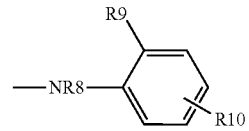

wherein R8, R9 and R10 have the meanings given above. R10 is preferably in the 4-position.

R4, R5, R6, R7 and R8 preferably represent H.

R9, R10 and R11 preferably represent the abovementioned meanings a), b), e), f), g) and h), and in particular H, $NH_2$, $C_1$-$C_6$-alkoxy or halogen.

R12 preferably represents H.

If R1 represents the meaning Ae), it is preferably a non-aromatic heterocyclic radical having 5 or 6 ring atoms, which contains 1 or 2 oxygen hetero atoms, and in particular tetrahydropyranyloxy or 2,2-dimethyldioxolanyl.

One embodiment of the invention are the compounds of the formula Ia:

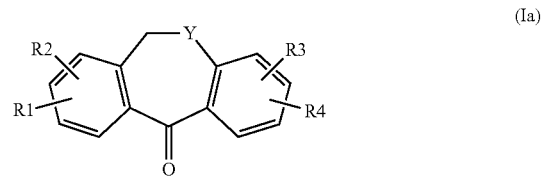

(Ia)

wherein Y represents O or S and R1, R2, R3 and R4 have the abovementioned meanings.

A further embodiment are the compounds of the formula Iaa

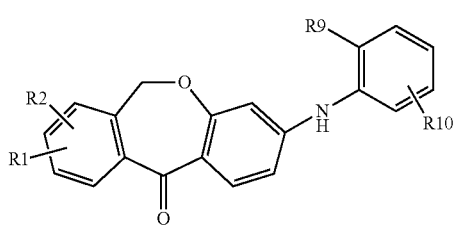
(Iaa)

wherein R1, R2, R9 and R10 have the meanings given above.

According to one embodiment, in the formulae Ia and Iaa R2 and R4 represent H. According to one embodiment, R1 is in position 1 or 2 (relative to the methylene group of the 7-membered ring) and R3 is in position 2 (relative to Y). According to a further embodiment, R2 and R4 represent H and R1 is in position 1 or 2 (relative to the methylene group of the 7-membered ring) and R3 is in position 2 (relative to Y).

A further embodiment are the compounds of the formulae Iab and Iac

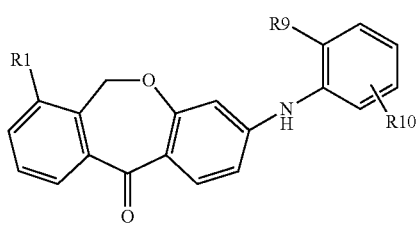
(Iab)

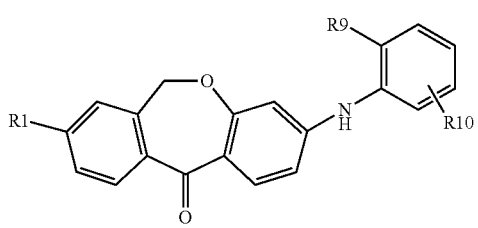
(Iac)

wherein R1, R9 and R10 have the meanings given above.

A further embodiment of the invention are the compounds of the formula Ib

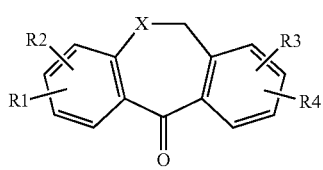
(Ib)

wherein X represents O or S and R1, R2, R3 and R4 have the meanings given above.

A further embodiment are the compounds of the formula Iba:

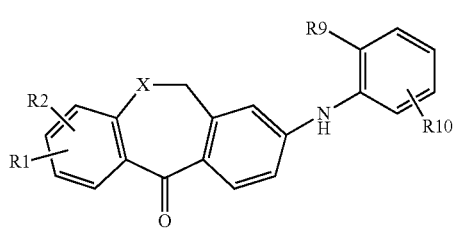
(Iba)

According to one embodiment, in the formulae Ib and Iba R2 and R4 represent H. According to one embodiment, R1 is in position 1 or 2 (relative to X) and R3 is in position 2 (relative to the methylene group of the 7-membered ring). According to a further embodiment, R2 and R4 represent H and R1 is in position 1 or 2 (relative to X) and R3 is in position 2 (relative to the methylene group of the 7-membered ring).

A further embodiment are the compounds of the formula Ibb

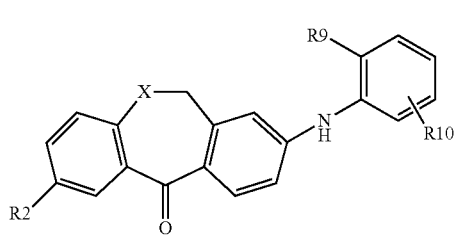
(Ibb)

wherein X represents O or S and R1, R9 and R10 have the meanings given above.

A further embodiment are the compounds of the formula Ibc (Ibc)

wherein X represents O or S and R2, R9 and R10 have the meanings given above.

A further embodiment are the compounds of the formula Ic

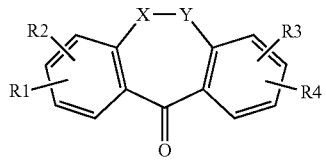
(Ic)

wherein —X—Y— represents —CH$_2$—CH$_2$— or —CH=CH— and R1, R2, R3 and R4 have the meanings given above.

A further embodiment are the compounds of the formula Ica:

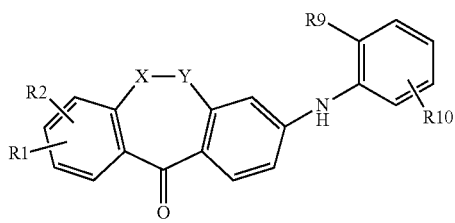

(Ica)

wherein —X—Y— represents —CH$_2$—CH$_2$— or —CH=CH— and R1, R2, R9 and R10 have the meanings given above.

According to one embodiment, in the formulae Ic and Ica R2 and R4 represent H. According to one embodiment, R1 is in position 1 or 2 (relative to X) and R3 is in position 2 (relative to Y). According to a further embodiment, R2 and R4 represent H and R1 is in position 1 or 2 (relative to X) and R3 is in position 2 (relative to Y).

A further embodiment are the compounds of the formulae Icb and Icc

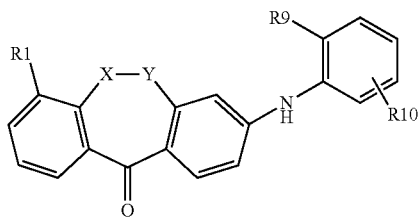

(Icb)

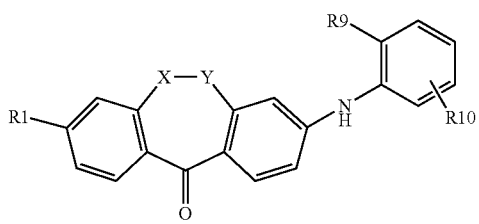

(Icc)

wherein —X—Y— represents —CH$_2$—CH$_2$— or —CH=CH— and R1, R2, R9 and R10 have the meanings given above.

The invention also includes the physiologically acceptable salts of the compounds of the formula I. In the present case, these are, in particular, the acid addition salts. Inorganic acids, such as hydrochloric acid, sulfuric acid or phosphoric acid, or organic acids, such as tartaric acid, citric acid, maleic acid, fumaric acid, malic acid, mandelic acid, ascorbic acid, gluconic acid, methanesulfonic acid, benzenesulfonic acid or toluenesulfonic acid and the like, are employed for formation of the acid addition salts.

Where the compounds according to the invention have centers of asymmetry, the invention likewise provides the racemates and the individual optical isomers (enantiomers, diastereomers).

The invention also provides the solvates of the compounds of the formula I or of the salts thereof, in particular the hydrates.

The preparation of the compounds of the formula I which are substituted at position 7, wherein X—Y represents CH$_2$—CH$_2$ or CH=CH, is carried out by the processes explained by way of example in equations I to III.

Equation I: Synthesis of the basic ring system with substitution in position 7

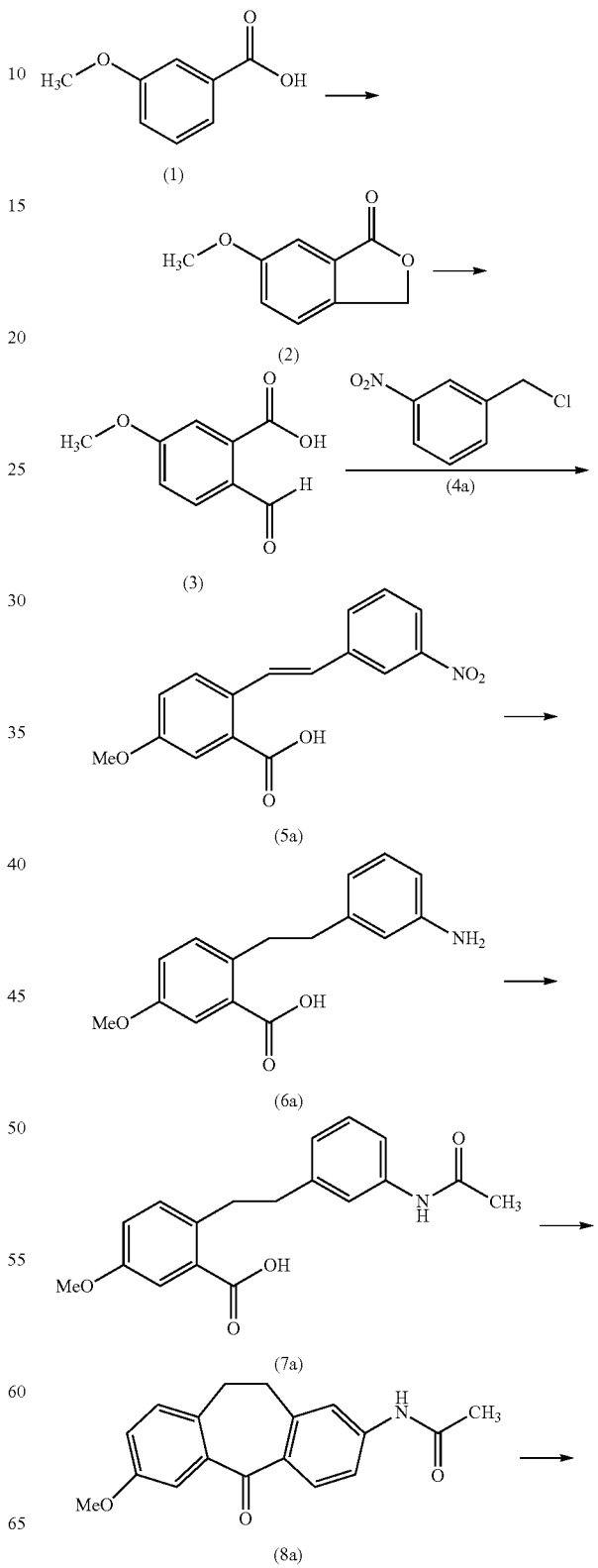

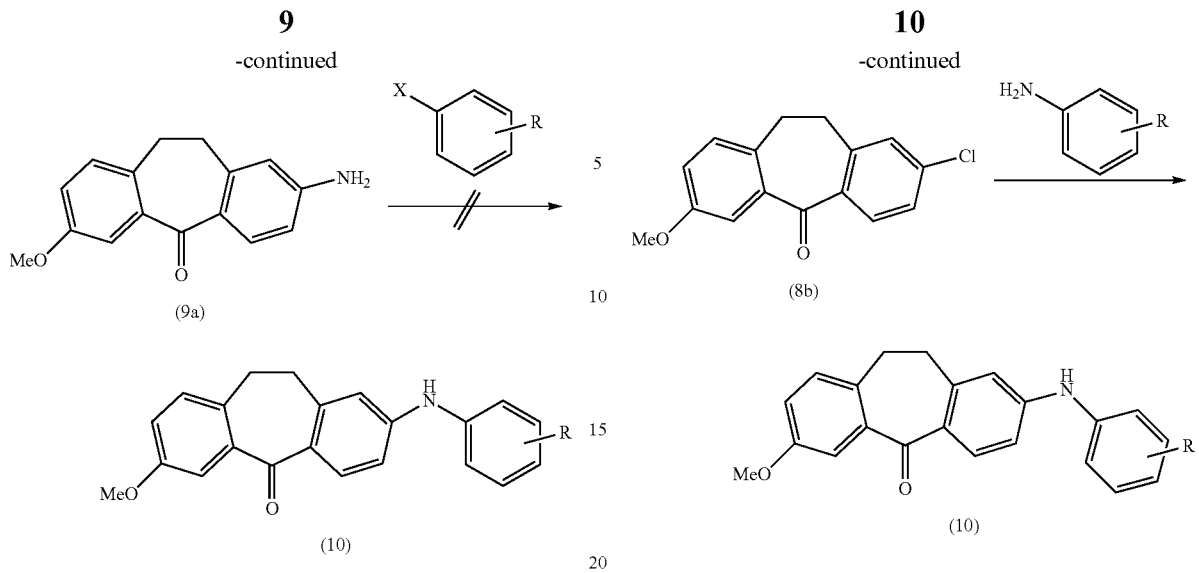

Starting from 3-methoxybenzoic acid (1), a formyl group is introduced via the phthalide (2). By means of a Wittig reaction, the unsaturated compound (5a) is obtained, which can be hydrogenated in the conventional manner, for example using a noble metal catalyst, such as Pt or Pd. Before the cyclization by Friedel-Crafts acylation, the amino group is protected by a suitable protective group, which is removed after the Friedel-Crafts acylation. After reaction with an aryl halide, compound (10) is obtained.

Equation II shows an alternative process for the preparation of (10), with which the use of the protective group can be avoided:

Equation II:

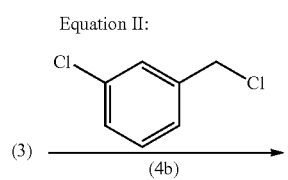

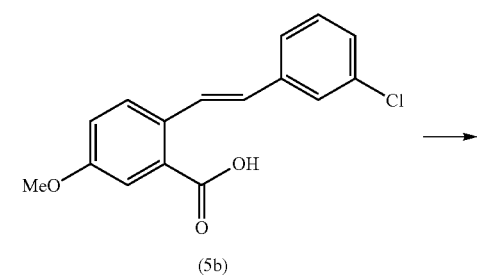

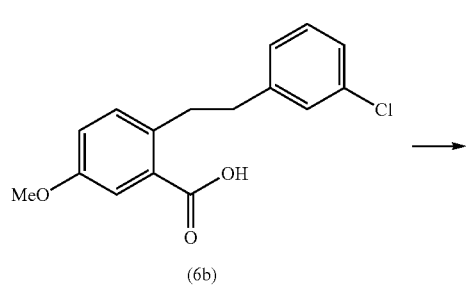

The compounds (10) methoxy-substituted at position 7 can be converted into the hydroxy compounds (11) by ether cleavage, for example by means of aqueous HBr, see equation III.

Equation III:

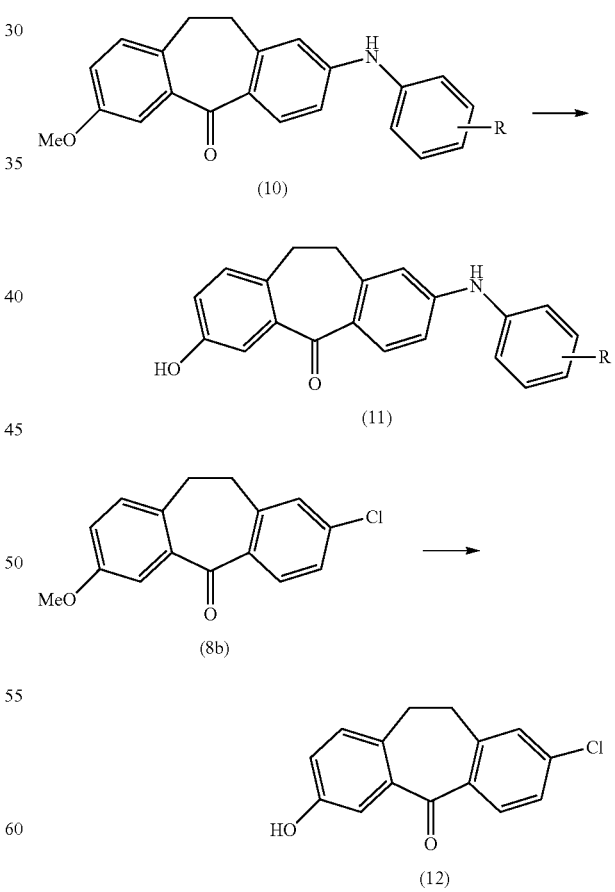

The hydroxyl group at position 7 allows further substitution, for example via the Williams ether synthesis or the Mitsunobu reaction, see equation IV:

Equation IV:

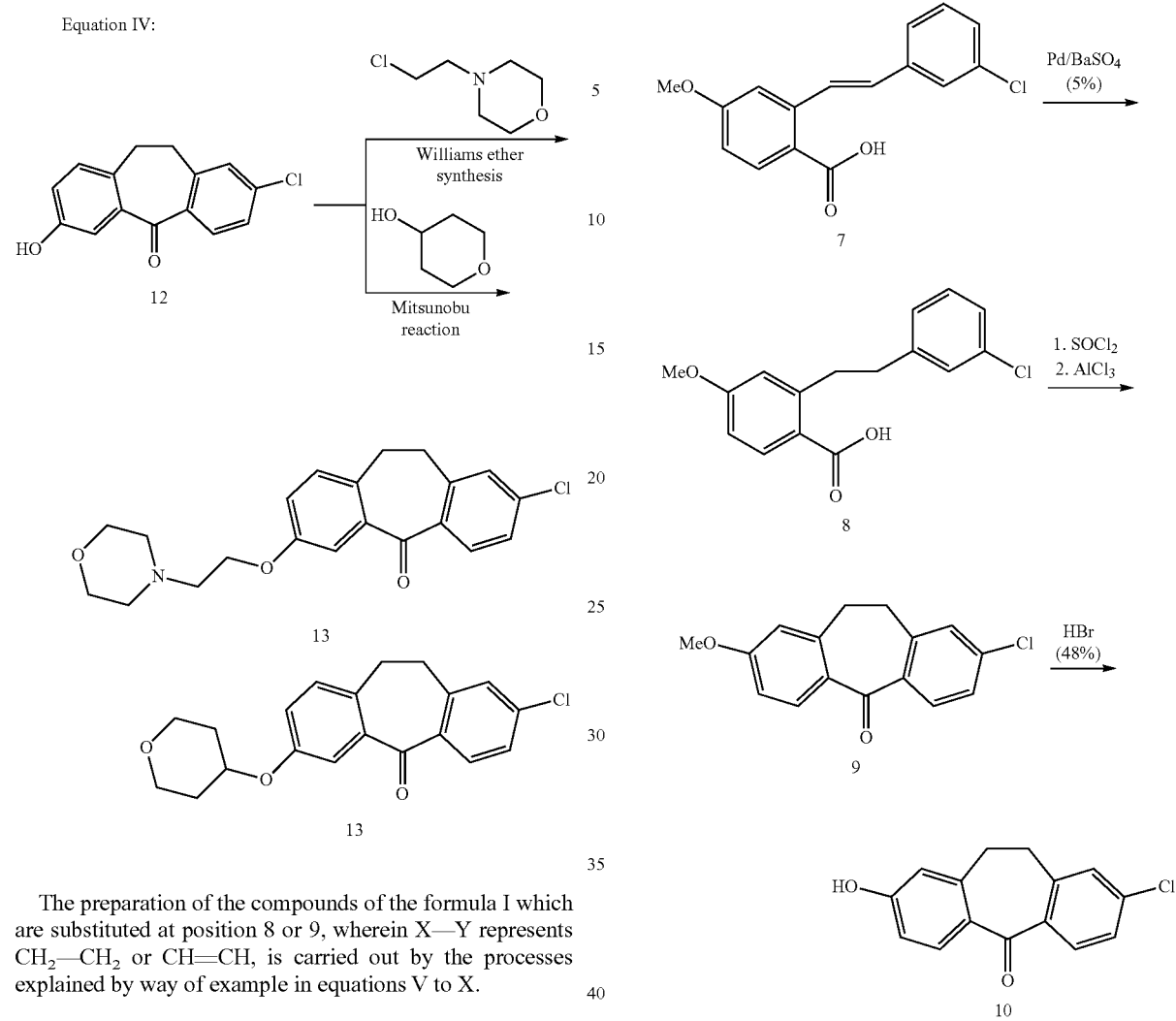

The preparation of the compounds of the formula I which are substituted at position 8 or 9, wherein X—Y represents CH$_2$—CH$_2$ or CH=CH, is carried out by the processes explained by way of example in equations V to X.

Equation V: Synthesis of the basic ring system for substitution in position 8

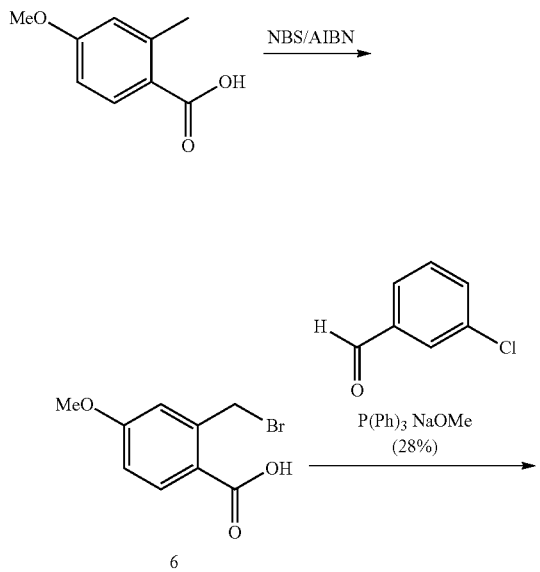

Equation VI: Synthesis of the basic ring system for substitution in position 9

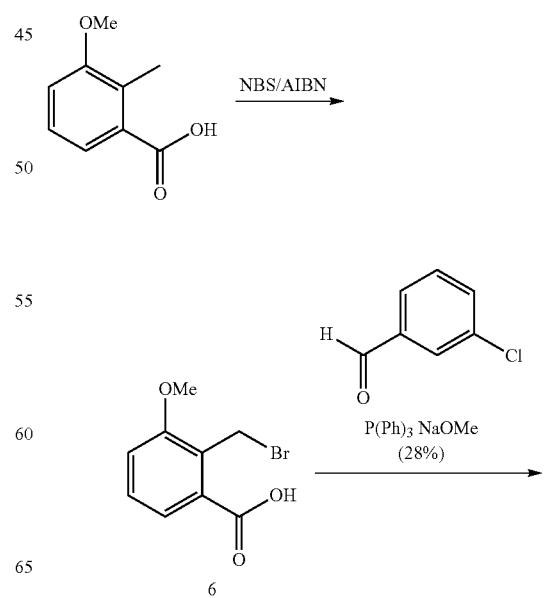

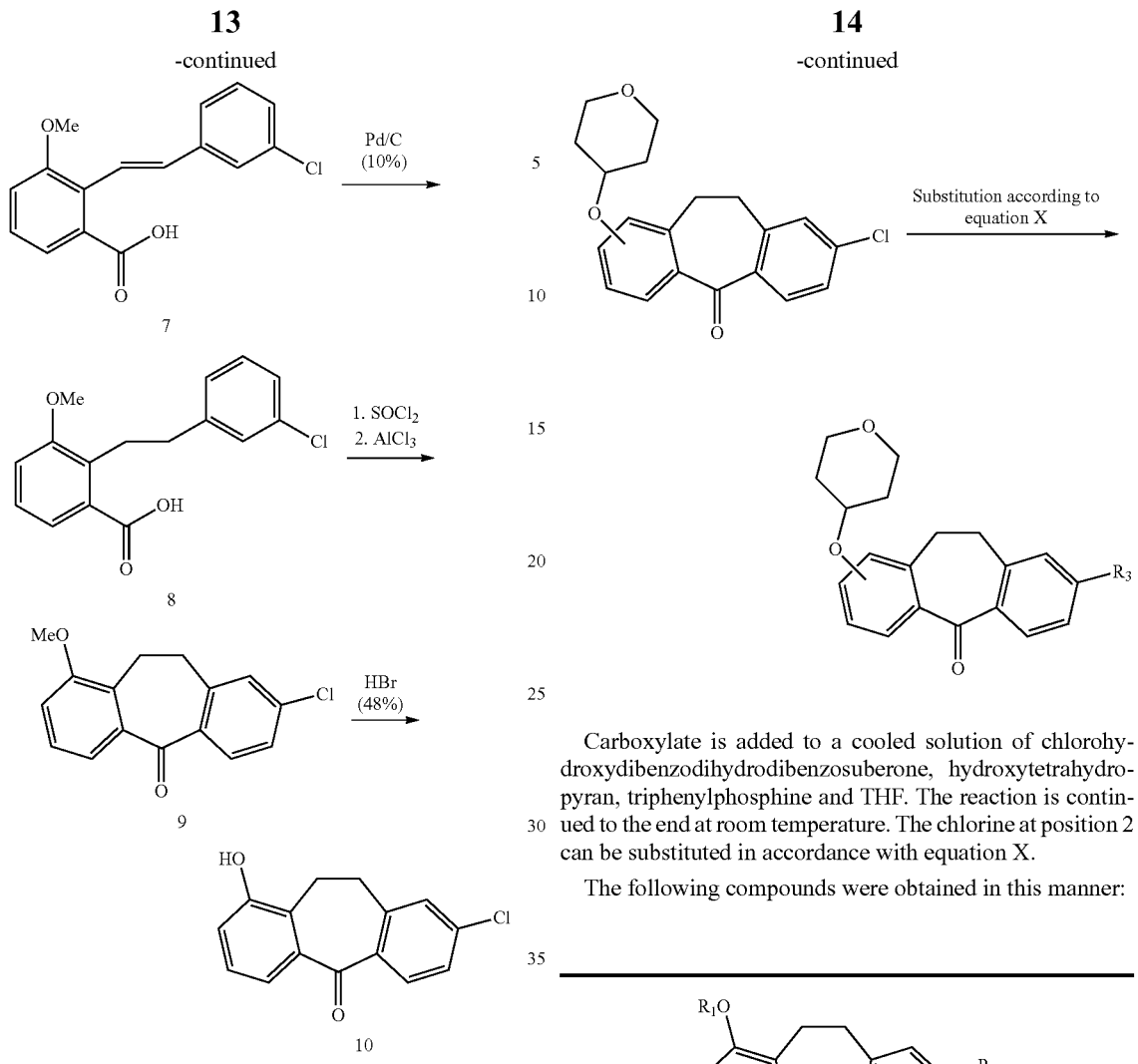

Starting from methoxymethylbenzoic acid, a bromination is first carried out with N-bromosuccinimide (NBS). The bromomethylmethoxybenzoic acid (6) formed is reacted with 3-chlorobenzaldehyde in a Wittig reaction to give chlorophenylvinylmethoxybenzoic acid (7). The subsequent hydrogenation of the chlorophenylvinylmethoxy-benzoic acid is carried out in the conventional manner using noble metal catalysts, such as Pd/BaSO$_4$ (substitution in position 8) or Pd/C (substitution in position 9). The carboxylic acid (8) is converted into the acid chloride, for example by reaction with thionyl chloride. The subsequent cyclization to (9) is carried out by Friedel-Crafts acylation with suitable Lewis acids, such as AlCl$_3$. Compound (10) is then obtained by ether cleavage, for example with aqueous hydrogen bromide.

Equation VII: Substitution with alcohols

Carboxylate is added to a cooled solution of chlorohydroxydibenzodihydrodibenzosuberone, hydroxytetrahydropyran, triphenylphosphine and THF. The reaction is continued to the end at room temperature. The chlorine at position 2 can be substituted in accordance with equation X.

The following compounds were obtained in this manner:

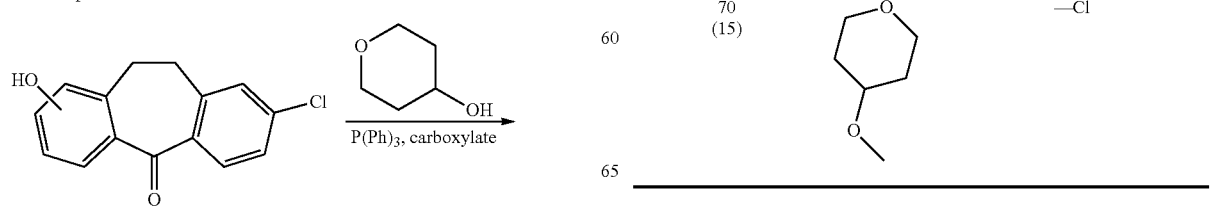

Equation VIII: Substitution with alkyl halides

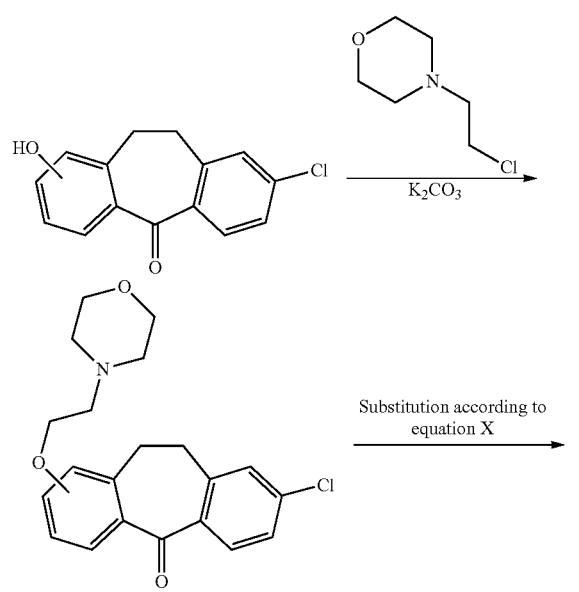

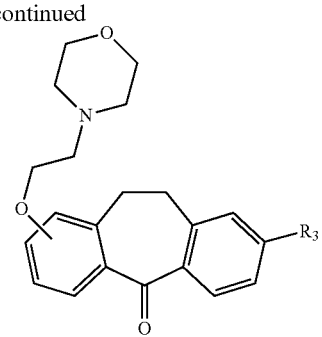

A mixture of the phenolic compound, N-2-chloroethyl-morpholine and $K_2CO_3$ is stirred for several hours, with heating. After cooling, the desired compound is obtained in the conventional manner and the organic phase is separated off, washed and concentrated. The chlorine at position 2 can be substituted in accordance with equation X.

The following compounds were obtained in this manner:

| Compounds in position 9 | | | Compounds in position 8 | | |
|---|---|---|---|---|---|
| Compound of Example no. | $R_1$ | $R_3$ | Compound of Example no. | $R_1$ | $R_3$ |
| 73 (11j) | morpholinoethyl | NH-(2,4-difluorophenyl) | 56 (12e) | morpholinoethyl | NH-(2,4-difluorophenyl) |
| 89 (16) | morpholinoethyl | —Cl | 90 (17) | morpholinoethyl | —Cl |

Equation IX: Preparation of diols:
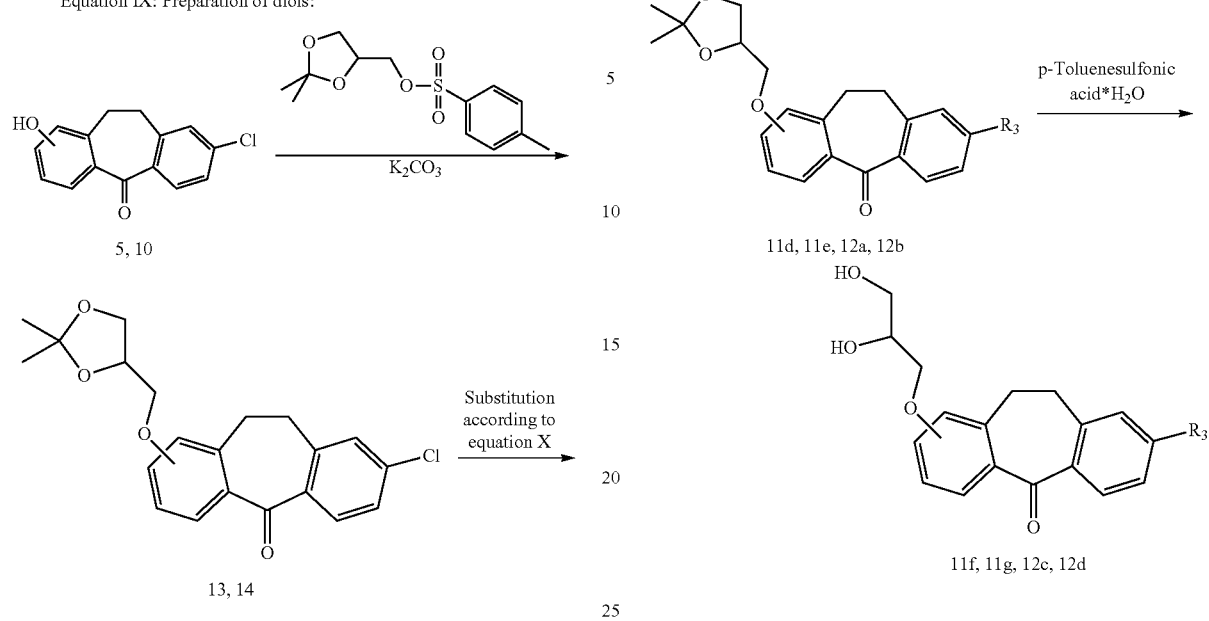
The following compounds were obtained in this manner:

-continued

| Compounds in position 9 | | | Compounds in position 8 | | |
|---|---|---|---|---|---|
| Compound of Example no. | $R_1$ | $R_3$ | Compound of Example no. | $R_1$ | $R_3$ |
| 65 (13) | (2,2-dimethyl-1,3-dioxolan-4-yl)methyl | —Cl | 87 (14) | (2,2-dimethyl-1,3-dioxolan-4-yl)methyl | —Cl |

Equation X: Substitution of the ring system at position 2

4, 5, 9, 10 → 11 a-c

The mixture of chlorodihydrodibenzosuberenone, Pd(OAc)$_2$, phosphine ligand (2-(dicyclohexylphosphino)-2',4',6'-triisopropylbiphenyl), NaOtert-Bu, toluene, tert-BuOH and the amine $R_3NH_2$ is stirred at elevated temperatures for several hours. After cooling, the desired product is obtained in the conventional manner.

The following compounds were obtained in this manner:

| Compound of Example no. | $R_1$ | $R_3$ |
|---|---|---|
| 63 (11a) | —CH$_3$ | N-methyl-2,4-difluoroaniline |
| 64 (11b) | —CH$_3$ | N-methyl-2-aminoaniline |
| 62 (11c) | —OH | N-methyl-2,4-difluoroaniline |

The preparation of the compounds of the formula I which are substituted at position 7, wherein one of the ring atoms X or Y represents CH$_2$, is carried out by the process explained in equation XI.

After esterification of the starting compound 2-methyl-4-nitrobenzoic acid, bromination is carried out with N-bromosuccinimide (NBS) in the conventional manner. The brominated educt is reacted with the phenol in the presence of potassium carbonate. After hydrolysis of the ester, for example with KOH, cyclization is carried out, for example with polyphosphoric acid in an organic solvent, such as sulfolane. The nitro group is then reduced to the amino group in the conventional manner, for example with Sn/HCl. It is advisable to work at elevated temperatures, expediently at the boiling temperature of the solvent or under reflux.

The preparation of the compounds of the formula I wherein one of the ring atoms X or Y represents SO or SO$_2$ is carried out by oxidation of the compounds wherein Y represents S in the conventional manner, for example with per-compounds, such as m-chloroperbenzoic acid.

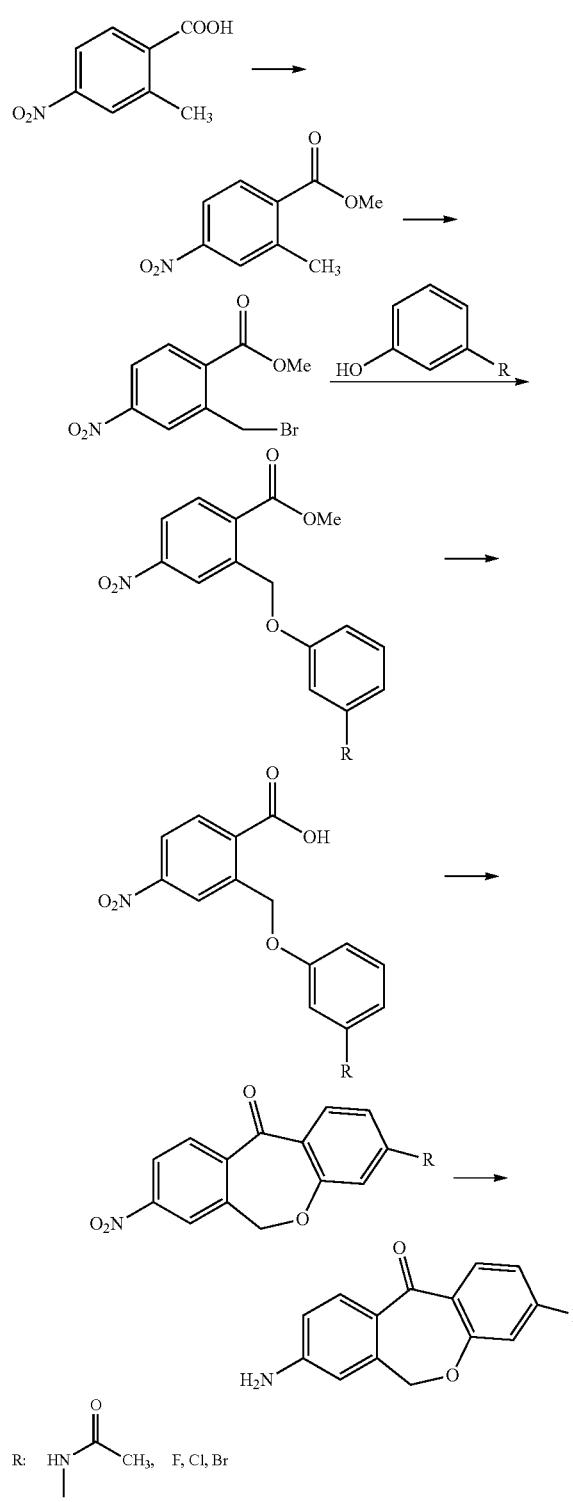

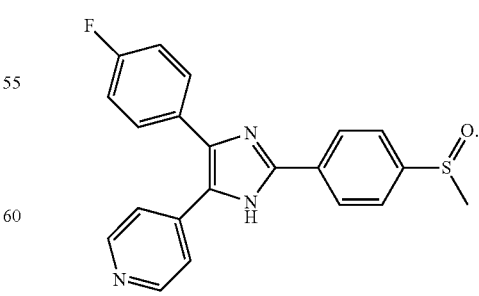

periodontal diseases, restenosis, alopecia, T-cell depletion with HIV infections or AIDS, psoriasis, acute pancreatitis, rejection reactions with allogenic transplants, lung inflammation of allergic origin, arteriosclerosis, multiple sclerosis, cachexia, Alzheimer's disease, stroke, jaundice, colitis ulcerosa, Crohn's disease, inflammatory bowel disease (IBD), ischaemia, congestive cardiac insufficiency, pulmonary fibrosis, hepatitis, glioblastoma, Guillain-Barré syndrome, systemic lupus erythematosus, adult respiratory distress syndrome (ARDS) and respiratory distress syndrome.

The compounds according to the invention can be administered either as individual therapeutic active compounds or as mixtures with other therapeutic active compounds. The compounds can be administered by themselves, but in general they are dosed and administered in the form of pharmaceutical compositions, i.e. as mixtures of the active compounds with suitable pharmaceutical carriers or diluents. The compounds or compositions can be administered orally or parenterally, preferably they are administered in oral dosage forms.

The nature of the pharmaceutical composition or carrier or of the diluent depends on the desired form of administration. Oral compositions for example can be in the form of tablets or capsules and can contain conventional excipients, such as binders (e.g. syrup, acacia, gelatin, sorbitol, tragacanth or polyvinylpyrrolidone), fillers (e.g. lactose, sugar, maize starch, calcium phosphate, sorbitol or glycine), lubricants (e.g. magnesium stearate, talc, polyethylene glycol or silicon dioxide), disintegrating agents (e.g. starch) or wetting agents (e.g. sodium lauryl sulfate). Liquid oral preparations can be in the form of aqueous or oily suspensions, solutions, emulsions, syrups, elixirs or sprays and the like. They can also be in the form of a dry powder, which is prepared for administration by reconstitution with water or another suitable carrier. Such liquid preparations can contain conventional additives, for example suspending agents, flavor substances, diluents or emulsifiers. Solutions or suspensions with conventional pharmaceutical carriers can be employed for parenteral administration.

The compounds or compositions according to the invention can be administered to mammals (humans or animals) in a dose of from about 0.5 mg to 100 mg per kg of body weight per day. They can be administered in a single dose or in several doses.

The action spectrum of the compounds as inhibitors of the release of TNF-α and IL-1β was investigated with the aid of the test systems as described by Donat C. and Laufer S. in Arch. Pharm. Pharm. Med. Chem. 333, Suppl. 1, 1-40, 2000. The $IC_{50}$ values obtained were set in relation to the values for the compound SB-203580 of the formula The compounds according to the invention show an action which is immunomodulating and inhibits the release of TNF-α and IL-1β in vitro and in vivo. The compounds according to the invention are therefore suitable for treatment of diseases related to a disturbance in the immune system. They are suitable, for example, for treatment of autoimmune diseases, cancer, rheumatic arthritis, gout, septic shock, osteoporosis, neuropathic pain, HIV propagation, HIV dementia, viral myocarditis, insulin-dependent diabetes, The numerical values given in the following table are therefore the relative activity, calculated from the ratio of $IC_{50}$ (SB-203580)/$IC_{50}$ (test compound). The higher the numerical value, the more active the compound. The compounds in which R1 represents H represent the prior art according to WO2006/120010.

TABLE

Inhibition of p38 MAP kinase and TNF-α

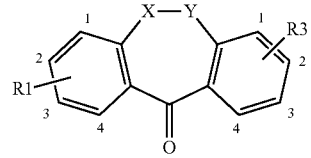

(I)

| R1 | R3 | X | Y | p38 MAP kinase | Inhibition of TNF-α |
|---|---|---|---|---|---|
| H | 2-[NH-(2-NH$_2$-phenyl)] | CH$_2$ | O | 0.23 | |
| 2-NH$_2$ | 2-[NH-(2-NH$_2$-phenyl)] | CH$_2$ | O | 0.93 | |
| 2-OCH$_3$ | 2-[NH-(2-NH$_2$-phenyl)] | CH$_2$ | O | 0.57 | |
| 2-(OCH$_2$CH$_2$-morpholine) | 2-[NH-(2-NH$_2$-phenyl)] | CH$_2$ | O | 0.32 | |
| H | 2-[NH-(2,4-di-F-phenyl)] | CH$_2$ | O | 0.31 | 0.09 |
| 2-(NHCO-morpholine) | 2-[NH-(2,4-di-F-phenyl)] | CH$_2$ | O | 0.51 | |
| 2-(OCH$_2$CH$_2$-morpholine) | 2-[NH-(2,4-di-F-phenyl)] | CH$_2$ | O | 1.92 | 0.02 |
| 1-OCH$_3$ | 2-[NH-(2,4-di-F-phenyl)] | CH$_2$ | O | 1.11 | 0.04 |
| 2-(OCH$_2$CH$_2$—N(CH$_3$)) | 2-[NH-(2,4-di-F-phenyl)] | CH$_2$ | O | 1.02 | |
| H | 2-[NH-(2-NH$_2$-phenyl)] | CH$_2$ | CH$_2$ | 0.54 | 0.51 |
| 3-OCH$_3$ | 2-[NH-(2-NH$_2$-phenyl)] | CH$_2$ | CH$_2$ | 1.00 | 0.91 |
| (S)-3-[OCH$_2$—CH(OH)—CH$_2$OH] | 2-[NH-(2-NH$_2$-phenyl)] | CH$_2$ | CH$_2$ | 1.54 | >5 |
| (S)-3-(OCH$_2$-3,3-di-CH$_3$-2,4-dioxolane) | 2-[NH-(2-NH$_2$-phenyl)] | CH$_2$ | CH$_2$ | 1.31 | >5 |
| 3-(OCH$_2$-3,3-di-CH$_3$-2,4-dioxolane) | 2-[NH-(2-NH$_2$-phenyl)] | CH$_2$ | CH$_2$ | 0.72 | >5 |
| H | 2-[NH-(2,4-di-F-phenyl)] | CH$_2$ | CH$_2$ | 0.52 | 0.49 |
| 1-OH | 2-[NH-(2,4-di-F-phenyl)] | CH$_2$ | CH$_2$ | 2.26 | 0.06 |
| 1-[OCH$_2$—CH(OH)—CH$_2$OH] | 2-[NH-(2,4-di-F-phenyl)] | CH$_2$ | CH$_2$ | 1.76 | |
| 1-(OCH$_2$CH$_2$-morpholine) | 2-[NH-(2,4-di-F-phenyl)] | CH$_2$ | CH$_2$ | 1.26 | |
| 2-OCH$_3$ | 2-[NH-(2,4-di-F-phenyl)] | CH$_2$ | CH$_2$ | 2.60 | |
| 2-(OCH$_2$CH$_2$-morpholine) | 2-[NH-(2,4-di-F-phenyl)] | CH$_2$ | CH$_2$ | 2.53 | |
| 2-(OCH2—CH2OH) | 2-[NH-(2,4-di-F-phenyl)] | CH$_2$ | CH$_2$ | 2.60 | |
| 3-OH | 2-[NH-(2,4-di-F-phenyl)] | CH$_2$ | CH$_2$ | 2.03 | 1.80 |
| 3-OCH$_3$ | 2-[NH-(2,4-di-F-phenyl)] | CH$_2$ | CH$_2$ | 1.59 | 0.70 |
| (S)-3-(OCH$_2$-3,3-di-CH$_3$-2,4-dioxolane) | 2-[NH-(2,4-di-F-phenyl)] | CH$_2$ | CH$_2$ | 1.86 | 3.79 |
| 3-(O-tetrahydro-pyran-4-yl) | 2-[NH-(2,4-di-F-phenyl)] | CH$_2$ | CH$_2$ | 0.74 | 1.98 |
| (S)-3-(OCH$_2$-3,3-di-CH$_3$-2,4-dioxolane) | 2-[NH-(2,4-di-F-phenyl)] | CH$_2$ | CH$_2$ | 1.04 | >5 |
| 3-(OCH$_2$—CH(OH)) | 2-[NH-(2,4-di-F-phenyl)] | CH$_2$ | CH$_2$ | 3.00 | 4.98 |
| 3-(OCH$_2$—CH$_2$CH$_2$OH) | 2-[NH-(2,4-di-F-phenyl)] | CH$_2$ | CH$_2$ | 4.85 | >5 |
| 3-(OCH$_2$-3,3-di-CH$_3$-2,4-dioxolane) | 2-[NH-(2,4-di-F-phenyl)] | CH$_2$ | CH$_2$ | 0.32 | 3.75 |
| 3-(O—CH$_2$-tetrahydro-pyran-4-yl) | 2-[NH-(2,4-di-F-phenyl)] | CH$_2$ | CH$_2$ | 3.04 | 4.90 |
| H | 2-[NH-(2-NH$_2$-4F-phenyl)] | CH$_2$ | CH$_2$ | 0.37 | 0.67 |
| 3-OCH$_3$ | 2-[NH-(2-NH$_2$-4F-phenyl)] | CH$_2$ | CH$_2$ | 0.92 | 0.73 |
| H | 2-[NH-(2-NH$_2$-4F-phenyl)] | CH$_2$ | O | 0.52 | 0.08 |
| 2-NH$_2$ | 2-[NH-(2-NH$_2$-4F-phenyl)] | CH$_2$ | O | 1.15 | 0.24 |
| H | 2-[NH-(2-OCH$_3$-phenyl)] | CH$_2$ | O | 0.09 | 0.13 |
| 2-NH$_2$ | 2-[NH-(2-OCH$_3$-phenyl)] | CH$_2$ | O | 0.14 | 0.04 |
| 3-OCH$_3$ | 2-[NH-(2-OCH$_3$-phenyl)] | CH$_2$ | CH$_2$ | 0.11 | 0.18 |

It can be seen that the compounds according to the invention have an excellent activity and are superior to the compounds of WO 2006/120010.

The following examples illustrate the invention without limiting it.

Equipment and Methods

| | |
|---|---|
| Melting points | Büchi Melting Point B-545 (thermodynamic correction) |
| NMR spectroscopy | Bruker Avance 200 (200 MHz) |
| IR spectroscopy | Perkin-Elmer Spectrum One (ATR) |
| GC-MS | Hewlett Packard HP 6890 Series GC-System Hewlett Packard HP 5973 Mass Selective Detector GC column: HP-5MS 5% phenylmethylsiloxane ESI-MS: 70 eV |

GC Method:

| Temperature [° C.] | Migration time [min] |
|---|---|
| 160 | 1 |
| 160 → 240 | 10 |
| 240 | 5 |
| 240 → 270 | 10 |
| 270 | 35 |

Abbreviations:
MeOH Methanol
NaOMe Sodium methylate
KOtert-Bu Potassium tert-butylate
Tert-BuOH tert-Butanol
EtOH Ethanol DMF Dimethylformamide
THF Tetrahydrofuran
MC Methylene chloride
i. vac. in vacuo
EA Ethyl acetate General Method A For the synthesis of the stilbenes by means of a Wittig reaction, the stated amount of triphenylphosphine is dissolved in MeOH. While stirring, the corresponding benzyl chloride is added dropwise and the mixture is heated under reflux for 2 hours. The reaction mixture is cooled to 0° C. and the corresponding aldehyde is added. The stated amount of NaOMe solution is then added dropwise at 0° C. in the course of approx. 45 min. When the dropwise addition has ended, the reaction mixture is subsequently stirred at 0° C. for 3 h and poured on to a stirred mixture of 75 g of ice and 175 ml of water. The mixture is filtered with suction, the residue on the filter is washed with approx. 50 ml of water and the combined aqueous phases are washed several times with methylene chloride in vacuo. By acidification of the aqueous phase, the product is obtained in the form of a precipitate, which is filtered off. Purification is carried out by recrystallization from MeOH/$H_2O$.

General Method B

For the synthesis of the ketones by means of Friedel-Crafts acylation, the stated amount of acid is suspended in methylene chloride and the mixture is flushed with argon. After heating to the reflux temperature, a solution of thionyl chloride in 50 ml of methylene chloride is added dropwise in the course of 1 hour, while stirring, and the mixture is stirred for a further hour. After cooling to room temperature, a suspension of $AlCl_3$ in methylene chloride is added dropwise in the course of 45 min and the reaction mixture is subsequently stirred at room temperature for 30 min and poured on to a mixture of 30 g of ice and 50 ml of water, while stirring. The hydrolysis mixture is stirred for approx. 30 min, the precipitate is filtered off and the two phases of the filtrate are separated. The product is obtained by concentration of the organic phase in vacuo. Purification is carried out by recrystallization with MeOH.

General Method C

For the preparation of the test compounds, a mixture of aryl halide, amine, $Pd(OAc)_2$, phosphine ligand, KOtert-Bu, toluene and tert-BuOH is heated to 100° C. under argon and stirred at this temperature for the stated time. Thereafter, the mixture is cooled to room temperature, hydrolysis is carried out with 150 ml of $H_2O$, the mixture is extracted 3× with 200 ml of diethyl ether each time and the organic phase is filtered and concentrated in vacuo. Purification is carried out via flash chromatography.

General Method D $SnCl_2$×5 $H_2O$ is added to a solution of the nitro compound in EtOH. The mixture is refluxed for 5 h. It is then cooled and rendered alkaline with 20% strength NaOH. It is extracted 3× with 200 ml of ethyl acetate each time and the organic phase is concentrated in vacuo.

General Method E

For the preparation of 2-chloro-7-(S-1,2-isopropylideneglycer-3-yl)-10,11-dihydrodibenzo[a,d]cyclohepten-5-one, 0.57 mmol of 2-chloro-7-hydroxy-10,11-dihydrodibenzo[a,d]cyclohepten-5-one is dissolved in 10 ml of anhydrous DMF, and 0.82 mmol of the corresponding α,β-isopropylideneglycerol γ-tosylate and 1.65 mmol of $K_2CO_3$ are added. The reaction mixture is stirred at 80° C. under an argon atmosphere for 24 h. The reaction mixture is cooled to room temperature dissolved in 50 ml of water and extracted with diethyl ether and the organic phase is concentrated in vacuo. The product is obtained in the form of a pale yellow oil.

General Method F

A solution of 2 mmol of $P(Ph)_3$ in 10 ml of THF is added dropwise to a solution of 2 mmol of diisopropyl azodicarboxylate in 20 ml of THF at 0° C. and the mixture is stirred for 1 h. A solution of 2 mmol of 2-chloro-7-hydroxy-10,11-dihydrodibenzo[a,d]cyclohepten-5-one and 2 ml of the corresponding alcohol in THF is then added dropwise and the mixture is stirred at room temperature for 2 h. It is hydrolyzed with water and extracted with ethyl acetate and the organic phase is concentrated in vacuo. Purification is carried out on $SiO_2$ (hexane/ethyl acetate 7+3).

General Method G 1.7 mmol of 2-chloro-7-hydroxy-10,11-dihydrodibenzo[a,d]cyclohepten-5-one, 1.86 mol of alkyl halide and 6.57 mmol of $K_2CO_3$ are dissolved in either DMF or acetonitrile and the solution is stirred at 80° C. for the stated time, cooled to room temperature and dissolved in diethyl ether and water. The organic phase is washed with water and alkali, dried over $MgSO_4$ and concentrated in vacuo.

EXAMPLE 1

6-Methoxyphthalide (2)

A mixture of 20 g (131 mmol) of 3-methoxybenzoic acid, 13 ml (160 mmol) of 37% strength formalin soln., 16 ml (162 mmol) of 37% strength HCl and 150 ml of 100% strength acetic acid is heated to 90° C., while stirring. After a clear solution has formed, the stirrer is switched off and the mixture is left at this temperature for 14 hours. The acetic acid is stripped off at 80° C. in vacuo, the residue is taken up in 150 ml of toluene and the mixture is concentrated to 80 ml. The 80° C. hot solution is washed with 40 ml portions of 20% strength $Na_2SO_4$ solution until the pH of the aqueous solution is alkaline, and is then washed with 40 ml of $H_2O$. After addition of 6 ml of morpholine, the organic phase is stirred at 80° C. for 2 h and then washed with 50 ml portions of 10% strength $H_2SO_4$ until the aqueous phase is acidic, and twice with 50 ml of $H_2O$ each time. For crystallization of the product, the mixture is concentrated to 50 ml, a seed crystal is added if necessary, and the mixture is stirred until it has cooled to room temperature. The product is obtained by filtering off in the form of white crystals.

Yield: 13.8 g (64%); m.p.: 107.6° C.

IR (ATR): 2945 $(C-H)_{aliph}$, 1745 (C=O), 1489, 1320, 1278, 1247, 1054, 1017, 990, 9056, 769.

$^1$H-NMR (DMSO-d6) δ in ppm: 3.84 (s, 3H, —$OCH_3$), 5.33 (s, 2H, $C^3$—H), 7.28 (s, 1H, $C^7$—H), 7.31 (d, J=8.3 Hz, $C^4$—H), 7.56 (d, 1H, J=8.3 Hz, $C^5$—H).

EXAMPLE 2

2-Formyl-5-methoxy-benzoic acid (3)

10 g (61 mmol) of 6-methoxyphthalide, 11.4 g (64.0 mmol) of NBS and 200 ml of chlorobenzene are mixed, while stirring, the suspension is heated to 85° C. and 2 ml of a solution of 100 mg of AIBN in 10 ml of chlorobenzene are added. In the course of a few minutes, the temperature rises to 110° C. and a red solution forms. After the rise in-temperature has subsided, the remaining 8 ml are added and the mixture is stirred at 85° C. for 40 min. After cooling to 0° C., the succinimide which has precipitated out is filtered off and rinsed with chlorobenzene. The filtrate is concentrated until an oily residue forms, which is taken up in 10% strength NaOH solution, and the mixture is washed three times with 300 ml of methylene chloride each time. After acidification of the aqueous phase with concentrated HCl, the mixture is stirred at 0° C. for 1 hour. The acid thereby precipitates out in the form of a white precipitate, which is filtered off.

Yield: 9.6 g (87%); melting point: 166.2° C.

IR (ATR): 2903 (COOH), 2601 (C—H)$_{aliph}$, 1703, 1586 (C=O), 1497, 1278, 1210, 1187, 1142, 1072, 1025, 897, 823, 736.

H$_1$-NMR (DMSO-d6) δ in ppm: 3.64 (s, 3H, —OCH$_3$), 6.59 (s, 1H, —CHO), 7.23-7.86 (m, 3H, C$^3$—H, C$^4$—H, C$^6$—H). 10.3 (s, 1H, —COOH).

EXAMPLE 3

2-(3-Nitrophenethenyl)-5-methoxybenzoic acid (5a)

For the synthesis of compound 5a by method A, 15.3 g (0.058 mol) of triphenylphosphine, in 100 ml of MeOH, 10.0 g (0.058 mol) of nitrobenzyl chloride (dissolved in 50 ml of MeOH), 9.6 g (0.058 mol) of 2-formyl-5-methoxybenzoic acid and 28.0 g (0.145 mol) of 28% strength NaOMe solution are used. Yield: 13.5 g (78%); melting point: 174.7° C.

IR (ATR): 2838 (COOH), 2627 (C—H)$_{aliph}$, 1687 (C=O), 1530, 1348, 1266, 1237, 810, 734, 671.

H$_1$-NMR (DMSO-d6) δ in ppm: 3.80 (s, 3H, —OCH$_3$), 6.67 (d, 1H, J=12.1 Hz, CH=CH), 6.98-7.00 (m, 2H, C$^3$H, C$^4$—H, 7.12 (d, 1H, J=12.0 Hz, CH=CH), 7.43-7.47 (m, 3H, C$^6$—H, C$^{5'}$—H, C$^{6'}$—H), 7.88 (s, 1H, C$^{2'}$—H), 7.98 (m, 1H, C$^{4'}$—H).

EXAMPLE 4

2-(3-Chlorophenethenyl)-5-methoxybenzoic acid (5b)

For the synthesis of the compound 5b by method A, 15.3 g (0.058 mol) of triphenylphosphine, in 100 ml of MeOH, 9.4 g (0.058 mol) of chlorobenzyl chloride (dissolved in 50 ml of MeOH), 9.6 g (0.058 mol) of 2-formyl-5-methoxybenzoic acid and 28.0 g (0.145 mol) of 28% strength NaOMe solution are used. Yield: 6.7 g (40%); melting point: 142.3° C.

IR (ATR) 2835 (COOH), 2563 (C—H)$_{aliph}$, 1681 (C=O), 1604, 1594, 1419, 1265, 1251, 1218, 840, 779, 756.

H$_1$-NMR (DMSO-d6) δ in ppm: 3.79 (s, 3H, —OCH$_3$), 7.04 (d, 1H, J=16.3 Hz, CH=CH), 7.16 (dd, 1H, J$_1$=2.7 Hz, J$_2$=7.9 Hz), 7.31-7.36 (m, 2H, C$^{2'}$—H, C$^{4'}$—H), 7.41 (d, 1H, J=7.6, C$^4$—H), 7.46-7.55 (m, 2H, C$^6$—H, C$^{6'}$—H), 7.76 (d, 1H, J=8.8 Hz, C$^3$—H), 7.86 (d, 1H, J=16.4 Hz, CH=CH).

EXAMPLE 5

2-(3-Aminophenethyl)-5-methoxybenzoic acid (6a)

10.0 g (0.033 mol) of 2-(3-nitrophenethenyl)-5-methoxybenzoic acid are suspended in 150 ml of EtOH and 100 mg of Pd/charcoal are added. The mixture is flushed with H$_2$ several times and stirred at room temperature for 72 hours. After filtering off the Pd/charcoal, the mixture is concentrated in vacuo and the residue is recrystallized with MeOH/H$_2$O.

Yield: 8.5 g (95%); melting point 108.5° C.

H$_1$-NMR (DMSO-d6) δ in ppm: 2.61 (2H, m, —CH$_2$—CH$_2$—), 3.05 (m, 2H, —CH$_2$—CH$_2$), 3.75 (s, 3H, —OCH$_3$), 6.36-6.44 (m, 3H, C$^{2'}$—H, C$^{4'}$—H, C$^{6'}$—H), 6.90 (t, 1H, J$_1$=7.6 Hz, J$_2$=7.7 Hz, C$^{5'}$—H), 7.01 (d, 1H, J=8.5 Hz, C$^4$—H), 7.20 (d, 1H, J=8.5 Hz, C$^3$—H), 7.3 (s, 1H, C$^6$—H).

EXAMPLE 6

2-(3-Chlorophenethyl)-5-methoxybenzoic acid (6b)

5.0 g (0.017 mol) of 2-(3-chlorophenethenyl)-5-methoxybenzoic acid are dissolved in a mixture of 75 ml of ethyl acetate and 75 ml of acetonitrile, and 100 mg of Pd/charcoal are added. The mixture is flushed with H$_2$ several times and stirred at room temperature for 5 hours. After filtering off the Pd/charcoal, the mixture is concentrated in vacuo and the residue is recrystallized with MeOH/H$_2$O. Yield: 4.7 g (95%)

H$_1$-NMR (DMSO-d6) δ in ppm: 2.73-2.81 (m, 2H, —CH$_2$—CH$_2$—), 3.05-3.13 (m, 2H, —CH$_2$—CH$_2$—), 3.75 (s, 3H, OCH$_3$), 6.99-7.35 (m, 6H, C$^3$—H, C$^4$—H, C$^6$—H, C$^{2'}$—H, C$^{4'}$—H, C$^{5'}$—H, C$^{6'}$—H).

EXAMPLE 7

2-(3-Acetamidophenethyl)-5-methoxybenzoic acid (7a)

20 g (0.074 mol) of 2-aminophenethyl-5-methoxybenzoic acid are dissolved in 50 ml of acetic anhydride and the solution is stirred at room temperature for 15 hours. Hydrolysis is carried out with 200 ml of ice-water and the mixture is extracted several times with in each case 3×200 ml of ethyl acetate. After concentrating the organic phase in vacuo, a yellow oil is obtained, from which the product is obtained by recrystallization with MeOH/H$_2$O.

Yield: 16.4 g (0.058 mol) (79.0%); melting point: 145.6° C.

IR (ATR) 3265-2933, 2562 (C—H)$_{aliph}$, 1622, 1693, 1593, 1567, 1437, 1420, 1289, 1235, 789, 747.

H$_1$-NMR (DMSO-d6) δ in ppm: 2.01 (s, 3H, —CO—CH$_3$), 2.74 (m, 2H, —CH$_2$—CH$_2$), 3.08 (m, 2H, —CH$_2$—CH$_2$), 3.74 (s, 3H, —OCH$_3$), 6.89 (d, 1H, J=7.6 Hz, C$^{4'}$—H), 6.95 (d, 1H, J=8.5 Hz, C$^{6'}$—H), 7.12-7.20 (m, 2H, C$^{2'}$—H, C$^{6'}$—H), 7.28 (d, 1H, J=2.8 Hz, C$^4$—H), 7.44-7.46 (m, 2H, C$^3$—H, C$^6$—H), 9.89 (s, 1H, —NH—).

EXAMPLE 8

2-Nitro-7-methoxydibenzosuberenone (8d)

For the preparation of 2-nitro-7-methoxydibenzosuberenone by method B, 5.1 g (0.019 mol) of 2-(3-nitrophenylethenyl)-5-methoxybenzoic acid, 150 ml of methylene chloride, 2.42 g (0.02 mol) of thionyl chloride and 3.33 g (0.025 mol) of AlCl$_3$ are used.

Yield: 58%; melting point 163.7° C.

IR (ATR) 3093-3005 (C—H)$_{arom}$, 2921-2838, 1703 (C=O), 1521, 1482, 1431, 1347, 1290, 1223, 1257, 1019, 872, 806, 730, 674.

H$_1$-NMR (DMSO-d6) δ in ppm: 3.81 (s, 3H, —OCH$_3$), 6.92 (dd, 1H, J$_1$=2.4 Hz, J$_2$=8.0 Hz), 7.04 (d. 1H, J=2.5, C$^8$—H), 7.21 (d, 1H, J=7.9, —CH=CH—), 7.70 (d, 1H, J=8.0, C$^3$—H), 8.13-8.24 (m, 2H, C$^2$—H, C$^4$—H), 8.34 (s, 1H, C$^{10}$—H), 8.67 (t, 1H, J=2.0 Hz, C$^7$—H).

EXAMPLE 9

2-Chloro-7-methoxysuberenone (8c)

For the preparation of compound 8c by method B, 5.5 g (0.019 mol) of 2-(3-chlorophenylethenyl)-5-methoxybenzoic acid, 150 ml of methylene chloride, 2.42 g (0.02 mol) of thionyl chloride and 3.33 g (0.025 mol) of AlCl$_3$ are used. M.p. 133.0° C.; yield: 4.8 g (93%)

IR (ATR) 2923-2843 (C—H)$_{aliph}$, 1636, 1605, 1583 (C=O), 1556, 1503, 1298, 1245, 1225, 972, 878, 863, 835, 786.

H$_1$-NMR (DMSO-d6) δ in ppm: 3.89 (s, 3H, —OCH$_3$), 7.06 (d, 1H, J=12.1 Hz, —CH=CH—), 7.25 (d, 1H, J=12.1 Hz, —CH=CH—), 7.37 (dd, 1H, J$_1$=2.9 Hz, J$_2$=8.5 Hz, C$^3$—H), 7.35-7.40 (m, 2H, C$^2$—H, C$^{10}$—H), 7.72 (d, 1H, J=8.7 Hz, C$^8$—H), 7.85 (d, 1H, J=2.2 Hz, C$^4$—H), 8.11 (d, 1H, J=8.6 Hz, C$^7$—H).

EXAMPLE 10

2-Acetamido-7-methoxydibenzosuberone (8a)

For the preparation of compound 8a by method B, 6.0 g (0.019 mol) of 2-(3-acetamidophenethyl)-5-methoxybenzoic acid, 150 ml of methylene chloride, 2.42 g (0.02 mol) of thionyl chloride and 6.66 g (0.05 mol) of AlCl$_3$ are used. Yield 4.66 g (83%

MS m/z (%): 295 (100, M$^+$), 253 (60, M$^+$-COCH$_3$), 238 (12, 253-CH$_3$), 224 (36, 238-NH), 210 (10), 194 (10), 180 (9), 165 (14), 152 (8).

H$_1$-NMR 2.07 (s, 3H, —COCH$_3$), 3.05 (s, 4H, —CH$_2$—CH$_2$), 3.75 (s, 3H, —OCH$_3$), 7.05 (d, 1H, J=8.4 Hz, C$^8$—H), 7.22 (d, 1H, J=8.4 Hz, C$^9$—H), 7.38 (s, 1H, C$^5$—H), 7.52-7.56 (m, 2H, C$^1$—H, C$^3$—H), 7.92 (d, 1H, J=9.3 Hz, C$^4$—H), 10.22 (s, 1H, —NH—).

EXAMPLE 11

2-Chloro-7-methoxydibenzodibenzosuberone (8b)

For the preparation of compound 8b by method B, 5.5 g (0.019 mol) of 2-(3-chlorophenylethyl)-5-methoxybenzoic acid, 150 ml of methylene chloride, 2.42 g (0.02 mol) of thionyl chloride and 3.33 g (0.025 mol) of AlCl$_3$ are used. Yield 58%

MS m/z (%): 274/272 (35/100, M$^+$), 259/257 ((5/17, M$^+$-CH$_3$), 243, 241 (19/21, M$^+$-OCH$_3$), 208 (29), 194 (17), 178 (23, 208-CO), 165 (49).

H$_1$-NMR (DMSO-d6) δ in ppm: 3.09 (s, 4H, —CH$_2$—CH$_2$), 3.77 (s, 3H, —OCH$_3$), 7.06 (dd, 1H, J$_1$=2.8 Hz, J$_2$=8.4 Hz, C$^8$—H), 7.25 (d, 1H, J=8.4 Hz, C$^3$—H), 7.38-7.45 (m, 3H, C$^1$—H, C$^6$—H, C$^9$—H), 7.85 (d, 1H, J=8.3, C$^4$—H).

EXAMPLE 12

2-Amino-7-methoxydibenzosuberone (9a)

4.0 g (0.0135 mol) of 2-acetamido-7-methoxydibenzosuberone are suspended in 100 ml of 20% strength HCl and the reaction mixture is heated under reflux for 5 hours.
On cooling, a precipitate arises, which is filtered off. After drying in vacuo, a sand-colored powder is obtained.
Yield: 1.85 g (0.0073 mol) (54.0%; melting point: 185.3° C.

MS m/z (%): 253 (100, M$^+$), 238 (51, M$^+$-CH$_3$), 224 (41, 238-NH), 210 (14), 194 (12), 180 (13), 165 (13), 152 (6).

H$_1$-NMR 2.96 (s, 4H, —CH$_2$—CH$_2$), 3.75 (s, 3H, —OCH$_3$), 6.06 (s, 2H, —NH$_2$), 6.34 (s, 1H, C$^1$—H), 6.49 (d, 1H, J=8.7 Hz, C$^3$—H), 7.00 (d, 1H, J=8.3 Hz, C$^8$—H), 7.19 (d, 1H, J=8.3 Hz, C$^9$—H), 7.36 (s, 1H, C$^6$—H), 7.87 (d, 1H, J=8.7 Hz, C$^4$—H).

EXAMPLE 13

2-Chloro-7-hydroxydibenzosuberone (12)

0.13 ml (1.34 mmol) of boron tribromide is added dropwise to a solution of 1.0 g (2.67 mmol) of 2-chloro-7-methoxydibenzosuberone in 10 ml of MC under an argon inert gas atmosphere at room temperature. The reaction mixture is stirred at room temperature for 6 h, 20 ml of water are then added and the org. phase is concentrated in vacuo. The product is obtained in the form of an orange solid.
Yield: 0.66 g (95%); melting point: 191.6° C.

IR (ATR) 2926, 1589 (C=O), 1561, 1459, 1422, 1363, 1312, 1160, 1080, 1006, 837, 798.

H$_1$-NMR (DMSO-d6) δ in ppm: 3.05 (dd, 4H, J$_1$=9.0, J$_2$=13.5, —CH$_2$—CH$_2$—), 6.91 (d, 1H, J=8.2, C$^8$—H), 7.13 (d, 1H, J=8.3, C$^9$—H), 7.30-7.80 (m, 3H, C$^1$—H, C$^3$—H, C$^6$—H), 7.82 (d, 1H, J=9.1, C$^4$—H).

$^{13}$C-NMR (DMSO-d6) δ in ppm: 33.4 (C$^{11}$), 34.4 (C$^{10}$), 116.2 (C$^6$), 120.7 (C$^8$), 126.9 (C$^3$), 129.3 (C$^1$), 131.5 (C$^9$), 132.5 (C$^4$), 133.1 (C$^{4a}$), 137.1 (C$^{5a}$), 137.3 (C$^{9a}$), 138.5 (C$^2$), 144.7 (C$^{11a}$), 156.1 (C$^7$), 193.5 (C$^5$).

EXAMPLE 14

2-Chloro-7-(S-1,2-isopropylideneglycer-3-yl)-10,11-dihydrodibenzo[a,d]cyclohepten-5-one (13a)

The preparation of the title compound is carried out by method E. Yield: 89%
C$_{21}$H$_{21}$ClO$_4$ (Mr=372.85)
MS m/z (%): 374/372 (15/43, M$^+$), 359/357 (6/17), 299/297 (26/76), 273/271 (5/13), 260/258 (4/10), 194 (11), 178 (24), 165 (37), 145 (24), 115 (46), 101 (100), 73 (16), 59 (16).

$^1$H-NMR (DMSO-d6) δ in ppm: 1.29 (s, 3H, —CH$_3$), 1.34 (s, 3H, —CH$_3$), 3.06 (s, 4H, —CH$_2$—CH$_2$—), 3.73-3.80 (m, 1H, —OCH$_2$—), 4.03-4.12 (m, 3H, —CH$_2$O—, —OCH$_2$—), 4.37-4.42 (m, 1H, —CH—), 7.13 (d, 1H, J=8.3, C$^8$—H), 7.27 (d, 1H, J=8.4, C$^9$—H), 7.39-7.47 (m, 3H, C$^1$—H, C$^3$—H, C$^6$—H), 7.85 (d, 1H, J=8.3, C$^4$—H).

$^{13}$C-NMR (DMSO-d6) δ in ppm: 25.8 (—CH$_3$), 26.9 (—CH$_3$), 33.3 (C$^{11}$), 34.4 (C$^{10}$), 66.0 (—OCH$_2$—), 69.3 (—CH$_2$O—), 74.0 (—CH—), 115.0 (C$^6$), 120.3 (C$^8$), 127.0 (C$^3$), 129.5 (C$^1$), 131.6 (C$^9$), 132.6 (C$^4$), 135.1 (C$^{4a}$), 136.9 (C$^{5a}$), 137.5 (C$^{9a}$), 138.6 (C$^2$), 144.8 (C$^{11a}$), 157.3 (C$^7$), 193.2 (C$^5$).

EXAMPLE 15

2-Chloro-7-(R-1,2-isopropylideneglycer-3-yl)-10,11-dihydrodibenzo[a,d]cyclohepten-5-one (13b)

The preparation of the title compound is carried out by method E. Yield: 91%
C$_{21}$H$_{21}$ClO$_4$ (Mr=372.85); GC 24.6 min
MS m/z (%): 374/372 (16/45, M$^+$), 359/357 (6/17), 299/297 (26/76), 273/271 (5/13), 260/258 (4/11), 194 (12), 178 (26), 165 (39), 145 (25), 115 (46), 101 (100), 73 (14), 59 (14).

$^1$H-NMR (DMSO-d6) δ in ppm: 1.29 (s, 3H, —CH$_3$), 1.34 (s, 3H, —CH$_3$), 3.10 (s, 4H, —CH$_2$—CH$_2$—), 3.72-3.80 (m, 1H, —CH$_2$O—), 4.03-4.09 (m, 3H, —CH$_2$O—, —OCH$_2$—), 4.31-4.46 (m, 1H, —CH—), 7.13 (d, 1H, J=8.6 C$^8$—H), 7.27 (d, 1H, J=8.5, C$^9$—H), 7.39-7.49 (m, 3H, C$^1$—H, C$^3$—H, C$^6$—H), 7.85 (d, 1H, J=7.4, C$^4$—H).

$^{13}$C-NMR (DMSO-d6) δ in ppm: 25.7 (—CH$_3$), 26.9 (—CH$_3$), 33.3 (C$^{11}$), 34.3 (C$^{10}$), 660 (—CH$_2$O—), 69.3 (—OCH$_2$—), 74.0 (—CH—), 115.0 (C$^6$), 120.2 (C$^8$), 127.0

($C^3$), 129.5 ($C^1$), 131.6 ($C^9$), 132.6 ($C^4$), 135.1 ($C^{4a}$), 136.9 ($C^{5a}$), 137.5 ($C^{9a}$), 138.6 ($C^2$), 144.7 ($C^{11a}$), 157.3 ($C^7$), 193.1 ($C^5$).

EXAMPLE 16

2-Chloro-7-(3-acetoxypropoxy)-10,11-dihydrodibenzo[a,d]-cyclohepten-5-one (13h)

The preparation of the title compound is carried out by method G using 3-iodopropyl acetate as the educt in DMF as the solvent. Yield: 87%

$C_{20}H_{19}ClO_4$(Mr=358.83); GC 24.2 min

MS m/z (%): 360/358 (2/6, M$^+$), 259/257 (2/5, M$^+$-acetoxypropyl), 243/241 (2/2, M$^+$-acetoxypropoxy), 194 (9, 243/241-Cl), 178 (6), 165 (17), 101 (100, acetoxypropyl), 73 (11).

$^1$H-NMR (DMSO-d6) δ in ppm: 1.96-2.08 (m, 5H, $CH_3$—Ac, —$CH_2$—), 3.04-3.13 (m, 4H, —$CH_2$—$CH_2$—), 4.01-4.18 (m, 4H, —$OCH_2$—, —$CH_2O$—), 7.10 (d, 1H, J=8.3, $C^8$—H), 7.25 (d, 1H, J=8.4, $C^9$—H), 7.30-7.45 (m, 3H, $C^1$—H, $C^3$—H, $C^6$—H), 7.57 (d, 1H, J=8.3, $C^4$—H).

$^{13}$C-NMR (DMSO-d6) δ in ppm: 21.0 ($CH_3$Ac—), 28.4 (—$CH_2$—), 33.6 ($C^{11}$), 34.3 ($C^{10}$), 61.1 (AcO—$CH_2$—), 64.8 (—$OCH_2$), 114.9 ($C^6$), 120.3 ($C^8$), 127.6 ($C^3$), 130.3 ($C^1$), 131.6 ($C^9$), 132.6 ($C^4$), 135.0 ($C^{4a}$), 136.9 ($C^{5a}$), 137.5 ($C^{9a}$), 138.5 ($C^2$), 144.7 ($C^{11a}$), 157.3 ($C^7$), 170.7 (C=O), 193.1 ($C^5$).

EXAMPLE 17

2-Chloro-7-(3-acetoxyethoxy)-10,11-dihydrodibenzo[a,d]-cyclohepten-5-one (13g)

The preparation of the title compound is carried out by method G using 3-iodoethyl acetate as the educt and DMF as the solvent. Yield: 78%

$C_{19}H_{17}ClO_4$ (Mr=344.80); GC 21.1 min

MS m/z (%): 346/344 (2/4, M$^+$), 194 (5, 241/243-Cl), 178 (8), 165 (11), 87 (100, acetoxyethyl).

$^1$H-NMR (DMSO-d6) δ in ppm: 2.03 (s, 3H, —$COCH_3$), 3.10 (s, 4H, —$CH_2$—$CH_2$—), 4.19-4.23 (m, 2H, —$OCH_2$—), 4.30-4.35 (m, 2H, —$CH_2$—O—); 7.11-7.48 (m, 5H, $C^1$—H, $C^3$—H, $C^6$—H, $C^8$—H, $C^9$—H), 7.86 (d, 1H, J=8.3, $C^4$—H).

$^{13}$C-NMR (DMSO-d6) δ in ppm: 21.0 ($CH_3$—CO—), 33.3 ($C^{11}$), 34.3 ($C^{10}$), 62.8 (AcO—$CH_2$—), 66.4 (—$CH_2O$—), 115.0 ($C^6$), 120.3 ($C^8$), 127.0 ($C^3$), 129.5 ($C^1$), 131.6 ($C^9$), 132.6 ($C^4$), 135.2 ($C^{11a}$), 136.9 ($C^{5a}$), 137.5 ($C^{9a}$), 138.6 ($C^2$), 144.8 ($C^{4a}$), 157.1 $C^7$), 170.7 (C=O), 193.1 ($C^5$).

EXAMPLE 18

2-Chloro-7-(2-morpholin-4-yl-ethoxy)-10,11-dihydrodibenzo[a,d]-cyclohepten-5-one (13c)

The preparation of the title compound is carried out by method G using 2-chloroethylmorpholine hydrochloride as the educt in acetonitrile as the solvent.

$C_{21}H_{22}ClNO_3$ (Mr=371.87); GC 32.7 min

MS m/z (%): 373/371 (1/2, M$^+$), 330/328 (2/6), 286/284 (2/6, M$^+$-morpholin-4-yl), 178 (6), 165 (4) 100 (100, morphin-4-yl-methyl).

$^1$H-NMR (DMSO-d6) δ in ppm: 3.11 (s, 4H, —$CH_2$—$CH_2$), 3.20-3.53 (m, 6H, —N—$CH_2$, —$CH_2$—N—$CH_2$—), 3.79-4.06 (m, 4H, —$CH_2$—O—$CH_2$—), 4.47-4.50 (m, 2H, (—$OCH_2$—), 7.19 (d, 1H, J=8.3, $C^8$—H), 7.32 (d, 1H, J=8.4, $C^9$—H), 7.40-7.47 (m, 3H, $C^1$—H, $C^3$—H, $C^6$—H), 7.86 (d, 1H, J=8.4, $C^4$—H), 11.57 (s, 1H, —NH—).

$^{13}$C-NMR (DMSO-d6) δ in ppm: 33.3 ($C^{11}$), 34.4 ($C^{10}$), 57.0 (—$CH_2$—O—$CH_2$—), 60.1 (—N—$CH_2$—), 65.5 (—$OCH_2$—), 66.1 (—$CH_2$—O—$CH_2$), 115.1 ($C^6$), 120.3 ($C^8$), 127.0 ($C^3$), 129.5 ($C^1$), 131.6 ($C^9$), 132.6 ($C^4$), 135.0 ($C^{4a}$), 136.9 ($C^{5a}$), 137.5 ($C^{9a}$), 138.6 ($C^2$), 144.7 ($C^{11a}$), 157.2 ($C^7$), 193.2 ($C^5$).

EXAMPLE 19

2-Chloro-7-(2-tetrahydropyran-4-yl-oxy)-10,11-dihydrodibenzo[a,d]-cyclohepten-5-one (13i)

The preparation of the title compound is carried out by method F. Yield: 46%

$C_{20}H_{19}ClN_3$ (Mr=342.83)

$^1$H-NMR (DMSO-d6) δ in ppm: 1.54-1.61 (m, 2H, —$CH_2$—), 1.91-1.98 (m, 2H, —$CH_2$—), 3.06-3.16 (m, 4H, —$CH_2$—$CH_2$—), 3.42-3.54 (m, 2H, —$CH_2O$—), 3.78-3.86 (m, 2H, —$CH_2O$—), 4.56-4.62 (m, 1H, —CH—), 7.16 (d, 1H, J=8.4, $C^8$—H), 7.27 (d, J=8.4, $C^9$—H), 7.38-7.48 (m, 3H, $C^1$—H, $C^3$—H, $C^6$—H), 7.86 (d, 1H, J=8.4 ($C^4$—H).

EXAMPLE 20

2-(2-Aminoanilino)-7-methoxydibenzosuberone (10a)

For the preparation of compound 10a by method C, 0.5 g (1.8 mmol) of 2-chloro-7-methoxydibenzosuberone, 1.0 (9.2 mmol) g of 1,2-phenylenediamine, 0.05 g of Pd(OAc)$_2$, 0.10 g of 2-(dicyclohexylphosphino)-2'-,4'-,6'-triisopropyl-biphenyl, 0.70 g of KO-tert-Bu, 5 ml of toluene and 1 ml of tert-BuOH are used. Yield: 0.48 g (78%); m.p.: 106.5° C.

$C_{22}H_{20}N_2O_2$ (Mr=344.42); GC 49.4 min

MS m/z (%): 344 (100, M$^+$), 329 (8), 315 (6), 301 (5), 195 (7), 165 (6), 107 (9).

IR 3418-3343 (C—H)$_{arom}$, 3320 (N—H), 2976-2939 (C—H)$_{aliph}$, 1546 (C=O), 1516, 1494, 1323, 1284, 1147, 1026, 828, 751, 740.

$^1$H-NMR (DMSO-d6) δ in ppm: 2.96 (s, 4H, —$CH_2$—$CH_2$), 3.76 (s, 3H, —$OCH_3$), 4.84 (s, 2H, —$NH_2$), 6.46 (s, 1H, $C^1$—H), 6.54-6.64 (m, 2H, $C^{3'}$—H, $C^{6'}$—H), 4.78 (d, 1H, J=7.8 Hz, $C^{4'}$—H), 6.91-7.04 (m, 3H, $C^3$—H, $C^5$—H, $C^8$—H), 7.20 (d, 1H, J=8.3 Hz, $C^9$—H), 7.39 (s, 1H, $C^6$—H), 7.92-7.97 (m, 2H, $C^4$—H, —NH—).

$^{13}$C-NMR (DMSO-d6) δ in ppm: 33.6 ($C^{10}$), 36.6 ($C^{11}$), 55.5 (—$OCH_3$), 112.1 ($C^6$), 113.1 ($C^3$), 114.8 ($C^1$), 115.8 ($C^{3'}$), 116.8 ($C^{4'}$), 118.3 ($C^8$), 125.2 ($C^{5'}$), 126.2 ($C^{6'}$), 126.3 ($C^{1'}$), 126.4 ($C^{4a}$), 130.4 ($C^9$), 133.9 ($C^{5a}$), 134.5 ($C^4$), 140.3 ($C^{9a}$), 144.0 ($C^{2'}$), 145.7 ($C^{11a}$), 151.1 ($C^2$). 158.0 ($C^7$), 190.3 ($C^5$).

EXAMPLE 21

2-(2-Amino-4-fluoroanilino)-7-methoxydibenzosuberone (10b)

For the preparation of compound 10b by method C, 0.5 g (1.8 mmol) of 2-chloro-7-methoxydibenzosuberone, 0.3 g (1.9 mmol) of 2-nitro-4-fluoroaniline, 0.05 g of Pd(OAc)$_2$, 0.10 g of 2-(dicyclohexylphosphino)-2'-,4'-,6'-triisopropyl-biphenyl, 0.70 g of KO-tert-Bu, 5 ml of toluene and 1 ml of tert-BuOH are used. Purification of the nitro compound is carried out by recrystallization with MeOH. Without further purification, 0.5 g of the nitro compound, 2.9 g of $ZnCl_2 \times 2 H_2O$ in 20 ml EtOH are reduced by method D. Yield: 0.42 g (65%); m.p.: 72.2° C.

$C_{22}H_{19}FN_2O_2$ (Mr=362.41); GC 54.1 min

MS m/z (%): 362 (100, M$^+$), 247 (7), 125 (14).

IR (ATR) 3353 (N—H), 2941-2834 (C–H)$_{aliph}$, 1622, 1567 (C=O), 1508, 1324, 1273, 1162, 839, 784.

$^1$H-NMR (DMSO-d6) δ in ppm: 2.49 (s, 4H, —CH$_2$—CH$_2$), 3.76 (s, 3H, —OCH$_3$), 5.25 (s, 2H, —NH$_2$), 6.30-6.38 (m, 2H, C$^{3'}$—H, C$^{5'}$—H), 6.51-6.58 (m, 2H, C$^3$—H, C$^{6'}$—H), 7.94-7.05 (m, 2H, C$^1$—H, C$^8$—H), 7.21 (d, 1H, J=8.3 Hz, C$^9$—H), 7.38 (s, 1H, C$^6$—H) 7.89 (s, 1H, —NH—), 7.93 (d, 1H, C$^4$—H).

$^{13}$C-NMR (DMSO-d6) δ in ppm: 33.6 (C$^{10}$), 36.5 (C$^{11}$), 55.5 (—OCH$_3$), 101.4 (d, J=25.5 Hz, C$^{3'}$), 102.5 (d, J=22.6 Hz, C$^{5'}$), 111.9 (C$^6$), 112.9 (C$^3$), 114.8 (C$^1$), 118.4 (C$^8$), 121.3 (d, J=2.3 Hz, C$^{1'}$), 126.2 (C$^{4a}$), 128.4 (d, J=20.8 Hz, C$^{6'}$), 130.4 (C$^9$), 134.0 (C$^{5a}$), 134.5 (C$^4$), 140.3 (C$^{9a}$), 145.8 (C$^{11a}$), 146.5 (d, J=12.0 Hz, C$^{2'}$), 151.5 (C$^2$), 158.0 (C$^7$), 161.2 (d, J=238.6 Hz, C$^{4'}$), 190.2 (C$^5$).

EXAMPLE 22

2-(2,4-Difluoroanilino)-7-methoxydibenzosuberone (10c)

For the preparation of compound 10c by method C, 0.5 g (1.8 mmol) of 2-chloro-7-methoxydibenzosuberone, 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g of KO-tert-Bu, 5 ml of toluene and 1 ml of tert-BuOH are used. Yield: 0.57 g (87%);

m.p.: 123-126° C. (decomposition); $C_{22}H_{17}F_2NO_2$ (Mr=365.38); GC 31.4 min MS m/z (%): 365 (100, M$^+$), 350 (7, M$^+$-CH$_3$), 337 (11), 322 (6), 237 (4, M$^+$-2-NH$_2$, 4-F-aniline), 208 (15), 194 (5), 178 (6), 165 (15), 152 (5).

IR (ATR) 3327 (N—H), 3074 (C—H)$_{arom}$, 2941-2842 (C—H)$_{aliph}$, 1338, 1551 (C=O), 1525, 1498, 1325, 1281, 1238, 854, 832, 786.

$^1$H-NMR (DMSO-d6) δ in ppm: 2.99 (s, 4H, —CH$_2$—CH$_2$), 3.76 8s, 3H, —OCH$_3$), 6.61 (s, 1H, C$^1$—H), 6.74 (d, 1H, J=8.7 Hz, C$^3$—H), 7.00-7.47 (m, 6H, C$^6$—H, C$^8$—H, C$^9$—H, C$^{3'}$—H, C$^{5'}$—H, C$^{6'}$—H), 7.95 (d, 1H, J=8.8 Hz, C$^4$—H), 8.55 (s, 1H, —NH—).

$^{13}$C-NMR (DMSO-d6) δ in ppm: 36.2 (C$^{10}$), 38.6 (C$^{11}$), 55.5 (—OCH$_3$), 105.3 (dd, J=26.7 Hz, C$^{3'}$), 112.2 (d, J=22.1 Hz, C$^{5'}$), 112.6 (C$^6$), 113.9 (C$^3$), 114.7 (C$^1$), 118.6 (C$^8$), 125.3 (d, J=12.2 Hz, C$^{1'}$), 126.4 (d, J=9.7 Hz, C$^{6'}$), 127.7 (C$^{4a}$), 130.6 (C$^9$), 133.8 (C$^{5a}$), 134.6 (C$^4$), 140.0 (C$^{9a}$), 145.7 (C$^{11a}$), 149.4 (C$^2$), 154.9 (d, J=143.5 Hz, C$^{4'}$), 158.1 (C$^7$), 159.8 (d, J=138.2 Hz, C$^{7'}$), 190.8 (C$^5$).

EXAMPLE 23

2-(2-Chloro-4-fluoroanilino)-7-methoxydibenzosuberone (10d)

$C_{22}H_{17}ClFNO_2$ (Mr=381.84)

For the preparation of compound 10d by method C, 0.5 g (1.8 mmol) of 2-chloro-7-methoxydibenzosuberone, 0.27 g (1.9 mmol) of 2-chloro, 4-fluoroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g of KO-tert-Bu, 5 ml of toluene and 1 ml of tert-BuOH are used. Yield: 0.24 g (35%);

m.p.: 110.2° C.; GC 38.4 min

MS m/z (%): 385/383 (36/100, M$^+$), 368/366 (2/6, M$^+$-CH$_3$), 354/352 (4/9), 340/338 (2/4), 274/272 (2/6), 237 (4, M$^+$-2-Cl, 4-F-aniline), 208 (14), 194 (5), 178 (6, 208-CO), 165 (13), 151 (4), 136 (6).

IR (ATR) 3336 (N—H), 3070 (C—H)$_{arom}$, 2939-2835 (C—H)$_{aliph}$, 1602, 1554 (C=O), 1520, 1484, 1282, 1255, 1235, 863, 818, 785.

$^1$H-NMR (DMSO-d6) δ in ppm: 3.00 (s, 4H, —CH$_2$—CH$_2$—), 3.77 (s, 3H, —OCH$_3$), 6.60 (s, 1H, C$^1$—H), 6.72 (d, 1H, J=8.8 Hz, C$^3$—H), 7.03 (d, 1H, J=5.6 Hz, C$^{6'}$—H), 7.18-7.57 (m, 5H, C$^6$—H, C$^8$—H, C$^9$—H, C$^{3'}$—H, C$^{5'}$—H), 7.94 d, 1H, J=8.7 Hz, C$^4$—H), 8.46 (s, 1H, —NH—).

$^{13}$C-NMR (DMSO-d6) δ in ppm: 33.5 (C$^{12}$), 36.2 (C$^{11}$), 55.5 (OCH$_3$), 112.8 (C$^6$), 114.1 (C$^3$), 114.6 (C$^1$), 115.6 (C$^{5'}$), 117.7 (C$^{3'}$), 118.6 (C$^8$), 127.3 (C$^{1'}$), 127.8 (C$^4$), 129.4 (C$^{2'}$), 130.6 (C$^9$), 133.7 (C$^{5a}$), 134.7 (C$^4$), 140.0 (C$^{9a}$), 145.7 (C$^{11a}$), 149.5 (C$^2$), 158.1 (C$^7$), 158.9 (C$^{4'}$), 190.8 (C$^5$).

EXAMPLE 24

2-(2,4,5-Trifluoroanilino)-7-methoxydibenzosuberone (10e)

$C_{22}H_{16}F_3NO_2$ (Mr=383.37)

For the preparation of compound 10e by method C, 0.5 g (1.8 mmol) of 2-chloro-7-methoxydibenzosuberone, 0.27 g (1.8 mmol) of 2-, 4-, 5-trifluoroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g of KO-tert-Bu, 5 ml of toluene and 1 ml of tert-BuOH are used. Yield: 0.30 g (43%);

m.p.: 132.1° C.; GC 30.0 min

MS m/z (%): 383 (100, M$^+$), 368 (8, M$^+$-CH$_3$), 355 (11), 340 (7), 237 (4, M$^+$-2,3,4-trifluoroaniline), 208 (13), 194 (5), 178 (8), 165 (13).

IR (ATR) 3337 (N—H), 3298-3016 (C—H)$_{arom}$, 2912-2846 (C—H)$_{aliph}$, 1582, 1567, 1518 (C=O), 1286, 1273, 1221, 1161, 856, 832, 808.

$^1$H-NMR (DMSO-d6) δ in ppm: 3.01 (s, 4H, —CH$_2$—CH$_2$), 3.76 (s, 3H, —OCH$_3$), 6.72 (s, 1H, C$^1$—H), 6.82-7.05 (m, 2H, C$^{3'}$—H, C$^{6'}$—H), 7.21 (d, 1H, J=8.3 Hz, C$^3$—H), 7.38-7.65 (m, 2H, C$^8$—H, C$^9$—H), 7.98 (d, 1H, J=7.98 Hz, C$^2$—H), 8.65 (s, 1H, —NH—).

$^{13}$C-NMR (DMSO-d6) δ in ppm: 33.5 (C$^{10}$), 36.1 (C$^{11}$), 55.5 (—OCH$_3$), 106.4-107.4 (m, C$^{3'}$), 111.9-112.3 (m, C$^{6'}$), 113.3 (C$^6$), 114.6 (C$^3$), 114.7 (C$^1$), 118.7 (C$^8$), 125.6-126.2 (m, C$^{1'}$), 126.2 (C$^{4a}$), 128.6 (C$^9$), 130.6 (C$^{5a}$), 133.6 (C$^4$), 134.6 (C$^{9a}$), 142.6-147.9 (m, C$^{4'}$), 143.6-148.9 (m, C$^{5'}$), 145.5 (C$^{11a}$), 148.3 (C$^2$), 148.3-153.3 (m, C$^{2'}$), 158.1 (C$^7$), 191.1 (C$^5$).

EXAMPLE 25

2-(2-Trifluoromethylanilino)-7-methoxydibenzosuberone (10f)

For the preparation of compound 10f by method C, 0.5 g (1.8 mmol) of 2-chloro-7-methoxydibenzosuberone, 0.3 g (1.9 mmol) of 2-aminotrifluoride, 0.05 g (0.22 mmol) of Pd(OAc)$_2$, 0.10 g (0.21 mmol) of 2-(dicyclohexylphosphino)-2',4',6'-triisopropyl-biphenyl, 0.70 g of KO-tert-Bu, 5 ml of toluene and 1 ml of tert-BuOH are used. Yield: 0.23 g (32%);

m.p.: 152.5° C.;

C$_{23}$H$_{18}$F$_3$NO$_2$ (Mr=397.40); GC 30.3 min

MS m/z (%): 397 (100, M$^+$), 282 (7, M$^+$-CH$_3$), 368 (12), 354 (6), 237 (5, M$^+$-2-CF$_3$-aniline), 208 (12), 194 (5),178 (6), 165 (14).

IR (ATR) 3319 (N—H), 3072-3007 (C—H)$_{arom}$, 2958-2836 (C—H)$_{aliph}$, 1550 (C=O), 1460, 1353, 1323, 1285, 1264, 1111, 1091, 1050, 692.

$^1$H-NMR (DMSO-d6) δ in ppm: 3.02 (s, 4H, —CH$_2$—CH$_2$—), 3.76 (s, 3H, —OCH$_3$), 6.91 (s, 1H, C$^1$—H), 7.01-7.06 (m, 2H, C$^3$—H, C$^{6'}$—H), 7.20-7.25 (m, 2H, C$^{2'}$—H, C$^{4'}$—H), 7.37-7.39 (m, 2H, C$^8$—H, C$^{5'}$—H), 7.47-7.52 (m, 2H, C$^6$—H, C$^9$—H), 7.98 (d, 1H, J=8.7 Hz, C$^4$—H), 9.10 (s, 1H, —NH—).

$^{13}$C-NMR (DMSO-d6) δ in ppm: 33.5 (C$^{10}$), 36.1 (C$^{11}$), 55.5 (—OCH$_3$), 114.0 (C$^6$), 114.5 (C$^3$), 114.9-117.9 (m, C$^{2'}$), 115.1 (C$^1$), 118.7 (C$^{4'}$), 121.7 (C$^{4a}$), 127.1 (C$^{11}$), 129.1 (C$^{3'}$), 129.1-132.6 (m, —CF$_3$), 130.7 (C$^9$), 133.7 (C$^{5a}$), 134.6 (C$^4$), 139.9 (C$^{9a}$), 142.7 (C$^{1'}$), 145.7 (C$^{11a}$), 147.3 (C$^2$), 158.1 (C$^7$), 191.2 (C$^5$).

EXAMPLE 26

2-(Anilino)-7-methoxydibenzosuberone (10g)

For the preparation of compound 10 g by method C, 0.5 g (1.8 mmol) of 2-chloro-7-methoxydibenzosuberone, 0.2 g (2.1 mmol) of aniline, 0.05 g (0.22 mmol) of Pd(OAc)$_2$, 0.10 g (0.21 mmol) of 2-(dicyclohexylphosphino)-2',4',6'-triisopropyl-biphenyl, 0.70 g (6.2 mmol) of KO-tert-Bu, 5 ml of toluene and 1 ml of tert-BuOH are used. Yield: 0.27 g (46%);

m.p.: 123.5° C.; C$_{22}$H$_{19}$NO$_2$ (Mr=329.40); GC 35.1 min

MS m/z (%): 329 (100, M$^+$), 314 (6, M$^+$-CH$_3$), 300 (11), 286 (5), 270 (3), 254 (3), 237 (2, M$^+$-aniline), 208 (10), 194 (4), 180 (4), 165 (11).

IR (ATR) 3329 (N—H), 2992-2853 (C—H)$_{aliph}$, 1560 (C=O), 1520, 1494, 1319, 1280, 1262, 1240, 1035, 817, 742.

$^1$H-NMR (DMSO-d6) δ in ppm: 2.99 (s, 4H, —CH$_2$—CH$_2$), 3.75 (s, 3H, —OCH$_3$), 6.93-7.05 (m, 3H, C$^3$—H, C$^{4'}$—H, C$^{6'}$—H), 7.16-7.37 (m, 5H, C$^6$—H, C$^8$—H, C$^9$—H, C$^{3'}$—H, C$^{5'}$—H), 7.95 (d, 1H, J=8.7 Hz, C$^4$—H), 8.81 (s, 1H, —NH—).

$^{13}$C-NMR (DMSO-d6) δ in ppm: 34.6 (C$^{10}$), 36.3 (C$^{11}$), 55.5 (—OCH$_3$), 113.1 (C$^6$), 114.5 (C$^3$), 114.6 (C$^1$), 118.6 (C$^8$), 120.0 (C$^{2'}$), 120.0 (C$^{6'}$), 122.5 (C$^{4'}$), 127.7 (C$^{4a}$), 129.7 (C$^{3'}$), 129.7 (C$^{5'}$), 130.6 (C$^9$), 133.9 (C$^{5a}$), 134.7 (C$^4$), 140.0 (C$^{9a}$), 141.4 (C$^{1'}$), 145.9 (C$^{11a}$), 148.6 (C$^2$), 158.9 (C$^7$), 190.9 (C$^5$).

EXAMPLE 27

2-(2-Methoxyanilino)-7-methoxydibenzosuberone (10h)

For the preparation of compound 10h by method C, 0.5 g (1.8 mmol) of 2-chloro-7-methoxydibenzosuberone, 0.25 g (2.0 mmol) of 2-methoxyaniline, 0.05 g (0.22 mmol) of Pd(OAc)$_2$, 0.10 g (0.21 mmol) of 2-(dicyclohexylphosphino)-2',4',6'-triisopropyl-biphenyl, 0.70 g of KO-tert-Bu, 5 ml of toluene and 1 ml of tert-BuOH are used. Yield: 0.55 g (85%);

m.p.: 145.0° C.;

C$_{23}$H$_{21}$NO$_3$ (Mr=359.43); GC 49.7 min

MS m/z (%): 359 (100, M$^+$), 344 (5, M$^+$-CH$_3$), 326 (2), 316 (3), 208 (3), 196 (14), 183 (16), 165 (7), 152 (2), 136 (2), 121 (5), 108 (2).

IR (ATR) 3323 (N—H), 3002 (C—H)$_{arom}$, 1956-2829 (C—H)$_{aliph}$, 1557 (C=O), 1520, 1489, 1322, 1289, 1271, 1252, 1211, 1111, 1027, 866, 754.

$^1$H-NMR (DMSO-d6) δ in ppm: 2.98 (s, 4H, —CH$_2$—CH$_2$), 3.76 (s, 3H, —OCH$_3$), 3.79 (s, 3H, —OCH$_3$), 6.71 (s, 1H, C$^1$—H), 6.83 (d, 1H, J=8.9 Hz, C$^3$—H), 6.97-7.09 (m, 3H, C$^{3'}$—H, C$^{4'}$—H, C$^{5'}$—H), 7.19-7.30 (m, 2H, C$^8$—H, C$^9$—H), 7.38 (s, 1H, C$^6$—H), 7.93 (d, 1H, J=8.8 Hz, C$^4$—H), 8.17 (s, 1H, —NH—).

$^{13}$C-NMR (DMSO-d6) δ in ppm: 33.6 (C$^{10}$), 36.4 (C$^{11}$), 55.5 (—OCH$_3$), 55.8 (—OCH$_3$), 112.4 (C$^6$), 112.8 (C$^3$), 114.1 (C$^{3'}$), 114.7 (C$^1$), 118.4 (C$^8$), 121.0 (C$^{4'}$), 122.7 (C$^{6'}$), 124.6 (C$^{5'}$), 127.1 (C$^{4a}$), 129.6 (C$^{1'}$), 130.5 (C$^9$), 133.7 (C$^{5a}$), 134.5 (C$^4$), 140.2 (C$^{9a}$), 145.6 (C$^{11a}$), 149.7 (C$^{2'}$), 152.3 (C$^2$), 158.0 (C$^7$), 190.6 (C$^5$).

EXAMPLE 28

2-(3-Methyl-4-fluoroanilino)-7-methoxydibenzosuberone (10i)

For the preparation of compound 10i by method C, 0.5 g (1.8 mmol) of 2-chloro-7-methoxydibenzosuberone, 0.25 g (2.0 mmol) of 3-methyl, 4-fluoroaniline, 0.05 g (0.22 mmol) of Pd(OAc)$_2$, 0.10 g (0.21 mmol) of 2-(dicyclohexylphosphino)-2',4',6'-triisopropyl-biphenyl, 0.70 g of KO-tert-Bu, 5 ml of toluene and 1 ml of tert-BuOH are used. Yield: 0.51 g (78%);

m.p.: 158.9° C.; C$_{23}$H$_{20}$FNO$_2$ (Mr=361.42); GC 39.8 min

MS m/z (%): 361 (100, M$^+$), 346 (6, M$^+$-CH$_3$), 333 (9), 237 (2, M$^+$-3-CH$_3$, 4-F-aniline), 208 (10), 178 (3), 165 (10).

IR (ATR) 3363 (N—H), 3013 (C—H)$_{arom}$, 2934-2838 (C—H)$_{aliph}$, 1582, 1561 (C=O), 1501, 1286, 1270, 1210, 1048, 971, 862, 806, 768.

$^1$H-NMR (DMSO-d6) δ in ppm: 2.21 (s, 3H, —CH$_3$), 3.00 (s, 4H, —CH$_2$—CH$_2$), 3.77 (s, 3H, —OCH$_3$), 6.75 (s, 1H, C$^1$—H), 6.89 (d, 1H, J=8.8 Hz, C$^3$—H), 7.00-7.14 (m, 4H, C$^8$—H, C$^9$—H, C$^{5'}$—H, C$^{6'}$—H), 7.22 (d, 1H, J=8.3 Hz, C$^{2'}$—H), 7.39 (s, 1H, C$^6$—H) 7.96 (d, 2H, J=8.8 Hz, C$^4$—H), 8.69 (s, 1H, —NH—).

$^{13}$C-NMR (DMSO-d6) δ in ppm: 14.7 (—CH$_3$), 33.5 (C$^{10}$), 36.3 (C$^{11}$), 55.7 (—OCH$_3$), 112.6 (C$^6$), 114.0 (C$^3$), 114.7 (C$^1$), 115.9 (C$^{5'}$), 118.5 (C$^8$), 119.9 (C$^{2'}$), 123.8 (C$^{6'}$), 125.4 (C$^{3'}$), 127.4 (C$^{4a}$), 130.5 (C$^9$), 134.0 (C$^{5a}$), 134.5 (C$^4$), 137.3 (C$^{1'}$), 140.1 C$^{9a}$), 145.9 (C$^{11a}$), 149.2 (C$^2$), 156.8 (C$^{4'}$), 158.1 (C$^7$), 190.6 (C$^5$).

EXAMPLE 29

2-(2-Amino-4-trifluoromethylanilino)-7-methoxydibenzosuberone (10j)

For the preparation of compound 10j by method C, 0.5 g (1.8 mmol) of 2-chloro-7-methoxydibenzosuberone, 0.4 g (1.9 mmol) of 2-nitro-4-trifluoromethylaniline, 0.05 g of Pd(OAc)$_2$, 0.10 g of 2-(dicyclohexylphosphino)-2'-,4'-,6'-triisopropyl-biphenyl, 0.70 g of KO-tert-Bu, 5 ml of toluene and 1 ml of tert-BuOH are used. Purification of the nitro compound is carried out by recrystallization with MeOH. Without further purification, 0.5 g of the nitro compound, 2.9 g of ZnCl$_2$×2 H$_2$O in 20 ml EtOH are reduced by method D. M.p.: 78.9° C.;

GC: 50.8 min;

C$_{23}$H$_{19}$F$_3$N$_2$O$_2$ (Mr=412.42)

MS m/z (%): 412 (100, M$^+$), 397 (8, M$^+$-CH$_3$), 383 (4), 369 (6), 263 (6), 237 (M$^+$-2-NH$_2$, 4-CF$_3$-aniline), 208 (4), 192 (4), 175 (13).

IR (ATR): 3344 (N—H), 2943 (C—H)$_{aliph}$, 1567 (C=O), 1520, 1496, 1333, 1283, 1260, 1213, 1162, 1147, 1112, 1036.

$^1$H-NMR (DMSO-d6) δ in ppm: 3.00 (s, 4H, —CH$_2$—CH$_2$—), 3.77 (s, 3H, —OCH$_3$), 5.33 (s, 2H, —NH$_2$), 6.62 (s, 1H, C$^1$—H), 6.76 (d, 1H, J=8.8 Hz, C$^3$—H), 6.85 (d, 1H, J=8.1 Hz, C$^{6'}$—H), 7.01-7.06 (m, 2H, C$^{3'}$—H, C$^{5'}$—H), 7.25-7.21 (m, 2H, C$^8$—H, C$^9$—H), 7.39 (s, 1H, C$^6$—H), 7.95 (d, 1H, J=8.7 Hz, C$^4$—H), 8.09 (s, 1H, —NH—).

$^{13}$C-NMR (DMSO-d6) δ in ppm: 33.6 (C$^{10}$), 36.3 (C$^{11}$), 55.5 (—OCH$_3$), 111.7 (C$^{3'}$), 123.2 (C$^{5'}$) 113.1 (C$^6$), 114.3 (C$^3$), 114.7 (C$^1$), 118.6 (C$^8$), 125.5 (—CF$_3$), 124.0 (C$^{6'}$), 125.8 (C$^{4'}$), 127.5 (C$^{4a}$), 129.3 (C$^{2'}$), 130.6 (C$^9$), 133.8 (C$^{5a}$), 134.6 (C$^4$), 140.1 (C$^{9a}$), 143.2 (C$^{1'}$), 145.7 (C$^{11a}$), 149.4 (C$^2$), 158.1 (C$^7$), 190.7 (C$^5$).

EXAMPLE 30

2-(Phenyl)-7-methoxydibenzosuberone (10k)

A mixture of 0.137 g (0.50 mmol) of 2-chloro-7-methoxy-dibenzosuberone, 0.092 mg (0.75 mmol) of phenylboronic acid, 2.2 mg (2 mol %) of Pd(OAc), 0.138 g (1.0 mol) of K$_2$CO$_3$, 4.0 g of PEG-400 are stirred at 45° C. for 5 h, until a complete reaction is observed on the TLC. 15 ml of NaOH are added to the mixture and the mixture is extracted 4× with 15 ml of diethyl ether each time. Concentration is carried out in vacuo. Purification is carried out via flash chromatography (SiO$_2$, hexane/ethyl acetate 9+1). Yield: 0.05 g (32%); m.p.: 97.8° C.;

C$_{22}$H$_{18}$O$_2$ (Mr=314.39); GC 24.7 min

MS m/z (%): 314 (100, M$^+$); 299 (11, M$^+$-CH$_3$), 285 (20), 271 (11), 255 12), 239 (11), 228 (6), 215 (5), 178 (4), 165 (10), 120 (4).

IR (ATR) 3027 (C—H)$_{arom}$, 2993-2834 (C—H)$_{aliph}$, 1640, 1601 (C=O), 1493, 1287 (C—O), 1245, 1048, 977, 805, 770, 701.

$^1$H-NMR (DMSO-d6) δ in ppm: 2.47-2.51 (m, 4H, —CH$_2$—CH$_2$), 3.78 (s, 3H, —OCH$_3$), 7.08-7.12 (m, 1H, C$^{4'}$—H), 7.26 (d, 1H, J=8.4 Hz, C$^3$—H), 7.40-7.48 (m, 4H, C$^1$—H, C$^6$—H, C$^8$—H, C$^9$—H), 7.64 (m, 4H, C$^{2'}$—H, C$^{3'}$—H, C$^{5'}$H, C$^{6'}$—H), 7.97 (d, 1H, J=8.8 Hz, C$^2$—H).

$^{13}$C-NMR (DMSO-d6) δ in ppm: 33.6 (C$^{10}$), 35.0 (C$^{11}$), 55.6 (—OCH$_3$), 114.2 (C$^6$), 119.5 (C$^8$), 125.0 (C$^3$), 127.3 (C$^{6'}$), 127.3 (C$^{2'}$), 128.1 (C$^{4'}$), 128.7 (C$^9$), 129.4 (C$^{5'}$), 129.4 (C$^{3'}$), 131.4 (C$^1$), 131.5 (C$^4$), 134.9 (C$^{4a}$), 136.9 (C$^{5a}$), 139.1 (C$^{9a}$), 139.1 (C$^{1'}$), 143.4 (C$^2$), 144.3 (C$^{11a}$), 158.1 (C$^7$), 193.7 (C$^5$).

EXAMPLE 31

2-(2,4-Difluoroanilino)-7-methoxydibenzosuberenone (101)

For the preparation of compound 101 by method C, 0.5 g (1.8 mmol) of 2-chloro-7-methoxydibenzosuberenone, 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g of KO-tert-Bu, 5 ml of toluene and 1 ml of tert-BuOH are used. Yield: 0.53 g (81%);

m.p.: 202.4° C.; C$_{22}$H$_{15}$F$_2$NO$_2$ (Mr=363.37); GC 36.2 min

MS m/z (%): 363 (100, M$^+$), 335 (52), 292 (48), 272 (6), 152 (13), 13), 145 (10), 136 (5).

IR (ATR) 3313 (N—H), 3098-3018 (C—H)$_{arom}$, 2923-2851 (C—H)$_{aliph}$, 1611, 1566 (C=O), 1531, 1498, 1360, 1345, 1280, 1259, 1096, 847, 834

$^1$H-NMR (DMSO-d6) δ in ppm: 3.87 (s, 3H, —OCH$_3$), 6.86-6.92 (m, 2H, C$^1$—H, C$^3$—H), 6.99-7.11 (m, 3H, C$^{3'}$—H, C$^{5'}$—H, C$^{6'}$—H), 7.28-7.47 (m, 3H, C$^8$—H, C$^{10}$—H, C$^{11}$—H), 7.63-7.72 (m, 2H, C$^6$—H, C$^9$—H), 8.11 (d, 2H, C$^4$—H), 8.65 (s, 1H, —NH).

$^{13}$C-NMR (DMSO-d6) δ in ppm: 55.8 (—OCH$_3$), 105.4 (dd, J=24.1 Hz, C$^{3'}$) 112.2 (d, J=25.7 Hz, C$^{5'}$), 113.1 (C$^6$), 114.0 (C$^1$), 115.9 (C$^3$), 119.9 (C$^8$), 125.3 (d, J=12.1, C$^{1'}$), 126.3 (d, J=9.7 Hz, C$^{6'}$), 128.6 (C$^{4a}$), 128.7 (C$^{5a}$), 130.0 (C$^{10}$), 131.7 (C$^{11}$), 133.1 (C$^9$), 134.2 (C$^4$), 137.6 (C$^{9a}$), 139.7 (C$^{11a}$), 149.1 (C$^2$), 155.0 (d, J=163.7 Hz, C$^{4'}$) 160.0 (d, J=163.7 Hz, C$^{2'}$), 160.0 (C$^7$), 188.1 (C$^5$).

EXAMPLE 32

2-(2,4-Difluoroanilino)-7-(S-1,2-isopropylideneglycer-3-yl)-10,11-dihydrodibenzo[a,d]-cyclohepten-5-one (14a)

For the preparation of the compound by method C, 0.67 g (1.8 mmol) of 2-chloro-7-(S-1,2-isopropylideneglycer-3-yl)-10,11-dihydrodibenzo[a,d]-cyclohepten-5-one, 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2'-, 4'-,6'-triisopropyl-biphenyl, 0.70 g (6.2 mmol) of KOt-Bu, 5 ml of toluene and 1 ml of t-BuOH are used. Yield: 0.57 g (68%); m.p.: 114.6° C.;

C$_{27}$H$_{25}$F$_2$O$_4$ (Mr=465.50); GC 76.6 min

MS m/z (%): 465 (100, M$^+$), 450 (6, M$^+$-CH$_3$), 390 (36), 364 (42), 351, (40), 35 (7), 323 (11), 178 (38), 165 (16), 115 (13), 101 (31).

IR (ATR) 3352 (N—H), 2997-2944 (C—H)$_{aliph}$, 1560, 1509 (C=O), 1289, 1262, 1140, 843, 814, 802

$^1$H-NMR (DMSO-d6) δ in ppm: 1.29 (s, 3H, —CH$_3$), 1.34 (s, 3H, —CH$_3$), 3.31 (s, 4H, —CH$_2$—CH$_2$), 3.72-4.45 (m, 5H, —OCH$_2$—, —CH—, —CH$_2$O—), 6.60 (s, 1H, C$^1$—H), 6.73 (d, 1H, J=9.3, C$^3$—H), 7.00-7.47 (m, 6H, C$^6$—H, C$^8$—H, C$^9$—H), C$^{3'}$—H, C$^{5'}$—H, C$^{6'}$—H), 7.94 (d, 1H, J=8.6, C$^4$—H), 8.54 (s, 1H, —NH—).

$^{13}$C-NMR (DMSO-d6) δ in ppm: 25.8 (—CH$_3$), 26.9 (—CH$_3$), 33.5 (C$^{11}$), 36.2 (C$^{10}$), 66.0 (—CH$_2$—O—), 69.2 (—O—CH$_2$—), 74.1 (—OCH—), 105.3 (d, J=24.3 C$^{3'}$), 109.2 (—C—), 112.1 (d, J=21.9 (C$^{5'}$), 112.6 (C$^6$), 113.9 (C$^3$), 115.4 (C$^1$); 119.1 (C$^8$), 125.3 (d, J=12.0, C$^{1'}$), 126.4 (d, J=9.8, C$^{6'}$), 127.7 C$^{4a}$), 130.6 (C$^9$), 133.8 (C$^{5a}$), 134.9 (C$^4$)

140.1 ($C^{9a}$), 145.7 ($C^{11a}$), 149.5 ($C^2$), 154.5 (d, J=152.8, $C^{4'}$), 157.2 ($C^7$); 160.2 (d, J=169.5, $C^{2'}$) 190.7 ($C^5$).

EXAMPLE 33

2-(2,4-Difluoroanilino)-7-(R-1,2-isopropylideneglycer-3-yl)-10,11-dihydrodibenzo[a,d]-cyclohepten-5-one (14b)

For the preparation of the compound by method C, 0.67 g (1.8 mmol) of 2-chloro-7-7-(R-1,2-isopropylideneglycer-3-yl)-10,11-dihydrodibenzo[a,d]-cyclohepten-5-one, 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g (6.2 mmol) of KOt-Bu, 5 ml of toluene and 1 ml of t-BuOH are used. Yield: 65%; $C_{27}H_{25}F_{22}O_4$ (Mr=465.50)

EXAMPLE 34

2-(Aminoanilino)-7-(S-1,2-isopropylideneglycer-3-yl)-10,11-dihydrodibenzo[a,d]-cyclohepten-5-one (14c)

For the preparation of the compound by method C, 0.67 g (1.8 mmol) of 2-chloro-7-7-(S-1,2-isopropylideneglycer-3-yl)-10,11-dihydrodibenzo[a,d]-cyclohepten-5-one, 1.0 (9.2 mmol) g of 1,2-phenylenediamine, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g (6.2 mmol) of KOt-Bu, 5 ml of toluene and 1 ml of t-BuOH are used. $C_{27}H_{28}N_2O_4$ (Mr=444.54)

$^1$H-NMR (DMSO-d6) δ in ppm: 1.29 (s, 3H, —CH$_3$), 1.34 (s, 3H, —CH$_3$), 2.96 (s, 4H, —CH$_2$—CH$_2$—), 3.72-3.79 (m, 1H, —CH$_2$O—), 4.01-4.31 (m, 3H, —CH$_2$O—, —CH$_2$O—), 4.37-4.42 (m, 1H, —CH—), 4.83 (s, 2H, —NH$_2$), 6.45 (s, 1H, $C^1$—H), 6.53-6.63 (m, 2H, $C^{3'}$—H, $C^{6'}$—H), 6.77 (d, 1H, J=7.4, $C^{4'}$—H), 6.90-7.05 (m, 3H, $C^3$—H, $C^8$—H, $C^{5'}$—H), 7.20 (d, 1H, J=8.4, $C^9$—H), 7.39 (s, 1H, $C^6$—H), 7.91-7.96 (m, 2H, $C^4$—H, —NH—).

$^{13}$C-NMR (DMSO-d6) δ in ppm: 25.8 (—CH$_3$), 26.9 (—CH$_3$), 33.6 ($C^{10}$), 36.6 ($C^{11}$), 66.1 ($C^3$-glyceryl), 69.2 ($C^1$-glyceryl), 74.1 ($C^2$-glyceryl), 112.1 ($C^6$), 113.1 ($C^3$), 115.5 ($C^1$), 115.8 ($C^{3'}$), 116.8 ($C^{4'}$), 118.8 ($C^8$), 125.2 ($C^{5'}$); 126.2 ($C^{6'}$), 126.2 ($C^{1'}$), 126.4 ($C^{4a}$), 130.4 ($C^9$), 133.9 ($C^{5a}$), 134.8 ($C^4$), 140.3 ($C^{9a}$), 144.0 ($C^{2'}$), 145.8 ($C^{11a}$), 151.1 ($C^2$), 157.2 ($C^7$), 190.2 ($C^5$).

EXAMPLE 35

2-(2-Aminoanilino)-7-(R-1,2-isopropylideneglycer-3-yl)-10,11-dihydrodibenzo[a,d]-cyclohepten-5-one (14d)

For the preparation of the compound by method C, 0.67 g (1.8 mmol) of 2-chloro-7-(R-1,2-isopropylideneglycer-3-yl)-10,11-dihydrodibenzo[a,d]-cyclohepten-5-one, 1.0 (9.2 mmol) g of 1,2-phenylenediamine, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g (6.2 mmol) of KOt-Bu, 5 ml of toluene and 1 ml of t-BuOH are used. Yield: 72%; $C_{27}H_{28}N_2O_4$ (Mr=444.54)

$^1$H-NMR (DMSO-d6) δ in ppm: 1.29 (s, 3H, —CH$_3$), 1.35 (s, 3H, —CH$_3$), 2.96 (s, 4H, —CH$_2$—CH$_2$—), 3.76 (q, 1H, J$_1$=6.5, J$_2$=8.1, —CH$_2$O—), 3.99-4.12 (m, 3H, —CH$_2$O—, —OCH$_2$—), 4.39 (quin, 1H, —CH—), 4.83 (s, 2H, —NH$_2$), 6.46 (s, 1H, $C^1$—H), 6.53-6.63 (m, 2H, $C^{3'}$—H, $C^{6'}$—H), 6.77 (d, 1H, J=6.99, $C^{4'}$—H), 6.92 (d, 1H, J=7.0, $C^{5'}$—H), 7.00-7.06 (m, 2H, $C^3$—H, $C^5$—H), 7.20 (d, 1H, J=8.2, $C^9$—H), 7.40 (s, 1H, $C^6$—H), 7.92-7.96 (m, 2H, $C^4$—H, —NH—).

$^{13}$C-NMR (DMSO-d6) δ in ppm: 25.8 (—CH$_3$), 26.9 (—CH$_3$), 33.6 ($C^{10}$), 36.6 ($C^{11}$), 66.1 ($C^3$-glyceryl), 69.2 ($C^1$-glyceryl), 74.1 ($C^2$-glyceryl), 112.1 ($C^6$), 113.1 ($C^3$), 115.5 ($C^1$), 115.8 ($C^{3'}$), 116.6 ($C^{4'}$), 118.8 ($C^8$), 125.2 ($C^{5'}$), 126.2 ($C^{1'}$), 126.2 ($C^{1'}$), 126.4 ($C^{4a}$), 130.4 ($C^9$), 133.9 ($C^{5a}$), 134.8 ($C^4$), 140.3 ($C^{9a}$), 144.0 ($C^{2'}$), 145.7 ($C^{11a}$), 151.1 ($C^2$), 157.2 ($C^7$), 190.2 ($C^5$).

EXAMPLE 36

2-(2,4-Difluoroanilino)-7-[2R-,3-dihydroxypropoxy]-10,11-dihydrodibenzo[a,d]-cyclohepten-5-one (14 e)

10 ml of H$_2$O and 0.25 g (1.3 mmol) of p-toluenesulfonic acid are added to a solution of 1.0 g (2.1 mmol) of 2-(2,4-difluoroanilino)-7-(S-1,2-isopropylideneglycer-3-yl)-10,11-dihydrodibenzo[a,d]-cyclohepten-5-one. in 40 ml of MeOH. The solution is heated to 50° C. under an argon inert gas atmosphere. After 6 h, the solution is cooled to room temperature and concentrated in vacuo. A yellow oil is obtained, which is dissolved again in ethyl acetate and 5% strength Na$_2$HCO$_3$ solution (50 ml). The organic phase is separated off and concentrated i. vac. The diol precipitates out as a white solid. The solid is dissolved in hexane/ethyl acetate (1:1) and the solution is stirred for 1 h. It is filtered and the filtrate is concentrated i. vac.

Yield: 0.85 g (95%); m.p.: 130.3° C.; $C_{24}H_{21}F_2NO_4$ (Mr=425.44)

IR (ATR) 3305 (N—H), 2934 (C—H)$_{aliph}$, 1629, 1607, 1569 (C=O), 1510, 1327, 1278, 1218, 1097, 847, 781.

$^1$H-NMR (DMSO-d6) δ in ppm: 3.32 (s, 4H, —CH$_2$—CH$_2$), 3.40-3.46 (m, 2H, —CH$_2$OH), 3.77-4.05 (m, 3H, —CHOH—, —OCH$_2$—), 4.66 (t, 1H, J=5.7, —CH—OH), 4.94 (d, 1H, J=4.9, —CH$_2$—OH), 6.60 (s, 1H, $C^1$—H), 6.73 (d, 1H, J=8.9, $C^3$—H), 7.01-7.10 (m, 2 h, $C^{3'}$—H, $C^{6'}$—H), 7.22 (d, 1H, J=8.3, $C^{4'}$—H), 7.30-7.47 (m, 3H, $C^6$—H, $C^8$—H, $C^9$—H), 7.94 (d, 1H, J=8.8, $C^4$—H), 8.54 (s, 1H, —NH—).

$^{13}$C-NMR (DMSO-d6) δ in ppm: 33.6 ($C^{11}$), 36.3 ($C^{10}$), 63.1 (—CH$_2$—OH), 70.2 (—O—CH$_2$—), 70.3 (—OCH—), 105.3 (d, J=24.3, $C^{3'}$), 112.1 (d, J=21.9, $C^{5'}$), 112.6 ($C^6$), 113.8 ($C^3$), 115.4 ($C^1$), 119.1 ($C^8$), 125.3 (d, J=12.0, $C^{1'}$), 126.4 (d, J=9.8, $C^{6'}$), 127.7 ($C^{4a}$), 130.6 ($C^9$), 133.8 ($C^{5a}$), 134.6 ($C^4$), 139.9 ($C^{9a}$), 145.7 ($C^{11a}$), 149.4 ($C^2$), 154.5 (d, J=152.8, $C^{4'}$), 157.6 ($C^7$), 160.2 (d, J=169.5, $C^{2'}$), 190.8 ($C^5$).

EXAMPLE 37

2-(2,4-Difluoroanilino)-7-[2S-,3-dihydroxypropoxy]-10,11-dihydrodibenzo[a,d]-cyclohepten-5-one (14 f)

10 ml of H$_2$O and 0.25 g (1.3 mmol) of p-toluenesulfonic acid are added to a solution of 1.0 g (2.1 mmol) of 2-(2,4-difluoroanilino)-7-(R-1,2-isopropylideneglycer-3-yl)-10,11- dihydrodibenzo[a,d]-cyclohepten-5-one in 40 ml of MeOH. The solution is heated to 50° C. under an argon inert gas atmosphere. After 6 h, the solution is cooled to room temperature and concentrated in vacuo. A yellow oil is obtained, which is dissolved again in ethyl acetate and 5% strength $Na_2HCO_3$ solution (50 ml). The organic phase is separated off and concentrated in vacuo. The diol precipitates out as a white solid. The solid is dissolved in hexane/ethyl acetate (1:1) and the solution is stirred for 1 h. It is filtered and the filtrate is concentrated i. vac.

Yield: 95%; $C_{24}H_{21}F_2NO_4$ (Mr=425.44)

$^1$H-NMR (DMSO-d6) δ in ppm: 2.99 (s, 4H, —$CH_2$—$CH_2$—), 3.41-3.46 (m, 2H, —$CH_2O$—, —CH—), 3.77-4.03 (m, 3H, —$CH_2O$—, $CH_2OH$), 4.65 (t, 1H, J=5.7, —OH), 4.93 (d, 1H, J=4.8, —$\overline{OH}$), 6.60 (s, 1H, $C^1$—H), 6.73 (d, 1H, J=8.6, $C^3$—H), 7.01-7.41 (m, 6H, $C^6$—H, $C^8$—H, $C^9$—H, $C^{3'}$—H, $C^{5'}$—H, $C^{6'}$—H), 7.94 (d, 1H, J=8.7, $C^4$—H), 8.53 (s, 1H, —NH—).

$^{13}$C-NMR (DMSO-d6) δ in ppm: 33.6 ($C^{10}$), 36.3 ($C^{11}$), 63.1 ($C^3$-propoxy), 70.2 ($C^1$-propoxy), 70.3 ($C^2$-propoxy), 105.3 (dd, 1C, $J_1$=24.2, $J_2$=26.6, $C^{3'}$), 112.2 (dd, 1C, $J_1$=3.6, $J_2$=22.0, $C^{5'}$), 112.6 ($C^6$), 113.8 ($C^3$), 115.4 ($C^1$), 119.1 ($C^8$), 125.1-125.3 (m, 1C, $C^{1'}$), 126.4-126.6 (m, 1C, $C^{6'}$), 127.8 ($C^{4a}$), 130.6 ($C^9$), 133.8 ($C^{5a}$), 134.6 ($C^4$), 139.9 ($C^{9a}$), 145.7 ($C^{11a}$), 149.4 ($C^2$), 153.4-156.5 (m, 1C, $C^{4'}$), 157.3 ($C^7$), 158.3-161.3 (m, 1C, $C^{2'}$), 190.8 ($C^5$).

EXAMPLE 38

2-(2-Aminoanilino)-7-[2R-,3-dihydroxypropoxy]-10,11-dihydrodibenzo[a,d]-cyclohepten-5-one (14g)

10 ml of $H_2O$ and 0.50 g (2.6 mmol) of p-toluenesulfonic acid are added to a solution of 1.0 g (2.1 mmol) of 2-(2-aminoanilino)-7-(S-1,2-isopropylideneglycer-3-yl)-10,11-dihydrodibenzo[a,d]-cyclohepten-5-one in 40 ml of MeOH. The solution is heated to 50° C. under an argon inert gas atmosphere. After 6 h, the solution is cooled to room temperature and concentrated in vacuo. A yellow oil is obtained, which is dissolved again in ethyl acetate and 5% strength $Na_2HCO_3$ solution (50 ml). The organic phase is separated off and concentrated i. vac. The diol precipitates out as a white solid. The solid is dissolved in hexane/ethyl acetate (1:1) and the solution is stirred for 1 h. It is filtered and the filtrate is concentrated i. vac.

Yield: 96%; $C_{24}H_{24}N_2O_4$ (Mr=404.47)

$^1$H-NMR (DMSO-d6) δ in ppm: 2.96 (s, 4H, —$CH_2$—$CH_2$—), 3.77-3.82 (m, 2H, —$OCH_2$—, —CH—), 3.86-4.02 (m, 3H, —$OCH_2$—, —$CH_2O$—), 4.65 (t, 1H, J=5.2, —OH), 4.83 (s, 2H, —$NH_2$), 4.93 (d, 1H, J=4.5, —OH), 6.45 (s, 1H, $C^1$—H), 6.54-6.62 (m, 2H, $C^{3'}$—H, $C^{6'}$—H), 6.77 (d, 1H, J=7.2, $C^{4'}$—H), 6.90-7.03 (m, 3H, $C^3$—H, $C^8$—H, $C^{5'}$—H), 7.20 (d, 1H, J=8.0, $C^9$—H), 7.40 (s, 1H, $C^6$—H), 7.91-7.95 (m, 2H, $C^4$—H, —NH—).

$^{13}$C-NMR (DMSO-d6) δ in ppm: 33.6 ($C^{10}$), 36.6 ($C^{11}$), 63.1 ($C^3$-propoxy), 70.2 ($C^1$-propoxy), 70.3 ($C^2$-propoxy), 112.1 ($C^6$), 113.1 ($C^3$), 115.5 ($C^1$), 115.8 ($C^{3'}$), 116.8 ($C^{4'}$), 118.9 ($C^8$), 125.2 ($C^{5'}$), 126.2 ($C^{6'}$), 126.3 ($C^{1'}$), 126.4 ($C^{4a}$), 130.4 ($C^9$), 134.0 ($C^{5a}$), 134.5 ($C^4$), 140.2 ($C^{9a}$), 144.0 ($C^{2'}$), 145.8 ($C^{11a}$), 151.1 ($C^2$), 157.6 ($C^7$), 190.2 ($C^5$).

EXAMPLE 39

2-(2-Aminoanilino)-7-[2S-,3-dihydroxypropoxy]-10,11-dihydrodibenzo[a,d]-cyclohepten-5-one (14 h)

10 ml of $H_2O$ and 0.50 g (2.6 mmol) of p-toluenesulfonic acid are added to a solution of 1.0 g (2.1 mmol) of 2-(2-aminoanilino)-7-(R-1,2-isopropylideneglycer-3-yl)-10,11-dihydrodibenzo[a,d]-cyclohepten-5-one in 40 ml of MeOH. The solution is heated to 50° C. under an argon inert gas atmosphere. After 6 h, the solution is cooled to room temperature and concentrated in vacuo. A yellow oil is obtained, which is dissolved again in ethyl acetate and 5% strength $Na_2HCO_3$ solution (50 ml). The organic phase is separated off and concentrated i. vac. The diol precipitates out as a white solid. The solid is dissolved in hexane/ethyl acetate (1:1) and the solution is stirred for 1 h. It is filtered and the filtrate is concentrated i. vac.

Yield: 95%; $C_{24}H_{24}N_2O_4$ (Mr=404.47)

$^1$H-NMR (DMSO-d6) δ in ppm: 2.96 (s, 4H, —$CH_2$—$CH_2$—), 3.77-3.90 (m, 2H, —$CH_2$—O—, —CH—), 3.98-4.03 (m, 2H, $CH_2OH$, —$CH_2O$—), 4.66 (s, 1H, —OH), 4.83 (s, 2H, —$\overline{NH_2}$), 4.93 (s, 1H, —OH), 6.45 (s, 1H, $C^1$—H), 6.53-6.63 (m, 2H, $C^{3'}$—H, $C^{6'}$—H), 6.77 (d, 1H, J=7.4, $C^{4'}$—H), 6.90-7.03 (m, 3H, $C^8$—H, $C^3$—H, $C^{5'}$—H), 7.20 (d, 1H, J=8.1, $C^9$—H), 7.40 (s, 1H, $C^6$—H), 7.91-7.95, (m, 2H, $C^4$—H, —NH—).

$^{13}$C-NMR (DMSO-d6) δ in ppm: 33.6 ($C^{10}$), 36.6 ($C^{11}$), 65.3 ($C^3$-propoxy), 70.2 ($C^1$-propoxy), 70.3 ($C^2$-propoxy), 112.1 ($C^6$), 113.1 ($C^3$), 115.5 ($C^1$), 115.8 ($C^{3'}$), 116.8 ($C^{4'}$), 118.9 ($C^8$), 125.2 ($C^{5'}$), 126.2 ($C^{6'}$), 126.3 ($C^{1'}$), 126.4 ($C^{4a}$), 130.4 ($C^9$), 134.0 ($C^{5a}$), 134.5 ($C^4$), 140.2 ($C^{9}$a), 144.0 ($C^{2'}$), 145.8 ($C^{11a}$), 151.1 ($C^2$), 157.6 ($C^7$), 190.2 ($C^5$).

EXAMPLE 40

2-(2,4-Difluoroanilino)-7-(2-hydroxy-ethoxy)-10,11-dihydrodibenzo[a,d]-cyclohepten-5-one (14i)

For the preparation of the compound by method C, 0.62 g (1.8 mmol) of 2-chloro-7-(2-acetoxyethoxy)-10,11-dihydrodibenzo[a,d]-cyclohepten-5-one, 0.25 g (1.9 mmol) of 2,4-difluoroaniline, 0.05 g (0.22 mmol) of $Pd(OAc)_2$, 0.10 g (0.21 mmol) of 2-(dicyclohexylphosphino)-2'-,4'-,-6'-triisopropyl-biphenyl, 0.70 g (6.2 mmol) of KOt-Bu, 5 ml of toluene and 1 ml of t-BuOH are used. Yield: 34%; $C_{23}H_{19}F_2NO_3$ (Mr=395.41)

$^1$H-NMR (DMSO-d6) δ in ppm: 2.99 (s, 4H, —$CH_2$—$CH_2$—), 3.66-3.74 (m, 2H, —$CH_2$—OH), 3.97-4.02 (m, 2H, —$OCH_2$—), 4.85 (t, 1H, J=5.$\overline{5}$, —OH), 6.60 (s, 1H, $C^1$—H), 6.73 (d, 1H, J=8.6, $C^3$—H), 7.01-7.42 (m, 6H, $C^6$—H, $C^8$—H, $C^9$—H, $C^{3'}$—H, $C^{5'}$—H, $C^{6'}$—H), 7.94 (d, 1H, J=8.8, $C^4$—H), 8.53 (s, 1H, —NH—).

$^{13}$C-NMR (DMSO-d6) δ in ppm: 33.6 ($C^{10}$), 36.2 ($C^{11}$), 59.9 ($C^2$-ethoxy), 70.0 ($C^1$-ethoxy), 105.3 (t, 1C, J=24.2, $C^{3'}$), 112-0-112.4 (m, 1C, $C^{5'}$), 112.6 ($C^6$), 113.8 ($C^3$), 115.4 ($C^1$), 119.1 ($C^8$), 125.1-125.4 (m, 1C, $C^{1'}$), 126.3-126.5 (m, 1C, $C^{6'}$), 127.7 ($C^{4a}$), 130.6 ($C^9$), 133.8 ($C^{5a}$), 134.6 ($C^4$), 140.0 ($C^{9a}$), 145.7 ($C^{11a}$), 149.4 ($C^2$), 153.4-156.5 (m, 1C, $C^{4'}$), 149.4 ($C^7$), 158.3-161.3 (m, 1C, $C^{2'}$), 190.8 ($C^5$).

EXAMPLE 41

2-(2,4-Difluoroanilino)-7-(3-hydroxy-propoxy)-10, 11-dihydrodibenzo[a,d]-cyclohepten-5-one (14j)

For the preparation of the compound by method C, 0.65 g (1.8 mmol) of 2-chloro-7-(3-acetoxypropoxy)-10,11-dihydrodibenzo[a,d]-cyclohepten-5-one, 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g (6.2 mmol) of KOt-Bu, 5 ml of toluene and 1 ml of t-BuOH are used. Yield: 40%; $C_{24}H_{21}F_2NO_3$ (Mr=409.44)

$^1$H-NMR (DMSO-d6) δ in ppm: 1.85 (quin, 2H, J=6.3, —CH$_2$—), 2.99 (s, 4H, —CH$_2$—CH$_2$—), 3.55 (q, 2H, J=6.1, —CH$_2$—OH), 4.04 (t, 2H, J=6.4-OCH$_2$—), 4.54 (t, 1H, J=5.1, —OH), 6.60 (s, 1H, $C^1$—H), 6.73 (d, 1H, J=8.6, $C^3$—H), 7.00-7.42 (m, 6H, $C^6$—H, $C^8$—H, $C^9$—H, $C^{3'}$—H, $C^{5'}$—H, $C^{6'}$—H), 7.94 (d, 1H, J=8.8, $C^4$—H), 8.54 (s, 1H, —NH—).

$^{13}$C-NMR (DMSO-d6) δ in ppm: 32.5 ($C^2$-propoxy), 33.6 ($C^{10}$), 36.2 ($C^{11}$), 57.6 ($C^3$-propoxy), 65.1 ($C^1$-propoxy), 105.3 (t, 1C, J=24.2, $C^{3'}$), 11.9-112.4 (m, 1C, $C^{5'}$), 112.6 ($C^6$), 113.8 ($C^3$), 115.3 ($C^1$), 119.1 ($C^8$), 125.1-125.4 (m, 1C, $C^{1'}$), 126.3-126.6 (m, 1C, $C^{6'}$), 127.8 ($C^{4a}$), 130.6 ($C^9$), 133.8 ($C^{5a}$), 134.5 ($C^4$), 140.0 ($C^{9a}$), 145.7 ($C^{11a}$), 149.4 ($C^2$), 153.4-156.5 (m, 1C, $C^{4'}$), 157.5 ($C^7$), 158.3-161.3 (m, 1C, $C^{2'}$), 190.8 ($C^5$).

EXAMPLE 42

2-(2,4-Difluoroanilino)-7-(2-morpholin-4-yl-ethoxy)-10,11-dihydrodibenzo[a,d]-cyclohepten-5-one (14l)

For the preparation of the compound by method C, 0.67 g (1.8 mmol) of 2-chloro-7-(2-morpholin-4-yl-ethoxy-10,11-dihydrodibenzo[a,d]-cyclohepten-5-one, 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g (6.2 mmol) of KOt-Bu, 5 ml of toluene and 1 ml of t-BuOH are used. Yield: 76%; $C_{24}H_{21}F_2NO_4$ (Mr=425.44)

$^1$H-NMR (DMSO-d6) δ in ppm: 2.42-2.50 (m, 4H, —CH$_2$—N—CH$_2$—), 2.67 (t, 2H, —CH$_2$N—), 2.99 (s, 4H, —CH$_2$—CH$_2$—), 3.56 (t, 4H, J=4.6, —CH$_2$—O—CH$_2$—), 4.09 (t, 2H, J=5.7, —CH$_2$O—), 6.61 (s, 1H, $C^6$—H) 6.73 (d, 1H, J=8.9, $C^3$—H), 7.01-7.43 (m, 6H, $C^1$—H, $C^8$—H, $C^9$—H, $C^{3'}$—H, $C^{5'}$—H, $C^{6'}$—H), 7.94 (d, 1H, J=8.8, $C^4$—H); 8.52 (s, 1H, —NH—).

$^{13}$C-NMR (DMSO-d6) δ in ppm: 33.5 ($C^{10}$), 36.2 ($C^{11}$), 54.0 (2C, $C^2/C^6$-morpholinyl), 57.3 ($C^2$-ethoxy), 65.9 ($C^1$-ethoxy), 66.5 (2C, $C^3/C^5$-morpholinyl), 105.3 (dd, 1C, $J_1$=24.1, $J_2$=26.7, $C^3$), 111.9-112.4 (m, 1C, $C^{5'}$), 112.6 ($C^6$), 113.9 ($C^3$), 115.5 ($C^1$), 119.1 ($C^8$), 125.2-125.4 (m, 1C, $C^{1'}$), 126.3-126.5 (m, 1C, $C^{6'}$), 127.8 ($C^{4a}$), 130.6 ($C^9$), 133.8 ($C^{5a}$), 134.6 ($C^4$), 140.0 ($C^{9a}$), 145.7 ($C^{11a}$), 149.4 ($C^2$), 154.9 (dd, 1C, $J_1$=12.6, $J_2$=142.3, $C^{4'}$), 157.3 ($C^7$), 159.8 (dd, 1C, $J_1$=11.5, $J_2$=138.1, $C^{2'}$), 190.8 ($C^5$).

EXAMPLE 43

2-(2-Aminoanilino)-7-(2-morpholin-4-yl-ethoxy)-10, 11-dihydrodibenzo[a,d]-cyclohepten-5-one (14m)

For the preparation of the compound by method C, 0.67 g (1.8 mmol) of 2-chloro-7-(2-morpholin-4-yl-ethoxy)-10,11-dihydrodibenzo[a,d]-cyclohepten-5-one, 1.0 (9.2 mmol) g of 1,2-phenylenediamine, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g (6.2 mmol) of KOt-Bu, 5 ml of toluene and 1 ml of t-BuOH are used. Yield: 74%; $C_{27}H_{29}N_3O_3$ (Mr=443.55))

$^1$H-NMR (DMSO-d6) δ in ppm: 2.30-2.50 (m, 4H, —CH$_2$—N—CH$_2$—), 2.67 (t, 2H, J=5.5, —CH$_2$—N—), 2.96 (s, 4H, —CH$_2$—CH$_2$—), 3.56 (t, 4H, J=4.3, —CH$_2$—O—CH$_2$—), 4.09 (t, 2H, J=5.4, —CH$_2$O—), 4.83 (s, 2H, —NH$_2$), 6.45 (s, 1H, $C^1$—H), 6.54-6.63 (m, 2H, $C^{3'}$—H, $C^{6'}$—H), 6.77 (d, 1H, J=7.6, $C^{4'}$—H), 6.92 (d, 1H, J=7.6, $C^{5'}$—H), 6.99-7.03 (m, 2H, $C^3$—H, $C^8$—H), 7.19 (d, 1H, J=8.3, $C^9$—H), 7.38 (s, 1H, $C^6$—H), 7.91-7.95 (m, 2H, $C^4$—H, —NH—).

$^{13}$C-NMR (DMSO-d6) δ in ppm: 33.6 ($C^{10}$), 36.6 ($C^{11}$), 54.0 (2C, $C^2/C^6$-morpholinyl), 57.3 ($C^2$-ethoxy), 65.9 ($C^1$-ethoxy), 66.5 (2C, $C^3/C^5$-morpholinyl), 112.2 ($C^6$), 113.1 ($C^3$), 115.6 ($C^1$), 115.8 ($C^{3'}$), 116.8 ($C^{4'}$), 118.8 ($C^8$), 125.2 ($C^{5'}$), 126.1 ($C^{6'}$), 126.2 ($C^{1'}$), 126.4 ($C^{4a}$), 130.4 ($C^9$), 133.9 ($C^{5a}$), 134.6 ($C^4$), 140.3 ($C^{9a}$), 144.0 ($C^{2'}$), 145.7 ($C^{11a}$), 151.1 ($C^2$), 157.2 ($C^7$), 190.2 ($C^5$).

EXAMPLE 44

2-(2,4-Difluoroanilino)-7-(2-tetrahydropyran-4-yl-oxy)-10,11-dihydrodibenzo[a,d]-cyclohepten-5-one (14k)

For the preparation of the compound by method C, 0.62 g (1.8 mmol) of 2-chloro-7-(2-tetrahydropyran-4-yl-oxy)-10, 11-dihydrodibenzo[a,d]-cyclohepten-5-one, 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2'-, 4'-,6'-triisopropyl-biphenyl, 0.70 g (6.2 mmol) of KOt-Bu, 5 ml of toluene and 1 ml of t-BuOH are used. Yield: 56%; $C_{26}H_{23}F_2NO_3$ (Mr=435.47)

$^1$H-NMR (DMSO-d6) δ in ppm: 1.52-1.61 (m, 2H, $C^3/C^5$-tetrahydropyranyl), 1.92-1.98 (m, 2H, $C^3/C^5$-tetrahydropyranyl), 1.99 (s, 4H, —CH$_2$—CH$_2$), 3.41-3.53 (m, 2H, $C^2/C^6$-tetrahydropyranyl), 3.78-3.88 (m, 2H, $C^2/C^6$-tetrahydropyranyl), 4.51-4.67 (m, 1H, $C^4$-tetrahydropyranyl), 6.60 (s, 1H, $C^6$—H), 6.73 (d, 1H, J=8.8, $C^3$—H), 7.04-7.41 ($C^1$—H, $C^8$—H, $C^9$—H, $C^{3'}$—H, $C^{5'}$—H, $C^{6'}$—H), 7.94 (d, 1H, $C^4$—H), 8.53 (s, 1H, —NH—).

$^{13}$C-NMR (DMSO-d6) δ in ppm: 32.1 (2C, $C^3/C^6$-tetrahydropyranyl), 33.5 ($C^{10}$), 36.2 ($C^{11}$), 64.8 (2C, $C^2/C^6$-tetrahydropyranyl), 171.9 ($C^4$-tetrahydropyran), 105.3 (dd, 1C, $J_1$=24.2, $J_2$=26.7, $C^{3'}$), 112.2 (dd, 1C, $J_1$=3.7, $J_2$=22.1, $C^{5'}$), 112.6 ($C^6$), 113.9 ($C^3$), 117.1 ($C^1$), 120.4 ($C^8$), 125.2-125.4 (m, 1C, $C^{1'}$), 126.4 (dd, 1C, $J_1$=3.2, $J_2$=9.7, $C^{6'}$), 127.7 ($C^{4a}$), 130.6 ($C^9$), 133.8 ($C^{5a}$), 134.7 ($C^4$), 140.2 ($C^{9a}$, 145.7 ($C^{11a}$), 149.5 ($C^2$), 154.9 (dd, 1C, $J_1$=11.8, $J_2$=143.5, $C^{4'}$), 158.7 ($C^7$), 159.8 (dd, 1C, $J_1$=11.9, $J_2$=137.6, $C^{2'}$), 190.8 ($C^5$).

B. Substitution at Position 8 or 9
Method H
Bromination of the Methoxymethylbenzoic Acid The methoxymethylbenzoic acid and NBS are introduced into chlorobenzene and the reaction mixture is heated to 70° C.

Variant 1

After dropwise addition of AIBN/chlorobenzene, the mixture is stirred at 100° C. for a further 2 h 45 min. The solution is then cooled and the chlorobenzene is removed. The product is used further without further purification. The succinimide is removed in the following stage.

Variant 2

After dropwise addition of AIBN/chlorobenzene, the mixture is stirred at 70-75° C. for a further 1 h 30 min. The solution is then cooled and the chlorobenzene is removed. The product is used further without further purification. The succinimide is removed in the following stage.

Method I

Wittig reaction of the bromomethylmethoxybenzoic acid with 3-chlorobenzaldehyde Triphenylphosphine is introduced into 150 ml of MeOH, the bromomethylmethoxybenzoic acid (dissolved in MeOH) is added dropwise, while stirring, and the mixture is heated under reflux for 2 hours. NaOMe solution (30% in MeOH) is then slowly added dropwise. When the dropwise addition has ended, after waiting for a further 15 minutes 3-chlorobenzaldehyde is then added. Refluxing for 6 h follows. Thereafter, the reaction mixture is poured on to a stirred mixture of 75 g of ice and 175 ml of water. In the next step, the mixture is washed 3× with 200 ml of methylene chloride each time. The aqueous phase is then rendered strongly acid with conc. HCl, while cooling with ice. Thereafter, an oily to semi-solid precipitate forms, which can be separated off in a separating funnel. The remainder of the product is extracted with methylene chloride.

Method J
Reduction of the chlorophenylvinylmethoxybenzoic acid
Variant 1

The chlorophenylvinylmethoxybenzoic acid is dissolved in methanol, and hydrochloric acid is added. Pd/BaSO$_4$ (5%) is then added. After evacuation, the mixture is flushed with 4 l of H$_2$. The solution is stirred at room temperature under an H$_2$ atmosphere for 2 days. The charcoal is then filtered off and the mixture is concentrated in vacuo. The oil formed is transferred into a separating funnel with methylene chloride and the organic phase is washed with water. After concentration, a pale yellow oil is obtained, which crystallizes when left to stand.

Variant 2

The chlorophenylvinylmethoxybenzoic acid is dissolved in the stated solvent mixture. Pd/C (10%) is then added. After evacuation, the mixture is flushed with 4 liters of H$_2$. The solution is stirred at room temperature under an H$_2$ atmosphere (further H$_2$ flask) for 4 hours. The charcoal is then filtered off and the mixture is concentrated in vacuo.

Method K
Cyclization by Means of Friedel-Crafts Acylation

The chlorophenylethylmethoxybenzoic acid is suspended in methylene chloride (dry) and the mixture is flushed with argon. The mixture is then heated to the reflux temperature and thionyl chloride in methylene chloride is added dropwise to the solution in the course of one hour, while stirring. The mixture is then stirred again for a further hour. The reaction mixture is cooled to room temperature and anhydrous AlCl$_3$ is added in the course of 30 min. Thereafter, the reaction mixture is stirred again for a further 45 min and then poured on to a mixture of 90 g of ice and 150 ml of water, while stirring.

The hydrolysis mixture is stirred for approx. 30 min. The two phases are then separated. The organic phase is concentrated in vacuo.

Method L
Methoxy Cleavage on the Ring System

The methoxydihydrodibenzosuberenone is dissolved in glacial acetic acid, and HBr (48%, aqueous) is added. The mixture is heated at 120-130° C. for 3 h.

Variant 1

After hydrolysis with approx. 150 g of ice, the precipitate is filtered off.

Variant 2

After hydrolysis with approx. 150 g of ice, the precipitate is filtered off and, after washing with water, the residue on the filter is dissolved again in methylene chloride. The solution is then concentrated.

Method M
Formation of the Acetal

First toluene-4-sulfonic acid 2,2-dimethyl-[1,3]dioxolan-4-ylmethyl ester and then K$_2$CO$_3$ are added to a solution of the dihydrodibenzosuberenone in DMF. The reaction mixture is heated to 80° C. under argon and cooled again to room temperature after 24 h. The mixture is then taken up in 50 ml of water and extracted with ethyl acetate and the combined organic phases are washed with NaOH and dried over Na$_2$SO$_4$. The mixture is then concentrated i. vac., a brown oil being obtained, which is purified via flash (SiO$_2$, hexane/ethyl acetate). The pure acetal is obtained.

Method N
Cleavage of the Acetal

H$_2$O and p-toluenesulfonic acid are added to a solution of the acetal in MeOH. The solution is heated to 50° C. under an inert gas. After 6 h, the solution is cooled to room temperature and concentrated i. vac. A yellow oil is obtained, which is dissolved again in ethyl acetate and 5% strength Na$_2$HCO$_3$ solution (50 ml). The organic phase is separated off and concentrated i. vac.

Method O
Introduction of Radicals Via the Buchwald-Hartwig Reaction

A mixture of chlorodihydrodibenzosuberenone, Pd(OAc)$_2$, phosphine ligand (2-(dicyclohexylphosphino)-2',4',6'-triisopropylbiphenyl), NaOtert-Bu, amino substituent, toluene, tert-BuOH is stirred at 100° C. for 3-5 h. Thereafter, the mixture is cooled, taken up in 150 ml of water and extracted with diethyl ether. The combined org. phases are concentrated i. vac. and the residue is purified by column chromatography (flash; SiO$_2$; hexane/ethyl acetate).

Method P
Substitution with Alcohols

A solution of chlorohydroxydibenzodihydrodibenzosuberenone, alcohol, triphenylphosphine and THF is prepared under an inert gas. After dropwise addition of the carboxylate, the mixture is stirred at 0° C. for 1 h. The reaction is continued to the end at room temperature. Thereafter, the mixture is concentrated i. vac.

Method Q
Substitution with Alkyl Halides

A mixture of phenol, alkyl halide and K$_2$CO$_3$ is heated to 80° C. in the stated solvent, stirred for 3 h, cooled to RT and dissolved again in EA and water. The org. phase is washed with water and alkali, dried over Na$_2$SO$_4$ and concentrated i. vacuo.

Method R
Preparation of the Triflate

Tf$_2$O is slowly added to a stirred solution of the phenol in pyridine at 0° C. (ice-bath) under argon over a period of 0.5 h. The reaction mixture is stirred overnight at room temperature and extracted with EA and the organic phase is washed with 10% strength HCl and 5% strength NaHCO$_3$ solution, dried over Na$_2$SO$_4$, filtered and concentrated.

Substitution in Position 8—Compounds and Precursors

EXAMPLE 45

4-Methoxy-2-methylbenzoic acid (6)

For the synthesis of the title compound, 6.64 g (0.040 mol) of 4-methoxy-2-methylbenzoic acid, 7.1 g (0.040 mol) of NBS and 0.25 g of AIBN in 150 ml of chlorobenzene are reacted by method H (variant 2). C$_9$H$_{10}$O$_3$ (Mr=166.18)

EXAMPLE 46

2-[2-(3-Chlorophenyl)-vinyl]-4-methoxybenzoic acid (7)

For the synthesis of the title compound, 45.6 g (0.186 mol) of 2-bromomethyl-4-methoxybenzoic acid, 48.8 g (0.186 mol) of triphenylphosphine, 26.1 g (0.186 mol) of 3-chlorobenzaldehyde and 84.0 g (0.435 mol) of NaOMe (28%) in 150 ml of methanol are reacted by method I. Purification is carried out by recrystallization from methanol at 4° C.

C$_{16}$H$_{13}$ClO$_3$ (Mr=288.73)

$^1$H-NMR (DMSO-d6) δ in ppm: 3.86 (s, 3H, —OCH$_3$), 6.96 (d, 1H, J=8.78 Hz, C$^5$—H), 7.12-7.59 (m, 6H, C$^3$—H and C$^{4'}$—/C$^{5'}$—/C$^{6'}$—H and C$^1$—/C$^2$—H vinyl), 7.89 (d, 1H, J=8.72 Hz, C$^{2'}$), 8.01-8.09 (m, 1H, C$^6$).

$^{13}$C-NMR (DMSO-d6) δ in ppm: 55.9 (—OCH$_3$), 112.1 (C$^3$), 113.9 (C$^5$), 122.0 (C$^1$), 125.5 (C$^{6'}$), 126.7 (C$^{2'}$), 127.9 (C$^{4'}$), 129.6 (C$^1$ vinyl), 129.6 (C$^2$ vinyl), 131.0 (C$^{5'}$), 133.3 (C$^6$), 133.9 (C$^3$), 139.9 (C$^{1'}$), 140.7 (C$^1$), 162.3 (C$^4$), 168.2 (—COOH).

EXAMPLE 47

2-[2-(3-Chlorophenyl)-ethyl]-4-methoxybenzoic acid (8)

For the synthesis of the title compound, 6.0 g of 2-[2-(3-chlorophenyl)-vinyl]-4-methoxybenzoic acid, 0.6 g of Pd/C (10%) and 4 l of hydrogen are employed in method J (variant 2). The solvent mixture comprises 75 ml of acetonitrile, 75 ml of ethyl acetate and 20 ml of methanol. C$_{16}$H$_{15}$ClO$_3$ (Mr=290.75)

EXAMPLE 48

2-Chloro-8-methoxy-10,11-dihydrodibenzo[a,d]cyclohepten-5-one (9)

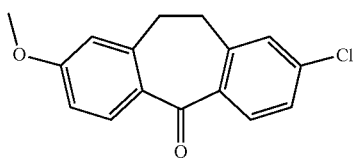 [SMILES: COc1ccc2c(c1)CCc1cc(Cl)ccc1C2=O]

For the synthesis of the title compound, 16.6 g (0.057 mol) of [2-(3-chlorophenyl-ethyl]-4-methoxybenzoic acid, 7.25 g (0.06 mol) of SOCl$_2$, 250 ml of methylene chloride and 10 g of AlCl$_3$ (0.075 mol) are employed in method K. Purification is carried out by column chromatography (flash; SiO$_2$; hexane 90%/ethyl acetate 10%). C$_{16}$H$_{13}$ClO$_2$ (Mr=272.73)

MS m/z (%): 274/272 (34/100, M$^+$), 259/257 (2/5, M$^+$-CH$_3$), 246/244 (9/26, M$^+$-CO), 237 (19, M$^+$-Cl), 231/229 (5/17, 259/257-CO), 208 (17, 244-Cl), 194 (10, 231/229-Cl), 178 (14, 194-O), 165 (43, 4-methoxy-2-methylbenzoic acid).

IR (ATR) 2921, 2852, 1595, 1266, 1203, 1185, 1110, 1031, 942, 912, 874, 839, 814, 769, 722, 596, 537 cm$^{-1}$.

$^1$H-NMR (DMSO-d6) δ in ppm: 3.11 (s, 4H, —CH$_2$—CH$_2$—), 3.82 (s, 3H, —OCH$_3$), 6.87-6.96 (m, 2H, C$^7$—/C$^9$—H), 7.37-7.46 (m, 2H, C$^1$—/C$^3$—H), 7.87 (d, 1H, J=8.37 Hz, C$^6$—H), 7.99 (d, 1H, 8.70 J=8.70 Hz, C$^4$—H).

$^{13}$C-NMR (DMSO-d6) δ in ppm: 34.0 (C$^{11}$), 35.1 (C$^{10}$), 55.8 (—OCH$_3$), 113.1 (C$^7$), 114.6 (C$^9$), 126.9 (C$^3$), 129.0 (C$^1$), 130.0 (C$^{5a}$), 132.7 (C$^6$), 133.7 (C$^4$), 137.1 (C$^{4a}$), 137.5 (C$^2$), 144.5 (C$^{9a}$), 145.7 (C$^{11a}$), 163.1 (C$^8$), 191, (C$^5$).

EXAMPLE 49

2-Chloro-8-hydroxy-10,11-dihydrodibenzo[a,d]cyclohepten-5-one (10)

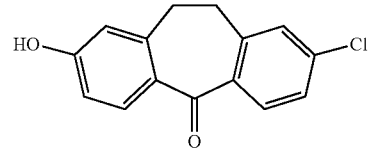 [SMILES: O=C1c2ccc(O)cc2CCc2cc(Cl)ccc21]

For the synthesis of the title compound, 1.0 g (4.87 mmol) of 2-chloro-8-methoxy-10,11-dihydrodibenzo[a,d]cyclohepten-5-one, 10 ml of HBr (48%, aqueous) and 10 ml of glacial acetic acid are employed in method L. C$_{15}$H$_{11}$ClO$_2$ (Mr=258.71)

EXAMPLE 50

(S)-2-Chloro-8-(2,2-dimethyl-[1,3]dioxolan-4-ylmethoxy)-10,11-dihydrodibenzo[a,d]cyclohepten-5-one (14)

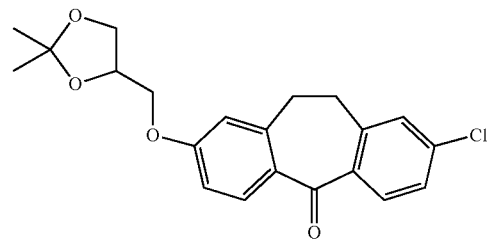 [SMILES: CC1(C)OCC(COc2ccc3c(c2)CCc2cc(Cl)ccc2C3=O)O1]

For the preparation of the title compound, 0.50 g (1.9 mmol) of 2-chloro-8-hydroxy-10,11-dihydrodibenzo[a,d]cyclohepten-5-one, 0.75 g (2.6 mmol) of (R)-toluene-4-sulfonic acid 2,2-dimethyl-[1,3]dioxolan-4-ylmethyl ester and 0.80 g (5.8 mmol) of K$_2$CO$_3$ in 10 ml of dry DMF are reacted by method M. C$_{21}$H$_{21}$ClO$_4$ (Mr=372.85)

EXAMPLE 51

(S)-2-(2,4-Difluorophenylamino)-8-(2,2-dimethyl-[1,3]dioxolan-4-ylmethoxy)-10,11-dihydrodibenzo[a,d]cyclohepten-5-one (12a)

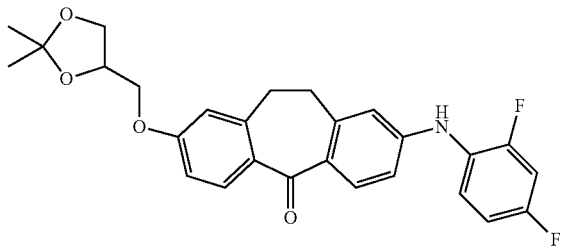 [SMILES: CC1(C)OCC(COc2ccc3c(c2)CCc2cc(Nc4ccc(F)cc4F)ccc2C3=O)O1]

For the synthesis of the title compound, 0.81 g (0.0022 mol) of (S)-2-chloro-1-(2,2-dimethyl-[1,3]dioxolan-4-ylmethoxy)-10,11-dihydrodibenzo[a,d]cyclohepten-5-one, 0.25 g (0.0019 mol) of 2,4-difluoroaniline, 2 spatula tips of Pd(OAc)$_2$, 0.14 g of phosphine ligand and 0.70 g (0.0073 mol) of NaOtert-Bu in 10 ml of toluene and 2 ml of tert-BuOH are reacted by method O. Purification is carried out by column chromatography (flash; SiO$_2$; hexane 80%/ethyl acetate 20%).

$C_{27}H_{25}F_2NO_4$ (Mr=465.50)

EXAMPLE 52

(R)-2-(2,4-Difluorophenylamino)-8-(2,3-dihydroxypropoxy)-10,11-dihydrodibenzo[a,d]cyclohepten-5-one (12c)

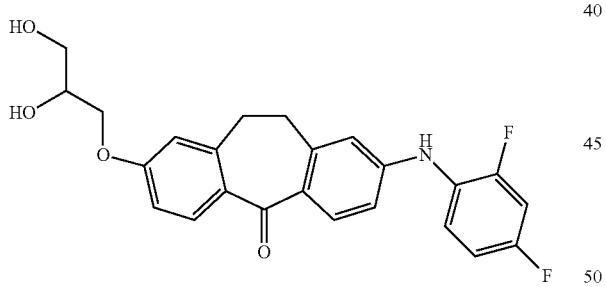

For the synthesis of the title compound, 0.10 g (0.215 mmol) of (S)-8-(2,4-difluorophenylamino)-1-(2,2-dimethyl-[1,3]dioxolan-4-ylmethoxy)-10,11-dihydrodibenzo[a,d]cyclohepten-5-one and 0.0054 g (0.0284 mmol) of p-toluenesulfonic acid monohydrate in 6 ml of methanol and 1.5 ml of water are reacted by method N. $C_{24}H_{21}F_2NO_4$ (Mr=425.44)

$^1$H-NMR (DMSO-d6) δ in ppm: 2.95-3.09 (m, 4H, —CH$_2$—CH$_2$—), 3.42-3.45 (m, 2H, dihydroxypropoxy), 3.76-3.81 (m, 1H, dihydroxypropoxy), 3.89-3.97 (m, 1H, dihydroxypropoxy), 4.04-4.11 (m, 1H, dihydroxypropoxy), 4.86 (s, 2H, C$^2$—/C$^3$—OH dihydroxypropoxy), 6.61 (s, 1H, C$^1$—H), 6.72 (d, 1H, J=9.55 Hz, C$^3$—H), 6.85-6.87 (m, 2H, C$^{3'}$—/C$^{6'}$—H), 7.05-7.12 (m, 1H, C$^{5'}$—H), 7.30-7.47 (m, 2H, C$^7$—/C$^9$—H), 7.95 (d, 2H, J=8.59 Hz, C$^6$—/C$^4$—H), 8.49 (s, 1H, —NH$_2$).

EXAMPLE 53

(S)-2-(2-Aminophenylamino)-8-(2,2-dimethyl-[1,3]dioxolan-4-ylmethoxy)-10,11-dihydrodibenzo[a,d]cyclohepten-5-one (12b)

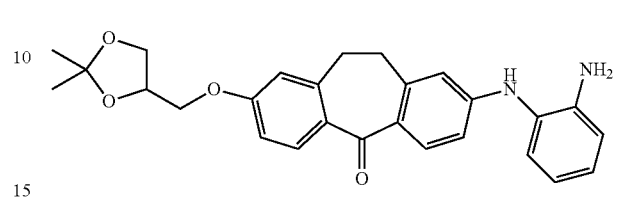

For the synthesis of the title compound, 0.91 g (0.0024 mol) of (S)-2-chloro-8-(2,2-dimethyl-[1,3]dioxolan-4-ylmethoxy)-10,11-dihydrodibenzo[a,d]cyclohepten-5-one, 1.00 g (0.0092 mol) of phenylenediamine, 2 spatula tips of Pd(OAc)$_2$, 0.18 g of phosphine ligand and 1.60 g (0.0166 mol) of NaOtert-Bu in 10 ml of toluene and 2 ml of tert-BuOH are reacted by method O.

Purification is carried out by column chromatography (flash; SiO$_2$; hexane 70%/ethyl acetate 30%). $C_{27}H_{28}N_2O_4$ (Mr=444.54)

$^1$H-NMR (DMSO-d6) δ in ppm: 1.30 (s, 3H, —CH$_3$), 1.35 (s, 3H, —CH$_3$), 2.92-3.05 (m, 4H, —CH$_2$—CH$_2$—), 3.71-3.78 (m, 1H, dioxolane), 3.99-4.13 (m, 3H, dioxolane), 4.38-4.44 (m, 1H, dioxolane), 4.83 (s, 2H, —NH$_2$), 6.46-7.03 (m, 9H, C$^1$—/C$^3$—/C$^4$—/C$^7$—/C$^9$—H and C$^{3'}$—/C$^{4'}$—/C$^{5'}$—/C$^{6'}$—H), 7.91 (s, 1H, C$^6$—H), 7.96 (s, 1H, —NH—).

$^{13}$C-NMR (DMSO-d6) δ in ppm: 25.7 (—CH$_3$), 27.0 (—CH$_3$), 35.1 (C$^{11}$), 36.1 (C$^{10}$), 66.0 (C$^3$ dioxolane), 69.2 (C$^1$ dioxolane), 73.9 (C$^2$ dioxolane), 109.3 (—C—(CH$_3$)$_2$—), 112.0 (C$^7$), 112.9 (C$^9$), 113.0 (C$^3$), 114.3 (C$^1$), 115.8 (C$^{3'}$), 116.8 (C$^{4'}$), 125.3 (C$^{4a}$), 126.1 (C$^{5'}$), 126.3 (C$^{6'}$), 126.7 (C$^{5a}$) 131.8 (C$^{1'}$), 133.6 (C$^6$), 133.9 (C$^4$), 144.0 (C$^{2'}$), 145.0 (C$^{9a}$), 145.4 (C$^2$), 150.8 (C$^{11a}$), 161.3 (C$^8$), 188.7 (C$^5$).

EXAMPLE 54

(R)-2-(2-Aminophenylamino)-8-(2,3-dihydroxypropoxy)-10,11-dihydrodibenzo[a,d]cyclohepten-5-one (12d)

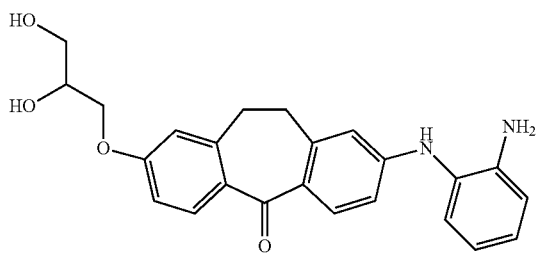 [SMILES: Nc1ccccc1Nc1ccc2c(c1)CCc1cc(OCC(O)CO)ccc1C2=O]

For the synthesis of the title compound, 0.10 g (0.225 mmol) of (S)-2-(2-amino-phenylamino)-8-(2,2-dimethyl-[1,3]dioxolan-4-ylmethoxy)-10,11-dihydrodibenzo[a,d]cyclohepten-5-one and 0.0537 g (0.282 mmol) of p-toluenesulfonic acid monohydrate in 6 ml of methanol and 1.5 ml of water are reacted by method N. $C_{24}H_{24}N_2O_4$ (Mr=404.47)

¹H-NMR (DMSO-d6) δ in ppm: 2.83-3.00 (m, 4H, —CH₂—CH₂—), 3.43 (d, 2H, J=4.80 Hz, C³—H dihydroxypropoxy), 3.93-4.05 (m, 3H, dihydroxypropoxy), 4.68 (s, 1H, C³—OH), 4.83 (s, 2H, —NH₂), 4.96 (s, 1H, C³—OH), 6.44 (s, 1H, C⁶'), 6.54-7.03 (m, 8H, C¹—/C³—/C⁴—/C⁷—/C⁹—H and C³'—/C⁴'—/C⁵'—H), 7.89-7.96 (m, 2H, C⁶—H, —NH—)

¹³C-NMR (DMSO-d6) δ in ppm: 35.2 (C¹¹), 36.1 (C¹⁰), 63.0 (C³ dihydroxypropoxy), 70.1 (C¹ dihydroxypropoxy), 70.2 (C² dihydroxypropoxy), 112.0 (C⁹), 112.8 (C⁷), 113.0 (C³), 114.3 (C¹), 115.8 (C³'), 116.8 (C⁴'), 125.4 (C⁴ᵃ), 126.1 (C⁶'), 126.3 (C⁵'), 126.7 (C⁵ᵃ), 131.5 (C¹'), 133.9 (C⁴), 144.0 (C²), 145.0 (C⁹ᵃ), 145.4 (C²'), 150.8 (C¹¹ᵃ), 161.8 (C⁸), 188.7 (C⁵)

EXAMPLE 55

2-Chloro-8-(2-morpholin-4-ylethoxy)-10,11-dihydrodibenzo[a,d]cyclohepten-5-one (17)

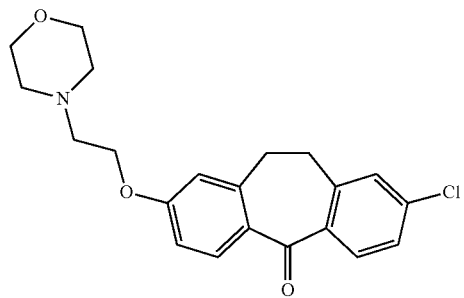 [SMILES: O=C1c2ccc(Cl)cc2CCc2cc(OCCN3CCOCC3)ccc21]

For the synthesis of the title compound, 0.44 g (1.69 mmol) of 2-chloro-8-hydroxy-10,11-dihydrodibenzo[a,d]cyclohepten-5-one, 0.345 g (1.86 mmol) of 4-(2-chloroethyl)morpholine hydrochloride and 0.93 g (6.75 mmol) of K₂CO₃ in 15 ml of acetonitrile are reacted by method Q. C₂₁H₂₂ClNO₃ (Mr=371.87)

¹H-NMR (DMSO-d6) δ in ppm: 2.47 (under DMSO, 4H, C²—/C⁶—H morpholine), 2.68 (t, 2H, J=5.73 Hz, C²—H ethylmorphine), 3.10 (s, 4H, —CH₂—CH₂— cyclohexane), 3.53-3.58 (m, 4H, C³—/C⁵—H morpholine), 4.15 (t, 2H, J=5.69 Hz, C¹—H ethylmorpholine), 6.88-6.96 (m, 2H, C⁷—/C⁹—H), 7.36-7.44 (m, 2H, C¹—/C³—H), 7.87 (d, 1H, J=8.37 Hz, C⁶—H), 7.98 (d, 1H, J=8.64 Hz, C⁴—H).

¹³C-NMR (DMSO-d6) δ in ppm: 34.0 (C¹¹), 35.1 (C¹⁰), 54.0 (2C, C²/C⁶-morpholine), 57.2 (C² ethylmorpholine), 66.0 (C¹ ethylmorpholine), 66.5 (2C, C³/C⁵ morpholine), 113.5 (C⁷), 115.2 (C⁹), 126.9 (C³), 129.0 (C¹), 130.0 (C⁵ᵃ), 132.7 (C⁶), 133.7 (C⁴), 137.1 (C⁴ᵃ), 137.5 (C²), 144.5 (C⁹ᵃ), 145.7 (C¹¹ᵃ), 162.3 (C⁸), 191.0 (C⁵).

EXAMPLE 56

2-(2,4-Difluorophenylamino)-8-(2-morpholin-4-yl-ethoxy)-10,11-dihydrodibenzo[a,d]cyclohepten-5-one (12e)

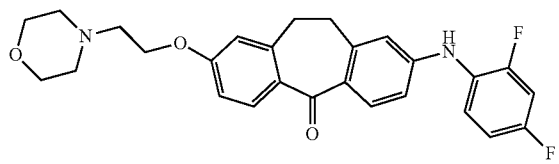 [SMILES: O=C1c2ccc(Nc3ccc(F)cc3F)cc2CCc2cc(OCCN3CCOCC3)ccc21]

For the synthesis of the title compound, 0.45 g (0.0013 mol) of 8-chloro-1-(2-morpholin-4-yl-ethoxy)-10,11-dihydrodibenzo[a,d]cyclohepten-5-one, 0.20 g (0.0015 mol) of 2,4-difluoroaniline, 2 spatula tips of Pd(OAc)₂, 0.14 g of phosphine ligand and 0.70 g (0.0073 mol) of NaOtert-Bu in 10 ml of toluene and 2 ml of tert-BuOH are reacted by method O.

Purification is carried out by column chromatography (flash; SiO₂; hexane 80%/ethyl acetate 20%).

C₂₇H₂₆F₂N₂O₂ (Mr=464.52)

¹H-NMR (DMSO-d6) δ in ppm: 2.49 (under DMSO, 4H, C²—/C⁶—H morpholine), 2.69 (t, 2H, J=5.51 Hz, C²—H ethylmorpholine), 2.96-3.07 (m, 4H, —CH₂—CH₂— cycloheptane), 3.56 (t, 4H, J=4.50 Hz, C³—/C⁵—H morpholine), 4.15 (t, 2H, J=5.44 Hz, C¹—H ethylmorpholine), 6.61 (s, 1H, C¹—H), 6.73 (d, 1H, J=8.43 Hz, C³—H), 6.86-6.91 (m, 2H, C³'—/C⁶'—H), 7.05-7.13 (m, 1H, C⁵'—H), 7.30-7.47 (m, 2H, C⁷—/C⁹—H), 7.95 (d, 2H, J=8.66 Hz, C⁴—/C⁶—H), 8.49 (s, 1H, —NH—).

¹³C-NMR (DMSO-d6) δ in ppm: 35.1 (s, C¹¹), 35.8 (s, C¹⁰), 53.9 (s, 2C, C²/C⁶ morpholine), 57.3 (s, C² ethylmorpholine), 65.9 (s, C¹, ethylmorpholine), 66.5 (s, 2C, C³/C⁵ morpholine), 105.3 (dd, J₁=25.5 Hz, J₂=24.2 Hz, C³'), 112.2 (dd, J₁=21.9 Hz, J₂=3.8 Hz, C⁵'), 112.5 (s, C⁷), 113.1 (s, C⁹), 113.6 (s, C⁹), 114.5 (s, C¹), 125.5 (dd, J₁=12.0 Hz, J₂=3.4 Hz, C¹'), 126.3 (dd, J₁=9.5 Hz, J₂=3.1 Hz, C⁶'), 128.2 (s, C⁴ᵃ), 131.3 (s, C⁵ᵃ), 133.6 (s, C⁶), 133.8 (s, C⁴), 145.1 (s, C²), 145.3 (s, C¹¹ᵃ), 149.1 (s, C⁹ᵃ), 154.9 (dd, J₁=141.3 Hz, J₂=11.0, C⁴'), 159.7 (dd, J₁=129.7 Hz, J₂=12.0 Hz, C²'), 161.6 (s, C⁸), 189.1 (s, C⁵).

Substitution in Position 9—Compounds and Precursors

EXAMPLE 57

2-Bromomethyl-3-methoxybenzoic acid (1)

for the synthesis of the title compound, 6.64 g (0.040 mol) of 3-methoxy-2-methylbenzoic acid, 7.1 g (0.040 mol) of NBS and 0.25 g of AIBN in 150 ml of chlorobenzene are reacted by method H (variant 1).

C₉H₉BrO₃ (Mr=245.07); yield: 55%

¹H-NMR (DMSO-d6) δ in ppm: 3.89 (s, 3H, —OCH₃), 5.03 (s, 2H, —CH₂—Br), 7.23-7.28 (m, 1H, C⁵—H), 7.41-7.46 (m, 2H, C⁴—/C⁵—H), 13.25 (s, 1H, —COOH).

¹³C-NMR (DMSO-d6) δ in ppm: 56.1 (—OCH₃), 68.4 (—CH₂Br), 116.3 (C⁴), 116.8 (C⁶), 126.9 (C²), 131.4 (C⁵), 135.3 (C¹), 154.3 (C³), 170.9 (—COOH).

EXAMPLE 58

2-[2-(3-Chlorophenyl)-vinyl]-3-methoxybenzoic acid (2)

For the synthesis of the title compound, 45.6 g (0.186 mol) of 2-bromomethyl-3-methoxybenzoic acid, 48.8 g (0.186 mol) of triphenylphosphine, 26.1 g (0.186 mol) of 3-chlorobenzaldehyde and 84.0 g (0.435 mol) of NaOMe (28%) in 150 ml of methanol are reacted by method I. Purification is carried out by recrystallization from methanol with water.

C₁₆H₁₃ClO₃ (Mr=288.3); yield 51%; m.p.: 119° C.

IR (ATR) 2923, 2360, 2342, 1685, 1587, 1451, 1300, 1275, 1260, 1220, 1197, 1178, 1049, 973, 964, 914, 889, 872, 810, 783, 761, 749, 729, 705, 684, 667, 621, 530, 457, 432 cm⁻¹.

¹H-NMR (DMSO-d6) δ in ppm: 3.86 (s, 3H, —OCH₃), 7.04-7.55 (m, 9H, diphenylethene), 13.03 (s, 1H, —COOH).

¹³C-NMR (DMSO-d6) δ in ppm: 56.3 (O—CH₃), 114.2 (C⁴), 121.4 (C⁶), 124.8 (C²), 125.2 (C¹/C² vinyl), 126.2 (C⁶'), 127.6 (C$^{2'}$), 128.8 (C$^{4'}$), 130.9 (C$^5$), 132.0 (C$^{5'}$), 133.9 (C$^1$), 134.0 (C$^3$'), 140.4 (C$^{1'}$), 157.9 (C$^3$), 169.9 (—COOH).

EXAMPLE 59

2-[2-(3-Chlorophenyl)-ethyl]-3-methoxybenzoic acid (3)

For the synthesis of the title compound, 6.0 g of 2-[2-(3-chlorophenyl)-vinyl]-3-methoxybenzoic acid, 0.6 g of Pd/BaSO$_4$ (5%), 4 l of hydrogen and 150 ml of methanol are employed in method J (variant 1). Yield: 87%; m.p.: 91° C.; C$_{16}$H$_{15}$ClO$_3$ (Mr=290.75)

IR (ATR) 2947, 2359, 2342, 1691, 1461, 1436, 1276, 1250, 1214, 1089, 1058, 1000, 782, 753, 696, 681 cm$^{-1}$.

$^1$H-NMR (DMSO-d6) δ in ppm: 2.74 (t, 2H, J=8.07 Hz, C$^1$ ethyl), 3.11 (t, 2H, J=8.08, C$^2$ ethyl), 3.79 (s, 3H, —OCH$_3$), 7.15 (d, 2H, C$^4$—H and C$^{6'}$—H), 7.22-7.25 (m, 2H, C$^5$—H and C$^{5'}$—H), 7.27 (s, 1H, C$^{2'}$—H), 7.30-7.37 (m, 2H, C$^6$—H and C$^{4'}$—H).

$^{13}$C-NMR (DMSO-d6) δ in ppm: 28.7 (C$^1$ ethyl), 35.7 (C$^2$ ethyl), 56.3 (—OCH$_3$), 114.2 (C$^4$), 122.0 (C$^6$), 126.1 (C$^6$'), 127.2 (C$^{4'}$), 128.3 (C$^{2'}$), 130.3 (C$^{5'}$), 130.4 (C$^1$), 132.6 (C$^2$), 133.2 (C$^{3'}$), 145.0 (C$^{1'}$), 157.8 (C$^3$), 169.4 (—COOH).

EXAMPLE 60

8-Chloro-1-methoxy-10,11-dihydrodibenzo[a,d]cyclohepten-5-one (4)

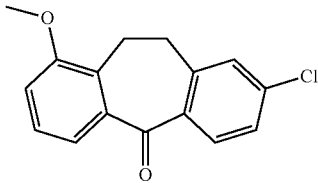 [SMILES: COc1cccc2c1CCc1cc(Cl)ccc1C2=O]

For the synthesis of the title compound, 16.6 g (0.057 mol) of [2-(3-chlorophenyl)-ethyl]-3-methoxybenzoic acid, 7.25 g (0.06 mol) of SOCl$_2$, 250 ml of methylene chloride and 10 g of AlCl$_3$ are employed in method K. Purification is carried out by column chromatography (flash; SiO$_2$; hexane 90%/ethyl acetate 10%).

C$_{16}$H$_{13}$ClO$_2$ (Mr=272.73); yield: 47%; m.p.: 75° C.; GC 13.5 min

MS m/z (%): 274/272 (35/100, M$^+$), 259/257 (6/18, M$^+$-CH$_3$), 245/243 (5/15, M$^+$-CO), 231/229 (3/11, 259/257-CO), 208 (17, 243-Cl), 194 (20, 231/229-Cl), 178 (23, 194-O), 165 (44, 3-methoxy-2-methylbenzoic acid).

IR (ATR) 2946, 2901, 2359, 1659, 1589, 1575, 1312, 1284, 1254, 1228, 1184, 1087, 1062, 960, 862, 795, 754, 722, 706 cm$^{-1}$.

$^1$H-NMR (DMSO-d6) δ in ppm: 3.08 (s, 4H, —CH$_2$—CH$_2$—) 3.82 (s, 3H, —OCH$_3$), 7.18-7.42 (m, 5H, C$^2$/C$^3$/C$^4$/C$^7$/C$^9$—H), 7.68 (d, 1H, J=8.28 Hz, C$^6$—H).

$^{13}$C-NMR (DMSO-d6) δ in ppm: 26.2 (C$^{11}$), 32.9 (C$^{10}$), 56.4 (—OCH$_3$), 114.9 (C$^2$), 121.7 (C$^4$), 127.0 (C$^7$), 127.6 (C$^3$), 129.0 (C$^9$), 130.3 (C$^{5a}$), 131.3 (C$^6$), 137.1 (C$^{4a}$), 138.1 (C$^{11a}$), 139.4 (C$^8$), 143.7 (C$^{9a}$), 156.7 (C$^1$), 195.2 (C$^5$).

EXAMPLE 61

8-Chloro-1-hydroxy-10,11-dihydrodibenzo[a,d]cyclohepten-5-one (5)

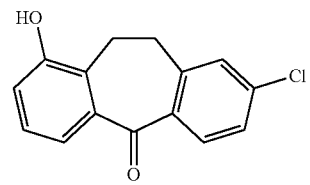 [SMILES: O=C1c2ccc(Cl)cc2CCc2c(O)cccc21]

For the synthesis of the title compound, 1.0 (4.87 mmol) g of 8-chloro-1-methoxy-10,11-dihydrodibenzo[a,d]cyclohepten-5-one, 10 ml of HBr (48%, aqueous) and 10 ml of glacial acetic acid are employed in method L. Yield: 95%; m.p.: 185° C.; GC 15.2 min; C$_{15}$H$_{11}$ClO$_2$ (Mr=258.71)

MS m/z (%): 260/258 (34/100, M$^+$), 243/241 (2/7, M$^+$-OH), 232/230 (9/27, M$^+$-CO), 223 (21, M$^+$-Cl), 217/215 (2/7), 207/205 (2/6), 195 (28, 223-CO), 177 (12), 165 (39).

IR (ATR) 3251, 2360, 1637, 1573, 1307, 1282, 1241, 1221, 1176, 1159, 886, 759 cm$^{-1}$.

$^1$H-NMR (DMSO-d6) δ in ppm: 3.07 (s, 4H, —CH$_2$—CH$_2$—), 7.04 (d, 1H, J=7.84 Hz, C$^2$—H), 7.15 (t, 1H, J=7.78 Hz, C$^3$—H), 7.28 (d, 1H, J=7.69 Hz, C$^7$—H), 7.38 (d, 1H, J=8.31 Hz, C$^4$—H), 7.45 (s, 1H, C$^9$—H), 7.67 (d, 1H, J=8.32, C$^6$—H), 9.84 (s, 1H, —OH).

$^{13}$C-NMR (DMSO-d6) δ in ppm: 26.5 (C$^{11}$), 33.0 (C$^{10}$), 119.1 (C$^2$), 120.6 (C$^4$), 126.9 (C$^7$), 127.2 (C$^3$), 128.7 (C$^9$), 129.0 (C$^{5a}$), 131.3 (C$^6$), 136.9 (C$^{4a}$), 138.4 (C$^{11a}$), 139.5 (C$^8$), 143.8 (C$^{9a}$), 155.0 (C$^1$), 195.4 (C$^5$).

EXAMPLE 62

8-(2,4-Difluorophenylamino)-1-hydroxy-10,11-dihydrodibenzo[a,d]cyclohepten-5-one (11c)

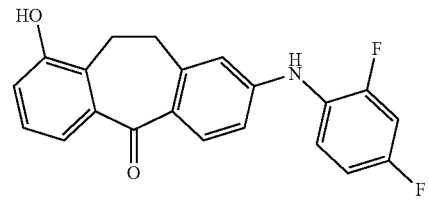 [SMILES: O=C1c2ccc(Nc3ccc(F)cc3F)cc2CCc2c(O)cccc21]

For the synthesis of the title compound, 0.52 g (0.0020) mol of 8-chloro-1-hydroxy-10,11-dihydrodibenzo[a,d]cyclohepten-5-one, 0.26 g (0.0020 mol) of 2,4-difluoroaniline, 2 spatula tips of Pd(OAc)$_2$, 0.14 g of phosphine ligand and 0.90 g (0.0094 mol) of NaOtert-Bu in 10 ml of toluene and 2 ml of tert-BuOH are reacted by method O. Purification is carried out by column chromatography (flash; silica gel, 90% hexane+10% ethyl acetate). C$_{21}$H$_{15}$F$_2$NO$_2$ (Mr=351.36); GC 35.3 min MS m/z (%): 351 (100, M+), 336 (4, M+-O), 323 (10, M+-CO), 308 (3, 323-O), 223 (2, 336-difluorobenzene), 194 (12, 223-CO), 165 (13, 3-methoxy-2-methylbenzoic acid), 129 (1, difluoroaniline), 115 (1, difluoroaniline).

¹H-NMR (DMSO-d6) δ in ppm: 2.93-3.06 (m, 4H, —CH₂—CH₂—), 6.61 (s, 1H, C⁹—H), 6.71 (d, 1H, J=8.04 Hz, C⁶'—H), 6.98 (d, 1H, J=7.84 Hz, C⁷—H), 7.05-7.13 (m, 2H, C³'—/C⁵'—H), 7.24 (d, 1H, J=7.62 Hz, C²—H), 7.34-7.39 (m, 2H, C³—/C⁴—H), 7.41-7.78 (m, 1H, C⁶—H), 8.46 (s, 1H, —NH—), 9.69 (s, 1H, —OH).

EXAMPLE 63

8-(2,4-Difluorophenylamino)-1-methoxy-10,11-dihydrodibenzo[a,d]cyclohepten-5-one (11a)

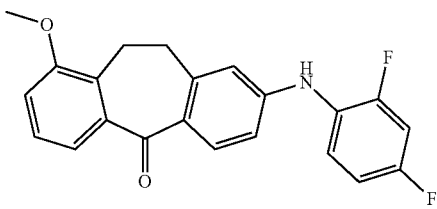 [SMILES: COc1cccc2c1CCc1cc(Nc3ccc(F)cc3F)ccc1C2=O]

For the synthesis of the title compound, 0.54 g (0.0020 mol) of 8-chloro-1-methoxy-10,11-dihydrodibenzo[a,d]cyclohepten-5-one, 0.26 g (0.0020 mol) of 2,4-difluoroaniline, 2 spatula tips of Pd(OAc)₂, 0.14 g of phosphine ligand and 0.70 g (0.0073 mol) of NaOtert-Bu in 10 ml of toluene and 2 ml of tert-BuOH are reacted by method O. Purification is carried out by column chromatography (flash; SiO₂; hexane 90%/ethyl acetate 10%). C₂₂H₁₇F₂NO₂ (Mr=365.38)

Yield: g (%); m.p.: 216° C.; GC 31.6 min

MS m/z (%): 365 (100, M⁺), 350 (6, M⁺-CH₃), 336(8), 322 (5, 350-CO), 306 (3, 322-O), 208 (11, M⁺-CO —NH-Phe), 194 (8, 208-CH₃), 178 (9, 194-O), 165 (17).

IR (ATR) 3276, 1299, 1286, 1269, 1255, 1193, 1073, 966, 863, 828, 764, 727, 603, 534, 496, 460, 446 cm⁻¹.

¹H-NMR (DMSO-d6) δ in ppm: 2.94-3.08 (m, 4H, —CH₂—CH₂—), 3.82 (s, 3H, —OCH₃), 6.61 (s, 1H, C⁹—H), 6.72 (d, 1H, J=8.72 Hz, C⁷—H), 7.03-7.17-(m, 2H, C³'—/C⁶'—H), 7.23-7.45-(m, 4H, C²—/C³—/C⁴—H and C⁵'—H), 7.83 (d, 1H, J=8.69, C⁶—H), 8.49 (s, 1H, NH).

¹³C-NMR (DMSO-d6) δ in ppm: 25.0 (s, C¹¹), 35.1 (s, C¹⁰), 56.4 (s, —OCH₃), 105.5 (d, J=26.6 Hz, C³), 112.2 (d, J=25.6 Hz, C⁵), 112.6 (s, C⁷), 113.8 (s, C⁹), 114.3 (s, C²), 121.9 (s, C⁴), 125.4 (d, J=12.1 Hz, C¹), 126.3 (d, J=9.6 Hz, C⁶'), 127.3 (s, C³), 128.4 (s, C⁵ᵃ), 130.1 (s, C⁴ᵃ), 132.9 (s, C⁶), 141.2 (s, C¹¹ᵃ), 145.2 (s, C⁸), 149.3 (s, C⁹ᵃ), 154.9 (d, J=141.2 Hz, C⁴'), 155.8 (s, C¹), 159.8 (d, J=137.1 Hz, C²), 192.6 (s, C⁵).

EXAMPLE 64

8-(2-Aminophenylamino)-1-methoxy-10,11-dihydrodibenzo[a,d]cyclohepten-5-one (11b)

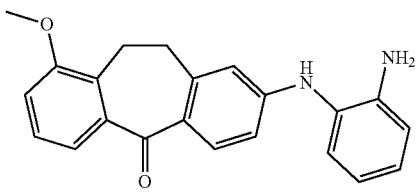 [SMILES: COc1cccc2c1CCc1cc(Nc3ccccc3N)ccc1C2=O]

For the synthesis of the title compound, 0.54 g (0.0020 mol) of 8-chloro-1-methoxy-10,11-dihydrodibenzo[a,d]cyclohepten-5-one, 1.08 g (0.010 mol) of phenylenediamine, 2 spatula tips of Pd(OAc)₂, 0.14 g of phosphine ligand and 1.60 g (0.0166 mol) of NaOtert-Bu in 10 ml of toluene and 2 ml of tert-BuOH are reacted by method O. Purification is carried out by column chromatography (flash; SiO₂; hexane 80%/ethyl acetate 20%). C₂₂H₂₀N₂O₂ (Mr=344.42)

Yield: 46(%): m.p.: 132° C.; GC 54.5 min

MS m/z (%): 344 (100, M⁺), 329 (13, M⁺-CH₃), 315 (6, M⁺-CO), 301 (5, 315-CH₂), 285 (5, 301-O), 195 (9, 301-1,2-diaminobenzene), 182 (6), 165 (8,3-methoxy-2-methylbenzoic acid), 107 (13, 1,2-diaminobenzene), 80 (7).

IR (ATR) 3356, 3282, 2852, 1616, 1587, 1563, 1553, 1497, 1335, 1293, 1272, 1255, 1222, 1192, 1075, 826, 759, 749, 706, 540, 505, 438 cm⁻¹.

¹H-NMR (DMSO-d6) δ in ppm: 2.93-3.02 (m, 4H, —CH₂—CH₂—), 3.81 (s, 3H, —OCH₃), 4.82 (s, 2H, —NH₂), 6.45 (s, 1H, C⁹—H), 6.59 (d, 2H, J=8.22 Hz, C³'—/C⁶'—H), 6.76 (d, 1H, J=7.66 Hz, C⁷—H), 6.89-7.02 (m, 2H, C⁴'—/C⁵'—H), 7.13 (d, 1H, J=7.47 Hz, C²—H), 7.21-7.37 (m, 2H, C³—/C⁴—H), 7.80-8.01 (m, 2H, —NH, C⁶—H).

¹³C-NMR (DMSO-d6) δ in ppm: 24.8 (C¹¹), 35.5 (C¹⁰), 56.4 (—OCH₃), 112.0 (C⁷), 113.0 (C³'), 114.1 (C⁹), 115.8 (C²), 116.8 (C⁴'), 122.0 (C⁵'), 125.3 (C⁵ᵃ), 126.1 (C⁶'), 126.3 (C⁴), 126.8 (C⁴ᵃ), 127.2 (C³), 130.0 (C¹¹ᵃ), 133.2 (C⁶), 141.5 (C¹), 144.0 (C²), 145.4 (C⁹ᵃ), 151.0 (C⁸), 155.6 (C¹), 191.9 (C⁵).

EXAMPLE 65

(S)-8-Chloro-1-(2,2-dimethyl-[1,3]dioxolan-4-ylmethoxy)-10,11-dihydrodibenzo[a,d]cyclohepten-5-one (13)

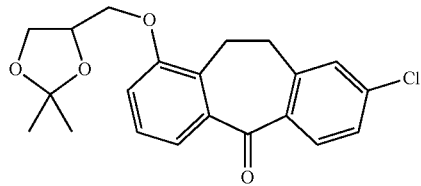 [SMILES: CC1(C)OCC(COc2cccc3c2CCc2cc(Cl)ccc2C3=O)O1]

For the preparation of the title compound, 0.50 g (1.9 mmol) of 8-chloro-1-hydroxy-10,11-dihydrodibenzo[a,d]cyclohepten-5-one, 0.75 g (2.6 mmol) of (R)-toluene-4-sulfonic acid 2,2-dimethyl-[1,3]dioxolan-4-ylmethyl ester and 0.80 g (5.8 mmol) of K₂CO₃ in 10 ml of dry DMF are reacted by method M. Yield: 53%; C₂₁H₂₁ClO₄ (Mr=372.85); GC 22.8 min MS m/z (%): 374/372 (35/100, M⁺), 359/357 (6/17, M⁺-CH₃), 337 (2, M⁺-Cl), 316/314 (10/26, 359/357-CH₃), 299/297 (16/39, 316/314-OH), 285/283 (3/8, 299/297-CH₂), 269 (283), 258/256 (15/6 M⁺-dioxolane), 194 (12, 258/256-Cl—CO), 178 (23, 194-CO), 165 (51, 3-methoxy-2-methylbenzoic acid).

IR (ATR) 2962, 2359, 1650, 1586, 1449, 1370, 1310, 1284, 1257, 1213, 1177, 1156, 1057, 974, 873, 790, 761, 694, 665, 555 cm⁻¹.

¹H-NMR (DMSO-d6) δ in ppm: 1.31 (s, 3H, —CH₃), 1.36 (s, 3H, —CH₃), 3.11 (s, 4H, —CH₂—CH₂), 3.78-3.86 (m, 1H, dioxolane), 4.00-4.11 (m, 3H, dioxolane), 4.41-4.46 (m, 1H, dioxolane), 7.25-7.44 (m, 4H, C²—/C³—/C⁴—/C⁷—H), 7.47 (s, 1H, C⁹—H), 7.69 (d, 1H, J=8.34 Hz, C⁶—H).

¹³C-NMR (DMSO-d6) δ in ppm: 25.7 (—CH₃), 26.3 (—CH₃), 26.9 (C¹¹), 32.8 (C¹⁰), 66.0 (C³ dioxolane), 69.8 (C¹ dioxolane), 74.1 (C² dioxolane), 109.2 (—C(CH₃)₂), 116.3 (C²), 122.1 (Cᵃ), 127.0 (C⁷), 127.6 (C³), 129.1 (C⁹, 130.7 (C$^{5a}$), 131.3 (C$^6$), 137.1 (C$^{4a}$), 138.2 (C$^{11a}$), 139.5 (C$^8$), 143.7 (C$^{9a}$), 155.9 (C$^1$), 195.2 (C$^5$).

EXAMPLE 66

(S)-8-(2,4-Difluorophenylamino)-1-(2,2-dimethyl-[1,3]dioxolan-4-ylmethoxy)-10,11-dihydrodibenzo[a,d]cyclohepten-5-one (11d)

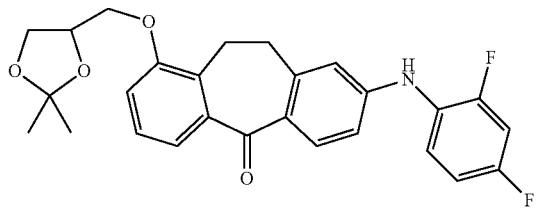 [SMILES: CC1(C)OCC(COc2cccc3c2CCc2cc(Nc4ccc(F)cc4F)ccc2C3=O)O1]

For the synthesis of the title compound, 0.50 g (0.0013 mol) of (S)-8-chloro-1-(2,2-dimethyl-[1,3]dioxolan-4-ylmethoxy)-10,11-dihydrodibenzo[a,d]cyclohepten-5-one, 0.17 g (0.0013 mol) of 2,4-difluoroaniline, 2 spatula tips of Pd(OAc)$_2$, 0.14 g of phosphine ligand and 0.70 g (0.0073 mol) of NaOtert-Bu in 10 ml of toluene and 2 ml of tert-BuOH are reacted by method O.

Purification is carried out by column chromatography (flash; SiO$_2$; hexane 80%/ethyl acetate 20%). C$_{27}$H$_{25}$F$_2$NO$_4$ (Mr=465.50); yield: 37%; m.p.: 127° C.;

IR (ATR) 3307, 2981, 1503, 1287, 1257, 1207, 1139, 1062, 1041, 864, 843, 832, 810, 757, 541, 515 cm$^{-1}$.

$^1$H-NMR (DMSO-d6) δ in ppm: 1.31 (s, 3H, —CH$_3$), 1.36 (s, 3H, —CH$_3$), 2.96-3.11 (m, 4H, —CH$_2$—CH$_2$—), 3.78-3.85 (m, 1H, dioxolane), 4.04-4.14 (m, 3H, dioxolane), 4.38-4.46 (m, 1H, dioxolane), 6.62-6.73 (m, 2H, C7-/C9-H), 7.08-7.43 (m, 6H, C$^2$—/C$^3$—/C$^4$—H and C$^{3'}$—/C$^{5'}$—/C$^{6'}$—H), 7.81 (d, 1H, J=8.72 Hz, C$^6$), 8.49 (s, 1H, —NH—).

$^{13}$C-NMR (DMSO-d6) δ in ppm: 25.1 (s, C$^{10}$), 25.7 (s, —CH$_3$), 26.9 (s, —CH$_3$), 35.0 (s, C$^{11}$), 66.0 (s, C$^3$ dioxolane), 69.9 (s, C$^1$ dioxolane), 74.1 (s, C$^2$ dioxolane), 105.0 (d, J=26.4 Hz, C$^{3'}$), 109.2 (s, —C(CH$_3$)$_2$), 112.2 (d, J=21.8 Hz, C$^{5'}$), 112.6 (s, C$^7$), 113.9 (s, C$^9$), 115.7 (s, C$^2$), 122.3 (s, C$^4$), 125.4 (d, J=15.8 Hz, C$^{1'}$), 126.2 (d, J=6.7 Hz, C$^{6'}$), 127.2 (s, C$^3$), 128.5 (s, C$^{5a}$), 130.4 (s, C$^{4a}$), 132.9 (s, C$^6$), 141.3 (s, C$^{11a}$), 145.1 (s, C$^8$), 149.3 (s, C$^{9a}$), 154.9 (d, J=138.5 Hz, C$^4$), 155.0 (s, C$^1$), 159.7 (d, J=148.2 Hz, C$^2$), 192.6 (s, C$^5$).

EXAMPLE 67

(R)-8-(2,4-Difluorophenylamino)-1-(2,3-dihydroxypropoxy)-10,11-dihydrodibenzo-[a,d]cyclohepten-5-one (11f)

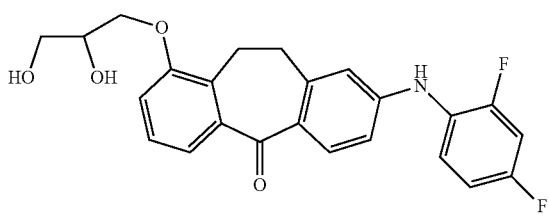 [SMILES: O=C1c2ccc(Nc3ccc(F)cc3F)cc2CCc2c(OCC(O)CO)cccc21]

For the synthesis of the title compound, 0.10 g (0.215 mmol) of (S)-8-(2,4-difluorophenylamino)-1-(2,2-dimethyl-[1,3]dioxolan-4-ylmethoxy)-10,11-dihydrodibenzo[a,d]cyclohepten-5-one and 0.0054 g (0.0284 mmol) of p-toluenesulfonic acid monohydrate in 6 ml of methanol and 1.5 ml of water are reacted by method N. Yield: 88%;

m.p.: 125° C.

C$_{24}$H$_{21}$F$_2$NO$_4$ (Mr=425.44)

IR (ATR) 3307, 1541, 1305, 1257, 1217, 1138, 1116, 1098, 1061, 967, 847, 833, 812, 758, 601, 570, 539, 458 cm$^{-1}$.

$^1$H-NMR (DMSO-d6) δ in ppm: 3.00-3.08 (m, 4H, —CH$_2$—CH$_2$—), 3.46-3.49 (m, 2H, dihydroxypropoxy), 3.78-4.03 (m, 3H, dihydroxypropoxy), 6.63-6.73 (m, 2H, C$^7$-/C$^9$—H), 7.04-7.41 (m, 6H, C$^2$—/C$^3$—/C$^4$—H and C$^3$—/C$^{5'}$—/C$^{6'}$—H), 7.80 (d, 1H, J=8.73 Hz, C$^6$), 8.48 (s, 1H, —NH).

$^{13}$C-NMR (DMSO-d6) δ in ppm: 25.2 (s, C$^{11}$), 35.0 (s, C$^{10}$), 63.1 (s, C$^3$ dihydroxypropoxy), 70.4 (s, C$^2$ dihydroxypropoxy), 70.9 (s, C$^1$ dihydroxypropoxy), 105.3 (t, J=25.3 Hz, C$^{3'}$), 112.1 (d, J=25.9 Hz, C$^{5'}$), 112.5 (s, C$^7$), 113.9 (s, C$^9$), 115.5 (s, C$^2$), 121.9 (s, C$^4$), 125.4 (d, J=15.6 Hz, C$^{1'}$), 126.1 (d, J=9.6 Hz, C$^{6'}$), 127.2 (s, C$^3$), 128.6 (s, C$^{5a}$), 130.5 (s, C$^{4a}$), 132.8 (s, C$^6$), 141.2 (s, C$^{11a}$), 145.1 (s, C$^8$), 149.2 (s, C$^{9a}$), 154.8 (d, J=141.5 Hz, C$^4$), 155.5 (s, C$^1$), 159.7 (d, J=136.2 Hz, C$^{2'}$), 192.7 (s, C$^5$).

EXAMPLE 68

(S)-8-(2-Aminophenylamino)-1-(2,2-dimethyl-[1,3]dioxolan-4-ylmethoxy)-10,11-dihydrodibenzo[a,d]cyclohepten-5-one (11e)

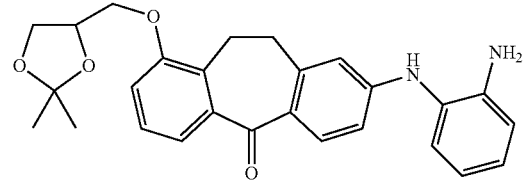 [SMILES: CC1(C)OCC(COc2cccc3c2CCc2cc(Nc4ccccc4N)ccc2C3=O)O1]

For the synthesis of the title compound, 0.50 g (0.0013 mol) of (S)-2-chloro-8-(2,2-dimethyl-[1,3]dioxolan-4-ylmethoxy)-10,11-dihydrodibenzo[a,d]cyclohepten-5-one, 0.70 g (0.0065 mol) of phenylenediamine, 2 spatula tips of Pd(OAc)$_2$, 0.14 g of phosphine ligand and 1.04 g (0.0108 mol) of NaOtert-Bu in 10 ml of toluene and 2 ml of tert-BuOH are reacted by method O.

Purification is carried out by column chromatography (flash; SiO$_2$; hexane 70%/ethyl acetate 30%). Yield: 23%; m.p.: <35° C.; C$_{27}$H$_{28}$N$_2$O$_4$ (Mr=444.54)

IR (ATR) 3347, 2927, 1566, 1499, 1450, 1254, 1212, 1155, 1069, 969, 908, 832, 745, 703, 599, 512, 448 cm$^{-1}$.

$^1$H-NMR (DMSO-d6) δ in ppm: 1.31 (s, 3H, —CH$_3$), 1.36 (s, 3H, —CH$_3$), 2.91-3.10 (m, 4H, —CH$_2$—CH$_2$—), 3.78-3.85 (m, 1H, dioxolane), 4.00-4.03 (m, 3H dioxolane), 4.40-4.43 (m, 1H, dioxolane), 4.82 (s, 2H, —NH$_2$), 6.47-6.62 (m, 3H, C$^9$—H and C$^{5'}$—/C$^{6'}$—H), 6.78 (d, 1H, J=7.29 Hz, C$^{3'}$—H), 6.92 (d, 1H, J=7.17 Hz, C$^7$—H), 7.01 (d, 1H, J=7.76 Hz, C$^2$—H), 7.16-7.24 (m, 2H, C$^3$—H and C$^4$—H), 7.38 (d, 1H, J=7.55 Hz, C$^4$—H), 7.82 (d, 1H, J=8.74 Hz, C$^6$—H), 7.91 (s, 1H, —NH—).

$^{13}$C-NMR (DMSO-d6) δ in ppm: 24.9 (C$^{11}$), 25.7 (—CH$_3$), 26.9 (—CH$_3$), 35.4 (C$^{10}$), 66.0 (C$^3$ dioxolane), 69.9 (C$^1$ dioxolane), 74.1 (C$^2$ dioxolane), 109.2 (—C(CH$_3$)$_2$), 112.0 (C$^7$), 113.1 (C$^9$), 115.5 (C$^{3'}$), 115.8 (C$^2$), 116.8 (C$^4$), 122.4 (C$^{5'}$), 125.3 (C$^{5a}$), 126.0 (C$^{6'}$), 126.3 (C$^4$), 126.9 (C$^3$), 127.2 (C$^{4a}$), 130.4 (C$^{11a}$), 133.1 (C$^6$), 141.6 (C$^{1'}$), 193.9 (C$^{2'}$), 145.3 (C$^8$), 150.9 (C$^{9a}$), 154.9 (C$^1$), 191.9 (C$^5$).

EXAMPLE 69

(R)-8-(2-Aminophenylamino)-1-(2,3-dihydroxypropoxy)-10,11-dihydrodibenzo[a,d]cyclo-hepten-5-one (11g)

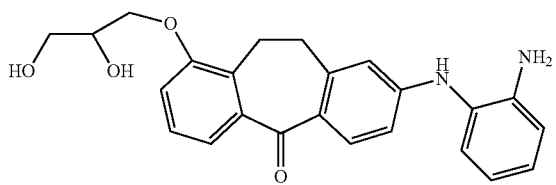 [SMILES: Nc1ccccc1Nc1ccc2c(c1)CCc1c(OCC(O)CO)cccc1C2=O]

For the synthesis of the title compound, 0.10 g (0.225 mmol) of (S)-8-(2-aminophenylamino)-1-(2,2-dimethyl-[1,3]dioxolan-4-ylmethoxy)-10,11-dihydrodibenzo[a,d]cyclohepten-5-one and 0.0537 g (0.282 mmol) of p-toluenesulfonic acid monohydrate in 6 ml of methanol and 1.5 ml of water are reacted by method N. C$_{24}$H$_{24}$N$_2$O$_4$ (Mr=404.47); yield: 40%

IR (ATR) 3305, 2919, 1566, 1498, 1449, 1255, 1216, 1189, 1155, 1111, 1043, 967, 908, 831, 749, 703, 448, 405 cm$^{-1}$.

$^1$H-NMR (DMSO-d6) δ in ppm: 2.93-3.11 (m, 4H, —CH$_2$—CH$_2$—), 3.47 (d, 2H, J=5.48 Hz, C$^3$—H dihydroxypropoxy), 3.83 (q, 1H, J=5.60 Hz, C$^2$—H dihydroxypropoxy), 3.85-4.06 (m, 2H, C$^1$—H dihydroxypropoxy), 4.82 (s, 2H, —NH$_2$), 6.48 (s, 1H, C$^9$—H), 6.59 (d, 2H, J=7.39 Hz, C$^{3'}$—/C$^{6'}$—H), 6.76 (d, 1H, J=7.41 Hz, C$^7$—H), 6.90-7.02 (m, 2H, C$^4$—H and C$^{5'}$—H), 7.12 (d, 1H, J=7.37 Hz, C$^2$—H), 7.23 (t, 1H, J=7.80 Hz, C$^3$—H), 7.34 (d, 1H, J=7.09 Hz, C$^4$—H), 7.80 (d, 1H, J=8.74 Hz, C$^6$—H), 7.91 (s, 1H, —NH—).

$^{13}$C-NMR (DMSO-d6) δ in ppm: 25.0 (C$^{11}$), 35.4 (C$^{10}$), 63.1 (C$^3$ dihydroxypropoxy), 70.4 (C$^2$ dihydroxypropoxy), 70.9 (C$^1$ dihydroxypropoxy), 112.0 (C$^7$), 113.2 (C$^9$), 115.4 (C$^{3'}$), 115.8 (C$^2$), 116.8 (C$^{4'}$), 122.0 (C$^6$), 125.4 (C$^{5a}$), 126.0 (C$^{5'}$), 126.3 (C$^4$), 127.0 (C$^3$), 127.1 (C$^{4a}$), 130.5 (C$^{11a}$), 133.1 (C$^6$), 141.5 (C$^{1'}$), 143.9 (C$^{2'}$), 145.3 (C$^7$), 150.9 (C$^{9a}$), 155.3 (C$^1$), 192.1 (C$^5$).

EXAMPLE 70

8-Chloro-1-(tetrahydropyran-4-yloxy)-10,11-dihydrodibenzo[a,d]cyclohepten-5-one (15)

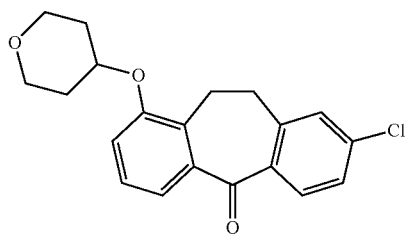 [SMILES: O=C1c2ccc(Cl)cc2CCc2c(OC3CCOCC3)cccc21]

For the synthesis of the title compound, 0.45 g (1.7 mmol) of 8-chloro-1-hydroxy-10,11-dihydrodibenzo[a,d]cyclohepten-5-one, 0.28 g (0.0027 mol) of tetrahydropyran-4-ol, 0.77 g (2.9 mmol) of P(Ph)$_3$ and 0.41 g (2.0 mmol) of diisopropyl azodicarboxylate in 2 ml of THF are reacted by method P. C$_{20}$H$_{19}$ClO$_3$ (Mr=342.83); yield: 45%

$^1$H-NMR (DMSO-d6) δ in ppm: 1.63 (s, 2H, C$^2$—H pyran), 1.91 (s, 2H, C$^6$—H pyran), 3.10 (s, 4H, —CH$_2$—CH$_2$—), 3.48 (s, 2H, C$^3$—H pyran), 3.79 (s, 2H, C$^5$—H pyran), 4.61 (s, 1H, C$^1$—H pyran), 7.05-7.42 (m, 5H, C$^2$—/C$^3$—/C$^4$—/C$^6$—/C$^7$—H), 7.67 (s, 1H, C$^9$—H).

$^{13}$C-NMR (DMSO-d6) δ in ppm: 26.4 (C$^{11}$), 31.9 (2C, C$^2$/C$^6$ pyran), 32.9 (C$^{10}$), 64.6 (2C, C$^3$/C$^5$ pyran), 72.4 (C$^1$ pyran), 118.1 (C$^2$), 122.1 (C$^4$), 127.0 (C$^7$), 127.4 (C$^3$), 129.1 (C$^9$), 131.4 (C$^6$), 137.1 (C$^{4a}$), 138.0 (C$^{5a}$), 139.9 (C$^{11a}$), 143.8 (C$^8$), 154.3 (C$^{9a}$), 156.5 (C$^1$), 195.2 (C$^5$).

EXAMPLE 71

8-(2,4-Difluorophenylamino)-1-(tetrahydropyran-4-yloxy)-10,11-dihydrodibenzo[a,d]cyclohepten-5-one (11 h)

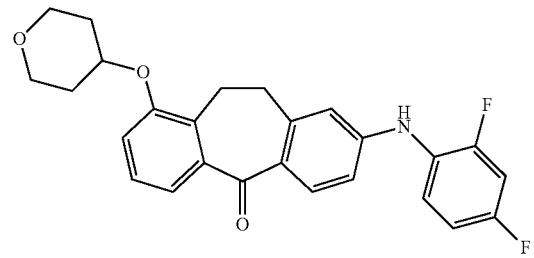 [SMILES: O=C1c2ccc(Nc3ccc(F)cc3F)cc2CCc2c(OC3CCOCC3)cccc21]

For the synthesis of the title compound, 0.45 g (0.0013 mol) of 8-chloro-1-(tetrahydropyran-4-yloxy)-10,11-dihydrodibenzo[a,d]cyclohepten-5-one, 0.17 g (0.0013 mol) of 2,4-difluoroaniline, 2 spatula tips of Pd(OAc)$_2$, 0.14 g of phosphine ligand and 0.70 g (0.0073 mol) of NaOtert-Bu in 10 ml of toluene and 2 ml of tert-BuOH are reacted by method O. Purification is carried out by column chromatography (flash; SiO$_2$; hexane 70%/ethyl acetate 30%).

C$_{26}$H$_{23}$F$_2$NO$_3$ (Mr=435.47); yield: 52%; m.p.: 134° C.

IR (ATR) 3327, 2961, 2857, 1564, 1496, 1300, 1277, 1257, 1243, 1187, 1150, 1131, 1099, 1088, 1005, 957, 858, 833, 813, 769, 630, 577, 550, 508 cm$^{-1}$.

$^1$H-NMR (DMSO-d6) δ in ppm: 1.54-1.71 (m, 2H, C$^2$—H pyran), 1.91-2.00 (m, 2H, C$^6$—H pyran), 2.96-3.12 (m, 4H, —CH$_2$—CH$_2$—), 3.43-3.54 (m, 2H, C$^3$—H pyran), 3.78-3.88 (m, 2H, C$^4$—H pyran), 4.59 (q, 1H, J=3.68 Hz, C$^1$—H pyran), 6.62 (s, 1H, C$^9$—H), 6.71 (d, 1H, J=8.68 Hz, C$^7$—H), 7.03-7.13 (m, 1H, C$^{6'}$—H), 7.22-7.25 (m, 2H, C$^{3'}$—/C$^{6'}$—H), 7.29-7.42 (m, 3H, C$^2$—/C$^3$—/C$^4$—H), 7.82 (d, 1H, J=8.66 Hz, C$^6$—H), 8.48 (s, 1H, —NH—).

$^{13}$C-NMR (DMSO-d6) δ in ppm: 25.3 (s, C$^{11}$), 32.0 (s, 2C, C$^2$/C$^6$ pyran), 35.1 (s, C$^{10}$), 64.7 (s, 2C, C$^3$/C$^5$ pyran), 72.8 (s, C$^1$ pyran), 105.3 (t, J=25.5 Hz, C$^3$), 112.2 (d, J=22.1 Hz, C$^5$), 112.7 (s, C$^7$), 113.9 (s, C$^9$), 117.9 (s, C$^2$), 122.4 (s, C$^4$), 125.4 (d, J=15.7 Hz, C$^{1'}$), 126.2 (d, J=9.5 Hz, C$^{6'}$), 127.1 (s, C$^3$), 128.4 (s, C$^{5a}$), 131.5 (s, C$^{4a}$), 132.9 (s, C$^6$), 141.7 (s, C$^{11a}$), 145.2 (s, C$^8$), 149.2 (s, C$^{9a}$), 155.0 (d, J=141.0 Hz, C$^{4'}$), 153.4 (s, C$^1$), 159.6 (d, J=137.2 Hz, C$^{2'}$), 192.6 (s, C$^5$).

EXAMPLE 72

8-Chloro-1-(2-morpholin-4-yl-ethoxy)-10,11-dihydrodibenzo[a,d]cyclohepten-5-one (16)

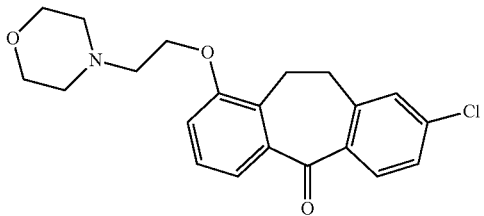 [SMILES: O=C1c2ccc(Cl)cc2CCc2c(OCCN3CCOCC3)cccc21]

For the synthesis of the title compound, 0.44 g (1.69 mmol) of 8-chloro-1-hydroxy-10,11-dihydrodibenzo[a,d]cyclohepten-5-one, 0.345 g (1.86 mmol) of 4-(2-chloroethyl)morpholine hydrochloride and 0.93 g (6.75 mmol) of $K_2CO_3$ in 15 ml of acetonitrile are reacted by method Q. $C_{21}H_{21}ClNO_3$ (Mr=371.87); GC 29.7 min MS m/z (%): 373/371 (1/4, M+), 165 (4,3-methoxy-2-methyl-benzoic acid), 114 (1, ethylmorpholine), 100 (100, 114-$CH_2$), 87 (1, 100-$CH_2$).

IR (ATR) 2854, 1585, 1451, 1282, 1252, 1115, 1090, 1062, 909, 860, 757 cm$^{-1}$ $^1$H-NMR (DMSO-d6) δ in ppm: 2.50 (under DMSO, 4H, $C^2$—/$C^6$—H morpholine), 2.71 (t, 2H, J=5.61 Hz, $C^2$—H ethylmorpholine), 3.09 (s, 4H, —$CH_2$—$CH_2$— cycloheptane), 3.47-3.58 (m, 4H, $C^3$—/$C^5$—H morpholine), 4.12 (t, 2H, J=5.59 Hz, $C^1$—H ethylmorpholine), 7.23-7.70 (m, 6H, $C^2$—/$C^3$—/$C^4$—/$C^6$—/$C^7$—/$C^9$—H).

$^{13}$C-NMR (DMSO-d6) δ in ppm: 26.4 ($C^{11}$), 32.9 ($C^{10}$), 53.9 ($C^2$/$C^6$ morpholine), 57.3 ($C^2$ ethylmorpholine), 66.6 ($C^3$/$C^5$ morpholine), 67.0 ($C^1$ ethylmorpholine), 116.3 ($C^2$), 121.9 ($C^4$), 127.0 ($C^7$), 127.5 ($C^3$), 129.1 ($C^9$), 130.7 ($C^6$), 131.3 ($C^{5a}$), 137.1 ($C^{4a}$), 138.1 ($C^{11a}$), 139.5 ($C^8$), 143.7 ($C^{9a}$), 156.0 ($C^1$), 195.2 ($C^5$).

EXAMPLE 73

8-(2,4-Difluorophenylamino)-1-(2-morpholin-4-yl-ethoxy)-10,11-dihydrodibenzo[a,d]cyclo-hepten-5-one (11j)

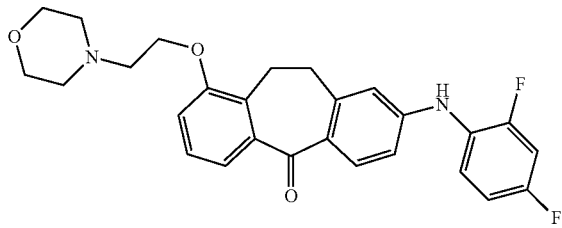 [SMILES: O=C1c2ccc(Nc3ccc(F)cc3F)cc2CCc2c(OCCN3CCOCC3)cccc21]

For the synthesis of the title compound, 0.48 g (0.0013 mol) of 8-chloro-1-(2-morpholin-4-yl-ethoxy)-10,11-dihydrodibenzo[a,d]cyclohepten-5-one, 0.17 g (0.0013 mol) of 2,4-difluoroaniline, 2 spatula tips of Pd(OAc)$_2$, 0.14 g of phosphine ligand and 0.70 g (0.0073 mol) of NaOtert-Bu in 10 ml of toluene and 2 ml of tert-BuOH are reacted by method O. Purification is carried out by column chromatography (flash; SiO$_2$; hexane 60%/ethyl acetate 40%).

$C_{27}H_{26}F_2N_2O_3$ (Mr=464.52)

$^1$H-NMR (DMSO-d6) δ in ppm: 2.49 (under DMSO, 4H $C^2$—/$C^6$—H morpholine), 2.72 (t, 2H, J=5.62 Hz, $C^2$—H ethylmorpholine), 2.99-3.10 (m, 4H, —$CH_2$—$CH_2$— cycloheptane), 3.56 (t, 4H, J=4.58 Hz, $C^3$—/$C^5$—H morpholine), 4.12 (t, 2H, J=5.62 Hz, $C^1$—H ethylmorpholine), 6.62 (s, 1H, $C^9$—H), 6.71 (d, 1H, J=8.68 Hz, $C^7$—H), 7.08-7.41 (m, 6H, $C^2$—/$C^3$—/$C^4$—H and $C^{3'}$—/$C^{6'}$—/$C^{6'}$—H), 7.82 (d, 1H, J=8.67 Hz, $C^6$—H), 8.48 (s, 1H, —NH—).

$^{13}$C-NMR (DMSO-d6) δ in ppm: 25.2 (s, $C^{11}$), 35.1 (s, $C^{10}$), 53.9 (s, 2C, $C^2$/$C^6$ morpholine), 57.4 (s, $C^2$ ethylmorpholine), 66.6 (s, 2C, $C^3$/$C^5$ morpholine), 67.1 (s, $C^1$ ethylmorpholine), 105.3 (dd, J$_1$=26.6 Hz, J$_2$=24.1 Hz, $C^{3'}$), 112.1 (dd, J$_1$=21.8 Hz, J$_2$=3.7 Hz, $C^{5'}$), 112.6 (s, $C^7$), 113.9 (s, $C^9$), 115.8 (s, $C^2$), 122.1 (s, $C^4$), 125.4 (dd, J$_1$=12.1 Hz, J$_2$=3.6 Hz, $C^{1'}$), 126.2 (dd, J$_1$=9.6 Hz, J$_2$=3.2 Hz, $C^{6'}$), 127.2 (s, $C^{5a}$), 128.5 (s, $C^3$), 130.5 (s, $C^{4a}$), 132.9 (s, $C^6$), 141.3 (s, $C^{11a}$), 145.1 (s, $C^8$), 149.2 (s, $C^{9a}$), 154.8 (dd, J$_1$=140.7 Hz, J$_2$=12.6 Hz, $C^{4'}$), 155.1 (s, $C^1$), 159.7 (dd, J$_1$=136.5 Hz, J$_2$=11.8 Hz, $C^{2'}$), 196.6 (s, $C^5$).

EXAMPLE 74

Trifluoromethanesulfonic acid 8-chloro-5-oxo-10,11-dihydro-5H-dibenzo[a,d]cyclohepten-1-yl ester

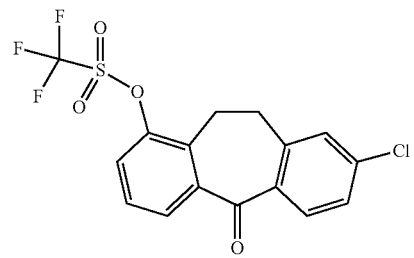 [SMILES: O=C1c2ccc(Cl)cc2CCc2c(OS(=O)(=O)C(F)(F)F)cccc21]

For the preparation of the title compound, 0.517 g (0.0020 mol) of 8-chloro-1-hydroxy-10,11-dihydrodibenzo[a,d]cyclohepten-5-one and 0.846 g (0.0030 mol) of Tf$_2$O in 5 ml of pyridine are reacted by method R. $C_{16}H_{10}ClF_3O_4S$ (Mr=390.77); GC 11.9 min MS m/z (%): 392/390 (39/100, M+), 364/362 (9/24, M+-CO), 259/257 (17/50, M+-SO$_2$CF$_3$), 231/229 (10/31, 259/257-CO), 194 (54, 231/229-Cl).

C. Dibenzooxoepinones Substituted at Position 8

Material and Methods

Melting points: Büchi Melting Point B-545 (thermodynamic correction)

NMR spectroscopy: Bruker Advance 200 (200 MHz)

Internal standard: Tetramethylsilane (TMS), δ [ppm]=0

IR spectroscopy: Perkin Elmer Spectrum One (ATR technique)

TLC: SiO$_2$ 60 F$_{254}$-Alu film, Merck family

GC/MS: Hewlett Packard HP 6890 Series GC-System (column: HP-5MS: 5% phenyl-methyl-siloxane; length: 30.0 m, diameter: 250 μm, film thickness: 0.25 μm; or similar column from other manufacturers Carrier gas: Helium 6.0; flow rate: 1.2 ml/min Hewlett Packard HP 5973 Mass Selective Detector Method 1:

Injection temperature: 250° C.

| Heating rate [K/min] | End temperature [° C.] | Holding time [min] |
|---|---|---|
|  | 100 | 1 |
| 10 | 160 | 10 |
| 15 | 200 | 15 |

Method 2:
Injection temperature: 250° C.

| Heating rate [K/min] | End temperature [° C.] | Holding time [min] |
|---|---|---|
|  | 100 | 1 |
| 10 | 160 | 10 |
| 15 | 200 | 15 |
| 10 | 270 | 20 |

Method 3:
Injection temperature: 250° C.

| Heating rate [K/min] | End temperature [° C.] | Holding time [min] |
|---|---|---|
|  | 160 | 1 |
| 10 | 240 | 5 |
| 10 | 270 | 15 |

Method 3_L:
Injection temperature: 250° C.

| Heating rate [K/min] | End temperature [° C.] | Holding time [min] |
|---|---|---|
|  | 160 | 1 |
| 10 | 240 | 5 |
| 10 | 270 | 30 |

LC/MS:
TSQ Quantum
Surveyor HPLC (Thermo Finnigan, Calif., San Jose)
binary pump/autosampler/PDA detector
coupled to Thermo Finnigan TSQ Quantum triple quadrupole MS General Synthesis Methods General Method S For esterification of the acid group of the starting compound 2-methyl-4-nitro-benzoic acid, the stated amount is dissolved in methanol in a 100 ml one-necked flask at room temperature, concentrated $H_2SO_4$ is added and the mixture is refluxed at approx. 60° C. for 6 h. The excess alcohol is removed in vacuo, the residue is taken up in EtOAc and the mixture is deacidified repeatedly with 20% strength sodium hydroxide solution. After drying ($Na_2SO_4$), the combined organic phases are concentrated in vacuo.

General Method T

The substance to be halogenated is dissolved in carbon tetrachloride in a 250 ml three-necked flask with a reflux condenser and drying tube at approx. 70° C. and the stated amounts of N-bromosuccinimide and azobisisobutyronitrile are added. The mixture is refluxed for 5 h, if necessary with irradiation with a 500 W spotlight. At the end of the reaction, the N-bromosuccinimide has dissolved and has been converted into succinimide, which settles on the surface. After cooling to room temperature, the mixture is filtered with suction. The filtrate is evaporated on a rotary evaporator in order to obtain the product as a yellow-orange oil.

General Method U

For further reaction of the brominated educt with substituted phenols, the stated amount of potassium carbonate is suspended in acetone in a 250 ml three-necked flask. The phenol to be deprotonated is added and the mixture is stirred at room temperature for 15 min. The brominated benzoic acid methyl ester is then added to the mixture and, after heating to 70° C., the mixture is refluxed for 6 h. The acetone is removed in vacuo and the residue is extracted by shaking several times with EtOAc. After acidification of the aqueous phase with 20% strength HCl, the combined organic phases are concentrated in vacuo after drying ($Na_2SO_4$) and the residue is purified by recrystallization with methanol.

General Method V

The carboxylic acid ester to be hydrolyzed is dissolved in methanol in a 100 ml one-necked flask at room temperature, while stirring, and the stated amount of aqueous KOH solution is then added. After heating to 40° C., the mixture is refluxed for 4 h. The excess alcohol is removed in vacuo and the residue is taken up with $H_2O$. Acidification of the aqueous phase with 20% strength HCl and subsequent stirring on ice follow, and the crude product obtained by this procedure is filtered off with suction and dried over calcium chloride.

General Method W

For the synthesis of the ketones, the stated amount of carboxylic acid is suspended in sulfolane in a dry 250 ml three-necked flask under an argon atmosphere and while heating. Polyphosphoric acid is added and the mixture is refluxed at 100° C. for approx. 2 h. After cooling to room temperature, the mixture is poured into 250 ml of ice-water and subsequently stirred at RT. The crude product which has precipitated out is filtered off.

General Method X

The acetylated ring system is dissolved in methanol by heating in a 100 ml one-necked flask with a reflux condenser, and the stated amount of concentrated hydrochloric acid is then added. The reaction mixture is stirred under reflux for 4 h. The mixture is then concentrated in vacuo. Hydrochloric acid (10%) is added to the residue and the mixture is stirred up and then placed on ice, and after waiting until the product has crystallized out completely, this is filtered off.

General Method Y

For reduction of the nitro compound, the stated amount of tin(II) chloride dihydrate is dissolved in ethanol, while stirring. The nitro compound to be reduced is added and the mixture is refluxed at 100° C. for 2 h. After cooling to room temperature, ice-water is added to the mixture and the mixture is rendered alkaline with 20% strength sodium hydroxide solution. Repeated extraction with ethyl acetate is carried out; after drying ($Na_2SO_4$), the combined organic phases are concentrated in vacuo.

General Method Z

The stated amounts of 3-amino-8-nitro-6H-dibenzo[b,e]oxepin-11-one, phosphine ligand, KOt-Bu, tert-butanol, haloaromatic, Pd(OAc)$_2$ are weighed into a dry 100 ml three-necked flask with a reflux condenser, bubble counter and thermometer. The mixture is suspended in toluene (anhydrous) under an argon atmosphere and the suspension is heated to 110° C. and refluxed for 2 h. Hydrolysis with ice-water and repeated extraction with EtOAc are carried out. The combined organic phases are filtered and then concentrated in vacuo. The residue is purified by chromatography.

EXAMPLE 75

2-Methyl-4-nitro-benzoic acid methyl ester (1)

In accordance with general method S, 5.00 g (27.60 mmol) of 2-methyl-4-nitro-benzoic acid are dissolved in 20 ml of methanol, with heating, and 6 ml of concentrated sulfuric acid are added. The mixture is refluxed for 5 h. Yield: 4.90 g (90.9%); melting point: 73.6° C.

$C_9H_9NO_3$ ($M_r$=195.18); GC (method 1) 9.55 min $^1$H-NMR (CDCl$_3$) δ in ppm: 8.19-8.09 (m, 2H, aryl H), 7.99 (d, 1H, J=8.52 Hz, aryl H), 3.87 (s, 3H, —OCH$_3$), 2.59 (s, 3H, —CH$_3$)

$^{13}$C-NMR (CDCl$_3$) δ in ppm: 166.35 (—C=O), 159.29 ($C^4$), 141.79 ($C^2$), 135.14 ($C^1$), 131.43 ($C^6$), 126.06 ($C^3$), 120.48 ($C^5$), 52.37 (—OCH$_3$), 21.50 (—CH$_3$)

IR (ATR) (cm$^{-1}$): 1722, 1523, 1432, 1348, 1260, 1081, 896, 821, 786, 730

MS m/z (%): 195 (70), 164 (100), 134 (21), 118 (29), 63 (15)

EXAMPLE 76

2-Bromomethyl-4-nitro-benzoic acid methyl ester (2)

In accordance with general method T, 4.70 g (24.00 mmol) of (1) are dissolved in 30 ml of carbon tetrachloride, with heating, and 5.00 g (28.00 mmol) of N-bromosuccinimide and 2 spatula tips of azobisisobutyronitrile are then added. The mixture is refluxed for 6 h with irradiation with a 500 W spotlight. On cooling to room temperature, succinimide separates out, and is filtered off. The filtrate is evaporated on a rotary evaporator in order to obtain the product as a yellow oil. Yield: 5.85 g (88.8%)

$C_9H_8BrNO_4$ ($M_r$=274.07); GC (method 3) 7.98 min $^1$H-NMR (CDCl$_3$) δ in ppm: 4.96 (s, 2H, —CH$_2$—Br), 2.71 (s, 3H, —CH$_3$)

MS m/z (%): 274 (100), 193 (38), 178 (46), 147 (12), 132 (18), 88 (9)

EXAMPLE 77

2-(3-Acetylaminophenoxymethyl)-4-nitrobenzoic acid methyl ester (3)

In accordance with general method U, 1.50 g (10.86 mmol) of potassium carbonate are suspended in 15 ml of acetone, 1.80 g (11.90 mmol) of 3-acetamidophenol are then added and the mixture is stirred for 15 min. 2.44 g (8.91 mmol) of (2) are added to the mixture.

Yield: 1.33 g (43.3%); melting point: 139.2° C.

$C_{17}H_{16}N_2O_6$ ($M_r$=344.33); GC (method 3) 23.07 min $^1$H-NMR (DMSO-$_{d6}$) δ in ppm: 9.95 (s, 1H, —NH), 8.45 (d, 1H, J=1.98 Hz, aryl H), 8.27 (m, 1H, aryl H), 8.12 (d, 1H, J=8.54 Hz, aryl H), 7.37 (s, 1H, aryl H), 7.21-7.16 (m, 2H, aryl H), 6.71-6.68 (m, 1H, aryl H), 5.44 (s, 2H, —CH$_2$—O), 3.86 (s, 3H, —O—CH$_3$)

$^{13}$C-NMR (DMSO-$_{d6}$) δ in ppm: 168.75 (—NH—C=O—), 166.00 (—C=O), 158.41 ($C^1$), 149.75 ($C^4$), 141.00 ($C^2$), 140.77 ($C^3$), 134.48 ($C^1$), 132.10 ($C^6$), 130.02 ($C^5$), 123.08 ($C^3$), 122.64 ($C^5$), 112.37 ($C^{4'}$), 109.49 ($C^{6'}$), 105.94 ($C^{2'}$), 65.01 (—CH$_2$—O), 52.16 (—O—CH$_3$), 24.41 (—NH=O—CH$_3$)

IR (ATR) (cm$^{-1}$): 1729, 1719, 1606, 1349, 1289, 1253, 1158, 1057, 771, 727

MS m/z (%): 344 (10), 327 (10), 271 (3), 194 (100), 148 (44)

EXAMPLE 78

2-(3-Acetylaminophenoxymethyl)-4-nitrobenzoic acid (4)

In accordance with general method V, 1.30 g (3.78 mmol) of (3) are dissolved in 20 ml of methanol, and 0.70 g (12.50 mmol) of KOH are added. Yield 1.20 g (96.1%); melting point: 225.0° C.; $C_{167}H_{14}N_2O_6$ ($M_r$=330.30)

$^1$H-NMR (DMSO-$_{d6}$) δ in ppm: 9.96 (s, 1H, —COOH), 8.42 (d, 1H, J=2.06 Hz, aryl H), 8.26 (dd, 1H, J$_1$=8.52 Hz, J$_2$=2.38 Hz, aryl H), 8.13 (d, 1H, J=8.00 Hz, aryl H), 7.37 (s, 1H, aryl H), 7.26-7.14 (m, 2H, aryl H), 6.72-6.66 (m, 1H, aryl H), 5.47 (s, 2H, —CH$_2$—O), 2.01 (s, 3H, —CH$_3$)

$^{13}$C-NMR (DMSO-$_{d6}$) δ in ppm: 168.74 (—COOH), 167.14 (—NH—C=O), 158.46 ($C^{1'}$), 149.58 ($C^4$), 141.00 ($C^2$), 140.81 ($C^{3'}$), 135.63 ($C^1$), 132.27 ($C^6$), 130.02 ($C^{5'}$), 122.89 ($C^3$), 122.28 ($C^5$), 112.30 ($C^{4'}$), 109.55 ($C^{6'}$), 105.90 ($C^{2'}$), 67.10 (—CH$_2$—O—), 24.40 (—NH—C=O—CH$_3$)

IR (ATR) (cm$^{-1}$): 1732, 1603, 1520, 1487, 1343, 1284, 1159, 1053, 767, 733

EXAMPLE 79

3-Acetamido-8-nitro-6H-dibenzo[b,e]oxepin-11-one (5)

In accordance with general method W, 0.80 g (2.42 mmol) of (4) is partly dissolved in 10 ml of sulfolane at 100° C. 15 ml (30.0 g) of polyphosphoric acid are then added to the reaction mixture. Yield: 0.50 g (66.2%); melting point: 171.4° C.

$C_{16}H_{12}N_2O_5$ ($M_r$=312.28); LC 18.62 min $^1$H-NMR (DMSO-$_{d6}$) δ in ppm: 9.95 (s, 1H, —NH), 8.42 (d, 1H, J=2.32 Hz, aryl H), 8.51 (dd, 1H, J$_1$=17.4 Hz, J$_2$=2.36 Hz, aryl H), 8.13 (d, 1H, J=8.56 Hz, aryl H), 7.36 (s, 1H, aryl H), 7.21 (s, 1H, aryl H), 7.17 (s, 1H, aryl H), 6.72-6.66 (m, 1H, aryl H), 5.47 (s, 2H, —CH$_2$—O)

IR (ATR) (cm$^{-1}$): 1670, 1580, 1526, 1406, 1344, 1294, 1247, 905, 740, 708

MS (ESI) 312.9 [M+H]$^+$

EXAMPLE 80

3-Amino-8-nitro-6H-dibenzo[b,e]oxepin-11-one (6)

In accordance with general method X, 0.70 g (2.24 mmol) of (5) is dissolved in 25 ml of methanol, and 8.0 ml of concentrated sal acid are added. Yield: 0.40 g (66.1%); melting point: 59.0° C.; $C_{14}H_{10}N_2O_4$ ($M_r$=270.25); GC (method 3) 20.74 min $^1$H-NMR (DMSO-$_{d6}$) δ in ppm: 8.45 (d, 1H, J=2.10 Hz, aryl H), 8.30 (dd, 1H, J$_1$=2.54 Hz, J$_2$=2.35 Hz, aryl H), 7.99 (d, 1H, J=8.58 Hz, aryl H), 7.87 (d, 1H, J=8.90 Hz, aryl H), 6.42 (dd, 1H, J$_1$=2.89 Hz, J$_2$=2.14 Hz, aryl H), 6.10 (d, 1H, J=2.0 Hz, aryl H), 5.29 (s, 2H, —CH$_2$—O)

$^{13}$C-NMR (DMSO-$_{d6}$) δ in ppm: 185.21 ($C^{11}$), 163.65 ($C^{4a}$), 162.24 ($C^3$), 157.01 ($C^8$), 154.81 ($C^{6a}$), 137.84 ($C^{10a}$), 134.01 ($C^1$), 131.02 ($C^{10}$), 123.91 ($C^7$), 123.38 ($C^9$), 114.37 ($C^{11a}$), 110.98 ($C^2$), 100.98 ($C^4$), 71.90 ($C^6$)

IR (ATR) (cm$^{-1}$): 2790, 2565, 1644, 1608, 1531, 1297, 1250, 1150, 1085, 907, 819, 708

MS m/z (%): 270 (100), 241 (13), 224 (14), 195 (22), 167 (19), 139 (10), 83 (9), 63 (9)

EXAMPLE 81

3-(2,4-Difluorophenylamino)-8-nitro-6H-dibenzo[b,e]oxepin-11-one (7)

In accordance with general method Z, 0.50 g (1.85 mmol) of (6), 0.28 g (1.89 mmol) of 1-chloro-2,4-difluorobenzene, 2 spatula tips of Pd(OAc)$_2$, 0.09 g of 2-(dicyclohexylphosphino)-2',4',6'-triisopropylbiphenyl (phosphine ligand), 0.50 g of KOt-Bu, 1.5 ml of t-BuOH are weighed out and dissolved in 10 ml of toluene (anhydrous). The mixture is refluxed at 100° C. under an argon atmosphere for 4 h. The crude product is purified by chromatography over silica gel with MC/EtOH (98/2). Yield: 0.05 g (7.0%); melting point: 210-214° C.

$C_{20}H_{12}F_2N_2O_4$ ($M_r$=382.33); LC 8.97 min $^1$H-NMR (DMSO-$_{d6}$) δ in ppm: 8.84 (s, 1H, aryl H), 8.48 (d, 1H, J=2.01 Hz, aryl H), 8.30 (m, 1H, aryl H), 8.01 (dd, 2H, $J_1$=2.70 Hz, $J_2$=3.25 Hz, aryl H), 7.47-7.33 (m, 2H, aryl H), 7.15-7.04 (m, 2H, aryl H), 6.63 (d, 1H, J=10.0 Hz, aryl H), 6.24 (s, 1H, aryl H), 5.34 (s, 2H, —CH$_2$—O)

$^{13}$C-NMR (DMSO-$_{d6}$) δ in ppm: 186.11 ($C^{11}$), 163.30 ($C^{4a}$), not detected (C4', C2'), 152.89 ($C^8$), 149.52 ($C^3$), 145.34 ($C^{6a}$), 137.76 ($C^{10a}$), 133.85 ($C^1$), 131.01 ($C^{10}$), 127.38 ($C^{1'}$, J=9.85 Hz), 124.23 ($C^{6'}$, J=14.23 Hz), 116.52 ($C^7$), 112.57 ($C^{5'}$, J=3.52 Hz), 110.35 ($C^2$), 105.45 ($C^{3'}$, J=24.29 Hz), 101.93 ($C^4$), 72.03 ($C^6$)

IR (ATR) (cm$^{-1}$): 2849, 1643, 1608, 1531, 1297, 1249, 1150, 740

MS (ESI) 381.1 [M–H]$^-$

EXAMPLE 82

3-(2,4-Difluorophenylamino)-8-amino-6H-dibenzo[b,e]oxepin-11-one (8)

In accordance with general method Y, 0.10 g (0.44 mmol) of tin(II) chloride dihydrate is dissolved in 7 ml of ethanol, and 0.45 g (0.11 mmol) of (7) is added. Yield: 0.035 g (90.3%); melting point: 184-193° C.; $C_{20}H_{14}F_2N_2O_2$ ($M_r$=282.30); LC 7.76 min $^1$H-NMR (DMSO-$_{d6}$) δ in ppm: 8.60 (s, 1H, —NH), 8.01 (d, 1H, J=10.00 Hz, aryl H), 7.66 (d, 1H, J=8.0 Hz, aryl H), 7.46-7.30 (m, 2H, aryl H), 7.13-7.04 (m, 1H, aryl H), 6.58 (d, 2H, J=12.0 Hz, aryl H), 6.55 (s, 1H, aryl H), 6.46 (s, 1H, aryl H), 6.06 (s, 2H, —NH$_2$), 4.97 (s, 2H, —CH$_2$—O)

$^{13}$C-NMR (DMSO-$_{d6}$) δ in ppm: 184.59 ($C^{11}$), 162.65 ($C^{4a}$), not detected ($C^{4'}$, $C^{2'}$) 153.51 ($C^8$), 151.07 ($C^3$), 139.19 ($C^{6a}$), 133.86 ($C^1$), 132.47 ($C^{10}$), 127.02 ($C^9$), 126.99 ($C^{1'}$), 125.55 ($C^{6'}$), 118.32 ($C^{10a}$), 113.50 ($C^7$), 111.67 ($C^{5'}$), 109.85 ($C^2$), 105.32 ($C^{3'}$), 102.56 ($C^4$), 74.41 ($C^6$)

IR (ATR) (cm$^{-1}$): 1613, 1586, 1557, 1523, 1402, 1324, 1312, 1281, 1258, 1115, 816

MS (ESI) 353.2 [M+H]$^+$

EXAMPLE 83

3-(2-Nitrophenylamino)-8-nitro-6H-dibenzo[b,e]oxepin-11-one (9)

In accordance with general method Z, 1.00 g (3.70 mmol) of (6), 0.80 g (3.96 mmol) of 1-bromo-2-nitrobenzene, 2 spatula tips of Pd(OAc)$_2$, 0.10 g of 2-(dicyclohexylphosphino)-2',4',6'-triisopropylbiphenyl (phosphine ligand), 0.70 g of KOt-Bu, 2.0 ml of t-BuOH are weighed out and dissolved in 10 ml of toluene (anhydrous). The mixture is refluxed at 100° C. under an argon atmosphere for 4 h. The crude product is purified by chromatography over silica gel with MC/EtOH (98/2). Yield 0.35 g (24.2%); melting point: 212.5° C.

$C_{20}H_{13}N_3O_6$ ($M_r$=391.34); LC9.18 min $^1$H-NMR (DMSO-$_{d6}$) δ in ppm: 9.34 (s, 1H, —NH), 8.50 (d, 1H, J=2.24 Hz, aryl H), 8.34 (dd, 1H, $J_1$=2.39 Hz, $J_2$=2.40 Hz, aryl H), 8.10-7.98 (m, 3H, aryl H), 7.66-7.56 (m, 2H, aryl H), 7.25 (t, 1H, $J_1$=1.6 Hz, $J_2$=6.8 Hz, aryl H), 6.97 (dd, 1H, $J_1$=2.04 Hz, $J_2$=2.23 Hz, aryl H), 6.71 (s, 1H, aryl H), 5.39 (s, 2H, —CH$_2$—O)

$^{13}$C-NMR (DMSO-$_{d6}$) δ in ppm: 184.34 ($C^{11}$), 162.90 ($C^{4a}$), 149.93 ($C^8$), 149.69 ($C^3$), 145.19 ($C^{6a}$), 137.69 ($C^{10a}$), 136.34 ($C^{1'}$), 135.45 ($C^{5'}$), 134.08 ($C^{2'}$), 133.68 ($C^1$), 130.99 ($C^{10}$), 128.40 ($C^{3'}$ and $C^{7}$), 126.40 ($C^{6'}$), 123.66 ($C^9$), 123.33 ($C^{4'}$), 118.55 ($C^{11a}$), 112.45 ($C^2$), 106.36 ($C^4$), 72.34 ($C^6$)

IR (ATR) (cm$^{-1}$): 1642, 1595, 1582, 1500, 1356, 1340, 1269, 1248, 1226, 1152, 1131, 1034, 736

MS (ESI) 390.3 [M–H]$^-$

EXAMPLE 84

3-(2-Aminophenylamino)-8-amino-6H-dibenzo[b,e]oxepin-11-one (10)

In accordance with general method Y, 2.40 g (10.66 mmol) of tin(II) chloride dihydrate are dissolved in 15 ml of ethanol, and 0.35 g (0.89 mmol) of (9) is added. Yield: 0.20 g (67.9%); melting point: 203.9° C.; $C_{20}H_{17}N_3O_2$ ($M_r$=331.38); LC 7.05 min $^1$H-NMR (MeOH-$_{d4}$) δ in ppm: 8.09 (d, 1H, J=9.0 Hz, aryl H), 7.78 (d, 1H, J=8.55 Hz, aryl H), 7.09-7.00 (m, 2H, aryl H), 6.89-6.88 (m, 1H, aryl H), 6.71-6.64 (m, 2H, aryl H), 6.55-6.49 (m, 2H, aryl H), 6.14 (d, 1H, J=2.26 Hz, aryl H), 4.97 (s, 2H, —CH$_2$—O)

$^{13}$C-NMR (MeOH-$_{d4}$) δ in ppm: 186.65 ($C^{11}$), 163.58 ($C^{4a}$), 153.31 ($C^8$), 153.12 ($C^3$), 143.31 ($C^{6a}$), 139.37 ($C^{1'}$), 133.34 ($C^1$), 131.97 ($C^{10}$), 127.65 ($C^{6'}$), 126.51 ($C^{2'}$), 125.66 ($C^{10a}$), 117.775 ($C^{5'}$), 116.89 ($C^{11a}$), 115.96 ($C^4$), 113.34 ($C^9$), 111.46 ($C^{3'}$), 109.27 ($C^2$), 101.14 ($C^4$), 73.99 ($C^6$)

IR (ATR) (cm$^{-1}$): 1601, 1579, 1550, 1497, 1291, 1267, 1228, 1112, 828, 757, 747

MS (ESI) 332.9 [M+H]$^+$

EXAMPLE 85

3-(4-Fluoro-2-nitrophenylamino)-8-nitro-6H-dibenzo[b,e]oxepin-11-one (11)

In accordance with general method Z, 0.85 g (3.14 mmol) of (6), 0.70 g (3.19 mmol) of 1-bromo-4-fluoro-2-nitrobenzene, 2 spatula tips of Pd(OAc)$_2$, 0.10 g of 2-(dicyclohexylphosphino)-2',4',6'-triisopropylbiphenyl (phosphine ligand), 0.70 g of KOt-Bu, 2.0 ml of t-BuOH are weighed out and dissolved in 10 ml of toluene (anhydrous). The mixture is refluxed at 100° C. under an argon atmosphere for 4 h. The crude product is purified by chromatography over silica gel with MC/EtOH (98/2). Yield: 0.10 g (7.8%); melting point 210.7° C.

$C_{20}H_{12}FN_2O_4$ ($M_r$=409.33); LC 9.15 min $^1$H-NMR (DMSO-$_{d6}$) δ in ppm: 9.22 (s, 1H, —NH), 8.48 (d, 1H, J=6.86 Hz, aryl H), 8.32 (d, 1H, J=9.10 Hz, aryl H), 8.10-8.09 (m, 3H, aryl H), 8.04-7.98 (m, 2H, aryl H), 6.87 (d, 1H, J=9.36 Hz, aryl H), 6.59 (s, 2H, —CH$_2$—O)

$^{13}$C-NMR (DMSO-$_{d6}$) δ in ppm: 186.67 ($C^{11}$), 163.01 ($C^{4a}$), 161.01 ($C^{4'}$, J=251.75 Hz), 150.73 ($C^8$), 149.67 ($C^3$), 145.22 ($C^{6a}$), 141.37 ($C^{2'}$, J=7.30 Hz), 137.71 ($C^{10a}$), 133.77 ($C^1$), 132.56 (C1'), 131.00 ($C^{10}$), 124.19 ($C^{5'}$), 123.66 ($C^7$), 123.15 ($C^6$), 122.70 ($C^9$), 118.18 ($C^{11a}$), 113.03 ($C^{3'}$, J=23.44 Hz), 112.23 ($C^2$), 105.28 ($C^4$), 72.03 ($C^6$)

IR (ATR) (cm$^{-1}$): 1585, 1531, 1516, 1308, 1264, 1246, 1138, 1036, 890, 872, 815

MS (ESI) 408.3 [M–H]$^-$

EXAMPLE 86

3-(2-Amino-4-fluorophenylamino)-8-nitro-6H-dibenzo[b,e]oxepin-11-one (12)

In accordance with general method Y, 0.60 g (2.66 mmol) of tin(II) chloride dihydrate is dissolved in 10 ml of ethanol, and 0.10 g (0.89 mmol) of (11) is added. Yield: 0.01 g (11.9%);

melting point: 194.5° C.; $C_{20}H_{16}FN_3O_2$ ($M_r$=349.37); LC 7.34 min $^1$H-NMR (MeOH-$_{d4}$) δ in ppm: 8.08 (d, 1H, J=8.97 Hz, aryl H), 7.77 (d, 1H, J=8.96 Hz, aryl H), 7.07-6.96 (m, 1H, aryl H), 6.69-6.38 (m, 5H, aryl H), 6.07 (s, 1H, aryl H), 4.97 (s, 2H, —CH$_2$—O)

$^{13}$C-NMR (MeOH-$_{d4}$) δ in ppm: 186.68 ($C^{11}$), 163.57 ($C^{4a}$), 155.84 ($C^{4'}$, J=217.20 Hz), 153.68 ($C^8$), 149.21 ($C^3$), 139.15 ($C^{6a}$), 133.41 ($C^1$), 131.81 ($C^{10}$), 130.23 ($C^{1'}$), 128.66 ($C^{6'}$, J=11.6 Hz), 116.88 ($C^{11a}$), 115.34 ($C^9$), 113.61 ($C^7$), 109.27 ($C^2$), 105.34 ($C^{5'}$, J=24.45 Hz), 103.03 ($C^{3'}$, J=23.18 Hz), 101.15 ($C^4$), 73.67 ($C^6$)

IR (ATR) (cm$^{-1}$): 1602, 1579, 1551, 1505, 1293, 1265, 1233, 1161, 1113, 831, 759

MS (ESI) 350.5 [M+H]$^+$

EXAMPLE 87

3-(2-Methoxyphenylamino)-8-nitro-6H-dibenzo[b,e]oxepin-11-one (14)

In accordance with general method Z, 0.80 g (2.96 mmol) of (6), 0.70 g (3.80 mmol) of 2-bromoanisole, 2 spatula tips of Pd(OAc)$_2$, 0.10 g of 2-(dicyclohexylphosphino)-2',4',6'-triisopropylbiphenyl (phosphine ligand), 0.50 g of KOt-Bu, 2.0 ml of t-BuOH are weighed out and dissolved in 10 ml of toluene (anhydrous). The mixture is refluxed at 100° C. under an argon atmosphere for 4 h. The crude product is purified by chromatography over silica gel with MC/EtOH (98/2). Yield: 0.025 g (2.2%); melting point: 200.3° C.

$C_{21}H_{16}N_2O_6$ ($M_r$=376.37); LC 9.03 min $^1$H-NMR (DMSO-$_{d6}$) δ in ppm: 8.55 (s, 1H, aryl H), 8.47 (d, 1H, J=2.31 Hz, aryl H), 8.30 (dd, 1H, J$_1$=2.47 Hz, J$_2$=2.41 Hz, aryl H), 8.02-7.92 (m, 2H, aryl H), 7.27-7.23 (m, 1H, aryl H), 7.16-7.10 (m, 2H, aryl H), 6.99-6.95 (m, 1H, aryl H), 6.69 (dd, 1H, J$_1$=3.07 Hz, J$_2$=2.26 Hz, aryl H), 6.32 (d, 1H, J=2.19 Hz, aryl H), 5.32 (s, 2H, —CH$_2$—O), 3.78 (s, 3H, —O—CH$_3$)

$^{13}$C-NMR (DMSO-$_{d6}$) δ in ppm: 185.73 ($C^{11}$), 163.30 ($C^{4a}$), 153.28 ($C^8$), 152.84 ($C^{2'}$), 149.43 ($C^3$), 145.46 ($C^{6a}$), 137.82 ($C^{10a}$), 133.60 ($C^1$), 131.02 ($C^{10}$), 128.68 ($C^{1'}$), 125.78 ($C^9$), 124.06 ($C^7$), 123.51 ($C^{5'}$), 121.00 ($C^4$), 115.96 ($C^{11a}$), 112.60 ($C^{3'}$), 110.67 ($C^4$), 71.98 (—O—CH$_2$), 55.84 (—O—CH$_3$)

IR (ATR) (cm$^{-1}$): 3410, 1622, 1593, 1520, 1343, 1296, 1235, 1027, 768, 761, 742

MS (ESI) 377.4 [M+H]$^+$

EXAMPLE 88

8-Amino-3-(2-methoxyphenylamino)-6H-dibenzo[b,e]oxepin-11-one (15)

In accordance with general method Y, 0.10 g (0.44 mmol) of tin(II) chloride dihydrate is dissolved in 15 ml of ethanol, and 0.04 g (0.10 mmol) of (14) is added. Yield: 0.0046 g (13.3%); melting point: 68.4° C.; $C_{21}H_{18}N_2O_3$ ($M_r$=346.39); LC 18.55 min $^1$H-NMR (DMSO-$_{d6}$) δ in ppm: 8.52 (s, 1H, aryl H), 8.32 (d, 1H, J=5.19 Hz, aryl H), 7.98 (d, 1H, J=6.31 Hz, aryl H), 7.85-7.24 (m, 4H, aryl H), 6.70-6.19 (m, 4H, aryl H), 5.95 (s, 2H, —NH$_2$), 4.96 (s, 2H, —CH$_2$—O), 3.78 (s, 3H, —OCH$_3$)

$^{13}$C-NMR (DMSO-$_{d6}$) δ in ppm: 184.50 ($C^{11}$), 162.65 ($C^{4a}$), 153.38 ($C^8$), 152.30 ($C^{2'}$), 151.29 ($C^3$), 139.20 ($C^{6a}$), 133.61 ($C^1$), 132.44 ($C^{10}$), 129.51 ($C^{1'}$), 127.17 ($C^{10a}$), 124.77 ($C^{5'}$), 122.91 ($C^{6'}$), 120.93 ($C^4$), 117.81 ($C^{11a}$), 113.47 ($C^{3'}$), 112.43 ($C^9$), 111.66 ($C^7$), 110.19 ($C^2$), 102.65 ($C^4$), 74.34 ($C^6$), 55.81 (—OCH$_3$)

MS (ESI) 347.3 [M+H]$^+$

EXAMPLE 89

8-Nitro-3-(4-fluoro-2-methoxyphenylamino)-6H-dibenzo[b,e]oxepin-11-one (16)

In accordance with general method Z, 0.70 g (2.60 mmol) of (6), 0.55 g (2.68 mmol) of 2-bromo-5-fluoroanisole, 2 spatula tips of Pd(OAc)$_2$, 0.10 g of 2-(dicyclohexylphosphino)-2',4',6'-triisopropylbiphenyl (phosphine ligand), 0.50 g of KOt-Bu, 2.0 ml of t-BuOH are weighed out and dissolved in 10 ml of toluene (anhydrous). The mixture is refluxed at 100° C. under an argon atmosphere for 4 h. The crude product is purified by chromatography over silica gel with MC/EtOH (98/2). Yield: 0.07 g (0.01%); melting point: 222.3° C.

$C_{21}H_{15}FN_2O_5$ ($M_r$=394.36); LC 8.90 min $^1$H-NMR (DMSO-$_{d6}$) δ in ppm: 8.64-8.27 (m, 3H, aryl H), 8.20-7.92 (m, 2H, aryl H), 7.24-7.01 (m, 2H, aryl H), 6.87-6.58 (m, 2H, aryl H), 5.75 (s, 1H, —NH), 5.31 (s, 2H, —CH$_2$—O), 3.94 (s, 3H, —OCH$_3$)

$^{13}$C-NMR (DMSO-$_{d6}$) δ in ppm: 185.72 ($C^{11}$), 163.34 ($C^{4a}$), 160.42 ($C^{4'}$, J=241.23 Hz), 154.77 ($C^{2'}$, J=10.51 Hz), 153.84 ($C^8$), 149.40 ($C^3$), 145.45 ($C^{6a}$), 137.80 ($C^{10a}$), 133.66 ($C^1$), 131.01 ($C^{10}$), 126.29 ($C^{6'}$, J=10.16 Hz), 124.81 ($C^{1'}$, J=30.68 Hz), 124.01 ($C^7$), 123.49 ($C^9$), 115.80 ($C^{11a}$), 110.29 ($C^2$), 106.96 ($C^{5'}$, J=22.03 Hz), 101.05 ($C^{3'}$, J=26.81 Hz), not detected ($C^4$), 71.98 ($C^6$), 56.34 (—OCH$_3$)

IR (ATR) (cm$^{-1}$): 3314, 1613, 1552, 1510, 1307, 1279, 1235, 1151, 1189, 957, 829, 816

MS (ESI) 395.3 [M+H]$^+$

EXAMPLE 90

8-Amino-3-(4-fluoro-2-methoxyphenylamino)-6H-dibenzo[b,e]oxepin-11-one (17)

In accordance with general method Y, 0.30 g (1.32 mmol) of tin(II) chloride dihydrate is dissolved in 15 ml of ethanol, and 0.07 g (0.19 mmol) of (16) is added. Yield: 0.042 g (60.6%); melting point: 38.9° C.; $C_{21}H_{17}FN_2O_3$ ($M_r$=364.38); LC 18.82 min H-NMR (DMSO-$_{d6}$) δ in ppm: 8.17 (s, 1H, aryl H), 7.98 (d, 1H, J=14.89 Hz, aryl H), 7.64 (d, 1H, J=11.40 Hz, aryl H), 7.27-7.19 (m, 1H, aryl H), 7.04-6.98 (m, 1H, aryl H), 6.81-6.72 (m, 1H, aryl H), 6.59-6.46 (m, 3H, aryl H), 6.05 (s, 1H, —NH), 5.97 (s, 2H, —NH$_2$), 4.95 (s, 2H, —CH$_2$—O), 3.78 (s, 3H, —OCH$_3$)

$^{13}$C-NMR (DMSO-$_{d6}$) δ in ppm: 184.49 ($C^{11}$), 162.70 ($C^{4a}$), 159.92 ($C^{4'}$, J=240.08 Hz), 154.35 ($C^{2'}$, J=10.41 Hz), 153.37 ($C^8$), 151.98 ($C^3$), 139.18 ($C^{6a}$), 133.67 ($C^1$), 132.43 ($C^{10}$), 127.15 ($C^{10a}$), 125.59 ($C^{6'}$, J=3.07 Hz), 125.28 ($C^{1'}$), 117.58 ($C^{11a}$), 113.46 ($C^9$), 111.65 ($C^7$), 109.72 ($C^2$), 106.81 ($C^{5'}$, J=21.98 Hz), 101.99 ($C^4$), 100.92 ($C^{3'}$, J=26.96 Hz), 74.33 ($C^6$), 56.29 (—OCH$_3$)

IR (ATR) (cm$^{-1}$): 3329, 2923, 1599, 1584, 1520, 1268, 1229, 1110, 1028, 949, 832

MS (ESI) 365.2 [M+H]$^+$

EXAMPLE 91

8-Nitro-3-(2-nitro-4-trifluoromethylphenylamino)-6H-dibenzo[b,e]oxepin-11-one (18)

In accordance with general method Z, 0.70 g (2.60 mmol) of (6), 0.55 g (3.05 mmol) of 4-chloro-3-nitro-benzotrifluoride, 2 spatula tips of Pd(OAc)$_2$, 0.10 g of 2-(dicyclohexylphosphino)-2',4',6'-triisopropylbiphenyl (phosphine ligand), 0.50 g of KOt-Bu, 2.0 ml of t-BuOH are weighed out and dissolved in 10 ml of toluene (anhydrous). The mixture is refluxed at 100° C. under an argon atmosphere for 4 h. The crude product is purified by chromatography over silica gel with n-hexane/ethyl acetate (5/2). Yield: 0.047 g (3.9%); melting point: 196.3° C.

$C_{21}H_{12}F_3N_3O_6$ (M$_r$=459.34); LC: 9.67 min $^1$H-NMR (DMSO-$_{d6}$) δ in ppm: 9.74 (s, 1H, —NH), 8.54 (s, 1H, aryl H), 8.37-8.31 (m, 2H, aryl H), 8.11-7.99 (m, 2H, aryl H), 7.90 (d, 1H, J=9.30 Hz, aryl H), 7.13 (d, 1H, J=8.08 Hz, aryl H), 6.98 (s, 1H, aryl H), 5.45 (s, 2H, —CH$_2$—O)

$^{13}$C-NMR (DMSO-$_{d6}$) δ in ppm: 187.42 ($C^{11}$), 162.55 ($C^{4a}$), 149.84 ($C^8$), 147.66 ($C^3$), 145.08 ($C^1$), 141.09 ($C^{6a}$), 137.64 ($C^{2'}$), 136.89 ($C^{10a}$), 133.52 ($C^5$), 131.72 ($C^{10}$), 130.98 ($C^{1'}$), 124.32 ($C^9$), 123.77 ($C^7$), 121.73 (CF$_3$), 121.33 ($C^{3'}$), 120.65 ($C^{4'}$), 120.32 ($C^{6'}$), 120.00 ($C^{11a}$), 115.32 ($C^2$), 110.32 ($C^4$), 72.04 ($C^6$)

IR (ATR) (cm$^{-1}$): 3324, 1636, 1603, 1574, 1531, 1324, 1150, 1112, 1083, 914, 819, 709

MS (ESI) 458.6 [M–H]$^-$

EXAMPLE 92

8-Amino-3-(2-amino-4-trifluoromethylphenylamino)-6H-dibenzo[b,e]oxepin-11-one (19)

In accordance with general method Y, 0.30 g (1.32 mmol) of tin(II) chloride dihydrate is dissolved in 15 ml of ethanol, and 0.095 g (0.20 mmol) of (18) is added. Yield: 0.061 g (76.4%); melting point: 93.9° C.; $C_{21}H_{16}F_3N_3O_2$ (M$_r$=399.38); LC 19.06 min $^1$H-NMR (DMSO-$_{d6}$) δ in ppm: 8.14 (s, 1H, aryl H), 8.00 (d, 1H, J=8.90 Hz, aryl H), 7.65 (d, 1H, J=8.53 Hz, aryl H), 7.20 (d, 1H, J=8.12 Hz, aryl H), 7.06 (s, 1H, aryl H), 6.85 (d, 1H, J=8.57 Hz, aryl H), 6.62-6.55 (m, 2H, aryl H), 6.45 (s, 1H, aryl H), 6.23 (d, 1H, J=2.04 Hz, aryl H), 6.05 (s, 2H, —NH$_2$), 5.31 (s, 2H, —NH$_2$), 4.96 (s, 2H, —CH$_2$—O)

$^{13}$C-NMR (DMSO-$_{d6}$) δ in ppm: 184.61 ($C^{11}$), 162.66 ($C^{4a}$), 153.44 ($C^8$), 151.07 ($C^3$), 143.35 ($C^1$), not detected ($C^{6a}$) 139.20 ($C^{2'}$), 133.79 ($C^{1'}$), 132.47 ($C^{10}$), 129.17 (CF$_3$), 127.06 ($C^{4'}$), 125.45 ($C^5$), 124.47 ($C^{6'}$), 118.09 ($C^{11a}$), 113.50 (C9), 113.01 ($C^{3'}$), 111.70 ($C^7$), 110.33 ($C^2$), 102.90 ($C^4$), 74.39 ($C^6$)

IR (ATR) (cm$^{-1}$): 3352, 1599, 1521, 1334, 1293, 1231, 1160, 1116, 917, 815 MS 400.3 [M+H]$^+$

EXAMPLE 93

3-(Tetrazol-1-yl)-8-nitro-6H-dibenzo[b,e]oxepin-11-one (20)

0.50 g (1.85 mmol) of (6) and 0.35 g (5.38 mmol) of sodium azide are suspended in 2.20 g (14.84 mmol) of trimethyl orthoformate at 0° C. 1.20 g (20.00 mmol) of glacial acetic acid are then added to the mixture and the mixture is heated to 100° C. and refluxed for 4 h. After cooling to room temperature, the mixture is concentrated in vacuo and the residue is taken up with EtOAc and dissolved under the influence of heat. The white-grey product precipitates out in the cold. Yield: 0.50 g (83.6%); melting point: 123-126° C.; $C_{15}H_9N_5O_4$ (M$_r$=323.27)

$^1$H-NMR (DMSO-$_{d6}$) δ in ppm: 10.27 (s, 1H, tetrazole), 8.59 (s, 1H, aryl H), 8.39-8.30 (m, 2H, aryl H), 8.03 (d, 1H, J=8.62 Hz, aryl H), 7.85-7.80 (m, 2H, aryl H), 5.60 (s, 2H, —CH$_2$—O)

$^{13}$C-NMR (DMSO) δ in ppm: 188.40 ($C^{11}$), 161.95 ($C^{4a}$), 150.21 ($C^8$), 144.68 (tetrazole), 137.54 ($C^{10a}$), 133.19 ($C^{10}$), 131.19 ($C^1$), 125.02 ($C^7$), 124.55 ($C^2$), 124.00 ($C^{11a}$), 114.81 ($C^9$), 112.81 ($C^4$), 70.01 ($C^6$)

EXAMPLE 94

8-Amino-3-(tetrazol-1-yl)-6H-dibenzo[b,e]oxepin-11-one (21)

In accordance with general method Y, 1.50 g (6.66 mmol) of tin(II) chloride dihydrate are dissolved in 10 ml of ethanol, and 0.50 g (1.54 mmol) of (20) is added.

Yield: 0.027 g (6.1%); melting point: 277.0° C.; $C_{15}H_{11}N_5O_2$ (M$_r$=293.29)

$^1$H-NMR (DMSO-d6) δ in ppm: 10.21 (s, 1H, tetrazole), 8.39 (d, 1H, J=8.58 Hz, aryl H), 7.73 (d, 3H, J=9.92 Hz, aryl H), 6.64-6.54 (m, 2H, aryl H), 6.34 (s, 2H, —NH$_2$), 5.18 (s, 2H, —CH$_2$—O)

$^{13}$C-NMR (DMSO) δ in ppm: 184.72 ($C^{11}$), 161.51 ($C^{4a}$), 154.61 ($C^8$), 142.78 ($C^{6a}$), 139.50 ($C^3$), 137.80 (tetrazole), 134.41 ($C^{10}$), 133.14 ($C^1$), 127.30 ($C^2$), 126.05 ($C^{10a}$), 114.65 ($C^{11a}$), 113.78 ($C^9$), 112.69 ($C^7$), 111.90 ($C^4$), 74.99 ($C^6$)

IR (ATR) (cm$^{-1}$): 1608, 1588, 1553, 1501, 1374, 1300, 1196, 1002, 842, 762, 700

EXAMPLE 95

3-(2,4-Difluorophenylamino)-8-tetrazol-1-yl-6H-dibenzo[b,e]oxepin-11-one (13)

0.015 g (0.042 mmol) of (8) and 0.01 g (0.15 mmol) of sodium azide are suspended in 0.05 g (0.33 mmol) of trimethyl orthoformate at 0° C. 0.03 g (0.50 mmol) of glacial acetic acid is then added to the mixture and the mixture is heated to 100° C. and refluxed for 4 h. After cooling to room temperature, the mixture is concentrated in vacuo and the residue is taken up with EtOAc and dissolved under the influence of heat. The yellow product precipitates out in the cold.

Yield: 0.26 g (88.1%); melting point: 59.0° C.

$C_{21}H_{13}F_2N_5O_2$ (M$_r$=405.37); LC 8.15 min $^1$H-NMR (DMSO-$_{d6}$) δ in ppm: 10.21 (s, 1H, tetrazole), 9.02 (s, 1H, —NH), 8.18 (s, 1H, aryl H), 8.10-7.98 (m, 3H, aryl H), 7.48-7.39 (m, 2H, aryl H), 7.38-7.32 (m, 1H, aryl H), 6.65 (d, 1H, J=9.84 Hz, aryl H), 6.26 (s, 1H, aryl H), 5.34 (s, 2H, —CH$_2$—O)

$^{13}$C-NMR (DMSO-$_{d6}$) δ in ppm: 174.70 ($C^{11}$), 163.21 ($C^{4a}$), not detected (C4'), 155.34 ($C^{2'}$, J=267.55 Hz), 142.79 ($C^3$), 140.74 (tetrazole), 138.38 ($C^{6a}$), 136.36 ($C^1$), 133.85 ($C^8$), 131.53 ($C^{10+10a}$), not detected ($C^9$), 121.42 ($C^{6'}$), 120.00 ($C^{1'}$), 116.75 ($C^{5'}$), 110.28 ($C^2$), 102.02 ($C^4$), 72.60 ($C^6$)

IR (ATR) (cm$^{-1}$): 2790, 2565, 1644, 1608, 1531, 1297, 1250, 1150, 1085, 907, 819, 708 MS (ESI) 404.1 [M–H]$^-$

EXAMPLE 96

2-(2-Methyl-4-Fluoroanilino)-7-methoxydibenzosuberone (10m)

For the preparation of compound 10m, 0.5 g (1.8 mmol) of 2-chloro-7-methoxydibenzosuberone, 0.25 g (2.0 mmol) of 3-methyl-4-fluoroaniline, 0.05 g (0.22 mmol) of Pd(OAc)$_2$, 0.10 g (0.21 mmol) of 2-(dicyclohexylphosphino)-2',4',6'- triisopropyl-biphenyl, 0.70 g (6.2 mmol) of KOt-Bu, 5 ml of toluene and 1 ml of t-BuOH are used and are reacted by method C.

H$_1$-NMR (DMSO-d6) δ in ppm: 2.96 (s, 4H, —CH$_2$—CH$_2$—), 3.76 (s, 3H, —OCH$_3$), 6.46 (s, 1H, C$^1$—H), 6.61 (d, 1H, J=8.8, C$^3$—H), 6.99-7.26 (m, 5H, C$^8$—H, C$^9$—H, C$^{2'}$—H, C$^{4'}$—H, C$^5$—H), 7.38 (s, 1H, C$^6$—H), 7.94 (s, d, 1H, J=8.7, C$^4$—H), 8.22 (s, 1H, —NH—).

$^{13}$C-NMR (DMSO-d6) δ in ppm: 33.5 (C$^{12}$), 36.4 (C$^{11}$), 55.5 (—OCH$_3$), 111.9 (C$^6$), 113.1 (C$^3$), 113.7 (d, 1C, J=22.2, C$^{5'}$), 114.7 (C$^1$), 117.7 (d, 1C, J=22.0, C$^{3'}$), 118.4 (C$^3$), 126.7 (C$^8$), 127.0 (C$^{1'}$), 130.4 (C$^9$), 134.0 (C$^{5a}$), 134.5 (C$^4$), 135.4 (d, 1C, J=2.6, C$^{2'}$), 136.2 (d, 1C, J=8.3, C$^{1'}$—H), 140.2 (C$^{9a}$), 145.9 (C$^{11a}$), 150.9 (C$^2$), 158.0 (C$^7$), 159.6 (d, 1C, J=241.0, C$^{4'}$), 190.5 (C$^5$).

EXAMPLE 97

2-(2-Chloroanilino)-7-methoxydibenzosuberone (10n)

For the preparation of compound 10n, 0.5 g (1.8 mmol) of 2-chloro-7-methoxydibenzosuberone, 0.27 g (2.1 mmol) of 2-chloroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g (6.2 mmol) of KOt-Bu, 5 ml of toluene and 1 ml of t-BuOH are used and are reacted by method C.

H$_1$-NMR (DMSO-d6) δ in ppm: 3.00 (s, 4H, —CH$_2$—CH$_2$—), 3.77 (s, 3H, —OCH$_3$), 6.73 (s, 1H, C$^1$—H), 6.84 (d, 1H, C$^3$—H), 7.02-7.54 (m, 7H, C$^6$—H, C$^7$—H, C$^8$—H, C$^{2'}$—H, C$^{3'}$—H, C$^{4'}$—H, C$^{5'}$), 7.95 (d, 1H, J=8.7, C$^4$—H), 8.45 (s, 1H, —NH—).

$^{13}$C-NMR (DMSO-d6) δ in ppm: 33.5 (C$^{12}$), 36.2 (C$^{11}$), 55.5 (—OCH$_3$), 113.4 (C$^6$), 114.6 (C$^3$), 114.9 (C$^1$), 118.6 (C$^8$), 124.5 (C$^{4'}$), 125.4 (C$^{6'}$), 127.3 (C$^{5'}$), 128.1 (C$^{4a}$), 128.4 (C$^{2'}$), 130.6 (C$^9$), 130.7 (C$^{3'}$), 133.7 (C$^4$), 134.5 (C$^{5a}$), 138.1 (C$^{1'}$), 140.0 (C$^{9a}$), 145.6 (C$^{11a}$), 148.9 (C$^2$), 158.1 (C$^7$), 190.9 (C$^5$).

EXAMPLE 98

2-(2,4-Difluoroanilino)-7-hydroxy-10,11-dihydrodibenzo[a,d]-cyclohepten-5-one (11a)

0.2 g (0.55 mmol) of 2-(2,4-difluoroanilino)-7-methoxy-10,11-dihydrodibenzo[a,d]-cyclohepten-5-one is dissolved in 2 ml of glacial acetic acid, 2 ml of HBr (45%) are added and the mixture is refluxed for 6 h. The solution is hydrolyzed with 200 g of ice and the precipitate is filtered off. The product is obtained in the form of a white powder. $C_{21}H_{15}F_2NO_2$ (Mr=351.35)

EXAMPLE 99

2-(2-Amino-4-fluoroanilino)-7-hydroxy-10,11-dihydrodibenzo[a,d]-cyclohepten-5-one (11b)

0.2 g (0.55 mmol) of 2-(2-amino-4-fluoroanilino)-7-methoxy-10,11-dihydrodibenzo[a,d]-cyclohepten-5-one is dissolved in 2 ml of glacial acetic acid, 2 ml of HBr (45%) are added and the mixture is refluxed for 6 h. The solution is hydrolyzed with 200 g of ice and the precipitate is filtered off. The product is obtained in the form of a white powder. $C_{21}H_{17}FN_2O_2$ (Mr=348.38)

EXAMPLE 100

2-(2-Chloro-4-fluoroanilino)-7-hydroxy-10,11-dihydrodibenzo[a,d]-cyclohepten-5-one (11c)

$C_{21}H_{15}ClFNO_2$ (Mr=367.81)

0.2 g (0.52 mmol) of 2-(2-chloro-4-fluoroanilino)-7-methoxy-10,11-dihydrodibenzo[a,d]-cyclohepten-5-one is dissolved in 2 ml of glacial acetic acid, 2 ml of HBr (45%) are added and the mixture is refluxed for 6 h. The solution is hydrolyzed with 200 g of ice and the precipitate is filtered off. The product is obtained in the form of a white powder.

EXAMPLE 101

2-(2-Chloroanilino)-7-hydroxy-10,11-dihydrodibenzo[a,d]-cyclohepten-5-one (11d)

0.2 g (0.55 mmol) of 2-(2-chloroanilino)-7-methoxy-10,11-dihydrodibenzo[a,d]-cyclohepten-5-one is dissolved in 2 ml of glacial acetic acid, 2 ml of HBr (45%) are added and the mixture is refluxed for 6 h. The solution is hydrolyzed with 200 g of ice and the precipitate is filtered off. The product is obtained in the form of a white powder.

EXAMPLE 102

2-(Anilino)-7-hydroxy-10,11-dihydrodibenzo[a,d]-cyclohepten-5-one (11e)

0.2 g (0.61 mmol) of 2-anilino-7-methoxy-10,11-dihydrodibenzo[a,d]-cyclohepten-5-one is dissolved in 2 ml of glacial acetic acid, 2 ml of HBr (45%) are added and the mixture is refluxed for 6 h. The solution is hydrolyzed with 200 g of ice and the precipitate is filtered off. The product is obtained in the form of a white powder. $C_{21}H_{17}NO_2$ (Mr=315.380)

EXAMPLE 103

2-(2,4-Difluoroanilino)-7-hydroxy-dibenzo[a,d]-cyclohepten-5-one 0.2 g (0.55 mmol) of 2-(2-amino-4-fluoroanilino)-7-methoxy-10,11-dihydrodibenzo[a,d]-cyclohepten-5-one is dissolved in 2 ml of glacial acetic acid, 2 ml of HBr (45%) are added and the mixture is refluxed for 6 h. The solution is hydrolyzed with 200 g of ice and the precipitate is filtered off. The product is obtained in the form of a white powder.

EXAMPLE 104

2-(2,4-Difluoroanilino)-7-[3-(4-hydroxypiperidin-4-yl-propoxy)]-10,11-dihydrodibenzo[a,d]-cyclohepten-5-one (14n)

For the preparation of compound 14, 0.72 g (1.8 mmol) of 2-chloro-7-[3-(4-hydroxypiperidin-4-yl-propoxy)]-10,11-dihydrodibenzo[a,d]-cyclohepten-5-one, 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g (6.2 mmol) of KOt-Bu, 5 ml of toluene and 1 ml of t-BuOH are used.

EXAMPLE 105

3-(2-Amino-4-fluorophenylamino)-8-amino-6H-dibenzo[b,e]oxepin-11-one (58)

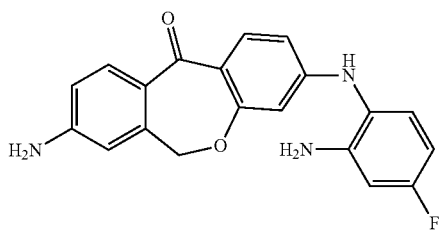 [SMILES: Nc1ccc2c(c1)COc1cc(Nc3ccc(F)cc3N)ccc1C2=O]

0.60 g (2.66 mmol) of tin(II) chloride dihydrate is dissolved in 10 ml of EtOH, 0.10 g (0.89 mmol) of the 8-nitro compound is added and the reaction is carried out by method D.

Yield: 0.01 g (11.9%); melting point: 194.5° C.; $C_{20}H_{16}FN_3O_2$ ($M_r$=349.37); LC 7.34 min $^1$H-NMR (MeOH-$d_4$) δ in ppm: 8.08 (d, 1H, J=8.97 Hz, aryl H), 7.77 (d, 1H, J=8.96 Hz, aryl H), 7.07-6.96 (m, 1H, aryl H), 6.69-6.38 (m, 5H, aryl H), 6.07 (s, 1H, aryl H), 4.97 (s, 2H, —CH$_2$—O)

$^{13}$C-NMR (MeOH-$d_4$) δ in ppm: 186.68 ($C^{11}$), 163.57 ($C^{4'}$, J=217.20 Hz), 155.84 ($C^{4'}$, J=217.20 Hz), 153.68 ($C^8$), 149.21 ($C^3$), 139.15 ($C^{6a}$), 133.41 ($C^1$), 131.81 ($C^{10}$), 130.23 ($C^{1'}$), 128.66 ($C^{6'}$, J=11.6 Hz), 116.88 ($C^{11a}$), 115.34 ($C^9$), 113.61 ($C^7$), 109.27 ($C^2$), 105.34 ($C^{5'}$, J=24.45 Hz), 103.03 ($C^{3'}$, J=23.18 Hz), 101.15 ($C^4$), 73.67 ($C^6$)

IR (ATR) (cm$^{-1}$): 1602, 1579, 1551, 1505, 1293, 1265, 1233, 1161, 1113, 831, 759

MS (ESI) 350.3 [M+H]$^+$

EXAMPLE 106

Morpholine-4-carboxylic acid [3-(2,4-difluorophenylamino)-1-oxo-6,11-dihydrodibenzo[b,e]oxepin-8-yl]amide

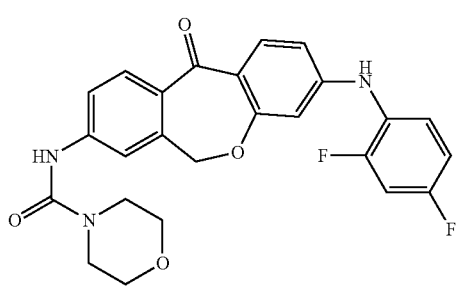 [SMILES: O=C1c2ccc(NC(=O)N3CCOCC3)cc2COc2cc(Nc3ccc(F)cc3F)ccc21]

0.025 g (0.16 mmol) of morpholine-4-carboxylic acid chloride is slowly added dropwise to a solution of 0.05 g (0.14 mmol) of 3-(2,4-difluorophenylamino)-8-amino-6H-dibenzo[b,e]oxepin-11-one and 0.03 g (0.30 mmol) of triethylamine (freshly distilled) in 3 ml of tetrahydrofuran, while cooling with ice. When the addition has ended, the mixture is stirred at RT under an argon atmosphere for 2 h. At the end of the reaction, excess solvent is evaporated off on a rotary evaporator, the residue is taken up in EtOAc and the mixture is extracted by shaking against 5% strength NaHCO$_3$ solution. The organic phase is evaporated on a rotary evaporator, the crude product is recrystallized in MeOH/H$_2$O and the product is then washed with diethyl ether and dried.

Yield: 0.03 g (46.0%); melting point: 244.3° C.; $C_{25}H_{21}F_2N_3O_4$ ($M_r$=465.46); LC 7.76 min $^1$H-NMR (DMSO-$d_6$) δ in ppm: 7.99 (d, 1H, J=8.69 Hz, aryl H), 7.70 (d, 1H, J=2.83 Hz, aryl H), 7.39-7.34 (m, 2H, aryl H), 7.12-7.08 (m, 1H, aryl H), 6.70-6.57 (m, 3H, aryl H), 6.24 (s, 1H, aryl H), 5.05 (s, 2H, —CH$_2$—O)

IR (ATR) (cm$^{-1}$): 1556, 1512, 1309, 1229, 1097, 911, 872, 833, 694

MS (ESI) 464.1 [M–H]$^-$

Compounds position 8

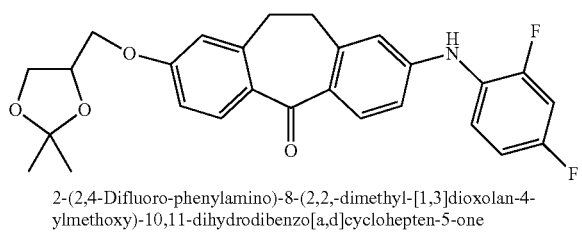

2-(2,4-Difluoro-phenylamino)-8-(2,2,-dimethyl-[1,3]dioxolan-4-ylmethoxy)-10,11-dihydrodibenzo[a,d]cyclohepten-5-one

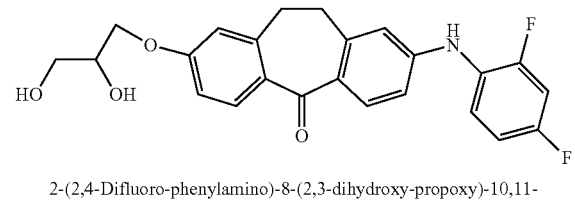

2-(2,4-Difluoro-phenylamino)-8-(2,3-dihydroxy-propoxy)-10,11-dihydrodibenzo[a,d]cyclohepten-5-one

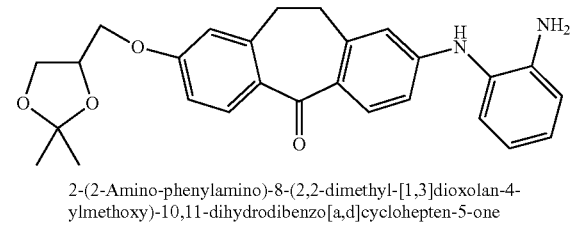

2-(2-Amino-phenylamino)-8-(2,2-dimethyl-[1,3]dioxolan-4-ylmethoxy)-10,11-dihydrodibenzo[a,d]cyclohepten-5-one

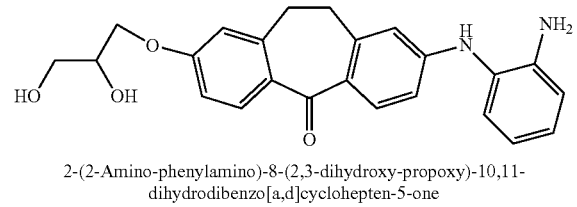

2-(2-Amino-phenylamino)-8-(2,3-dihydroxy-propoxy)-10,11-dihydrodibenzo[a,d]cyclohepten-5-one

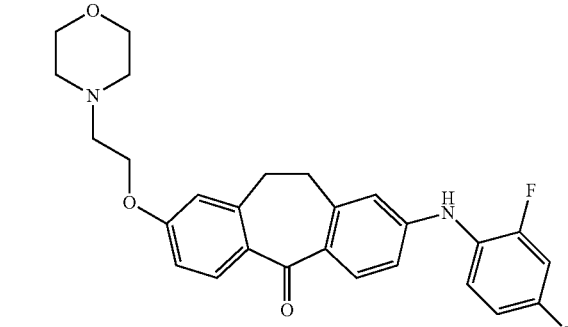

2-(2,4-Difluorophenylamino)-8-(2-morpholin-4-yl-ethoxy)-10,11-dihydrodibenzo[a,d]cyclohepten-5-one Compounds position 9

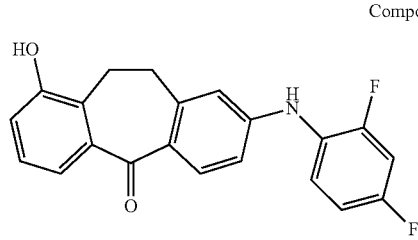

8-(2,4-Difluorophenylamino)-1-hydroxy-10,11-dihydrodibenzo[a,d]cyclohepten-5-one

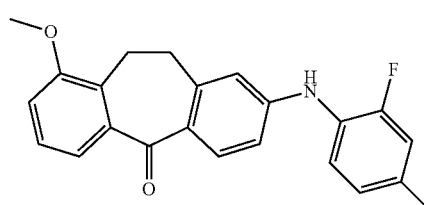

8-(2,4-Difluorophenylamino)-1-methoxy-10,11-dihydrodibenzo[a,d]cyclohepten-5-one

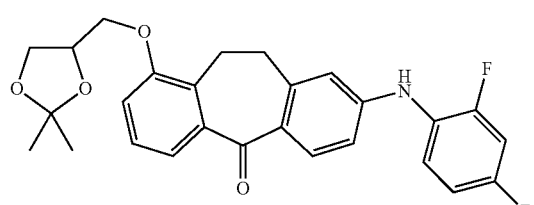

(S)-8-(2,4-Difluorophenylamino)-1-(2,2-dimethyl-[1,3]dioxolan-4-ylmethoxy)-10,11-dihydrodibenzo[a,d]cyclohepten-5-one

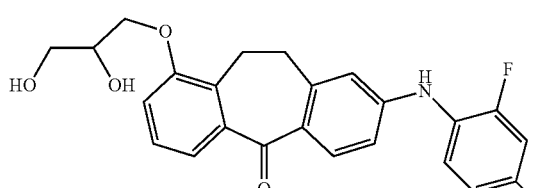

(R)-8-(2,4-Difluorophenylamino)-1-(2,3-dihydroxy-propoxy)-10,11-dihydrodibenzo[a,d]cyclohepten-5-one

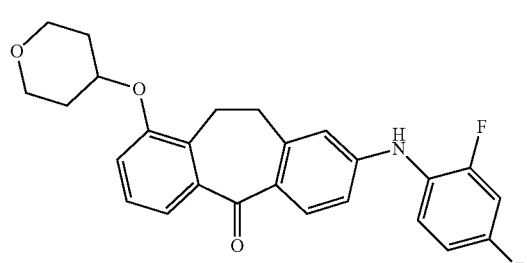

8-(2,4-Difluorophenylamino)-1-tetrahydro-pyran-4-yloxy)-10,11-dihydrodibenzo[a,d]cyclohepten-5-one

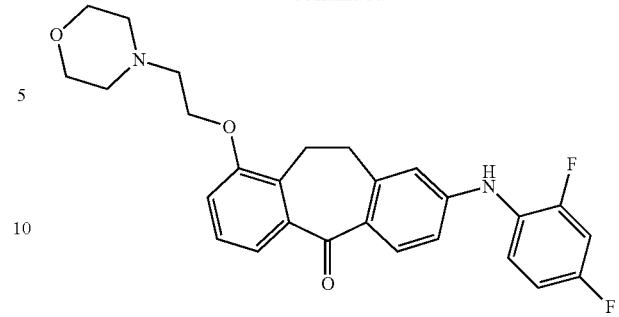

8-(2,4-Difluorophenylamino)-1-(2-morpholin-4-yl-ethoxy)-10,11-dihydrodibenzo[a,d]cyclohepten-5-one

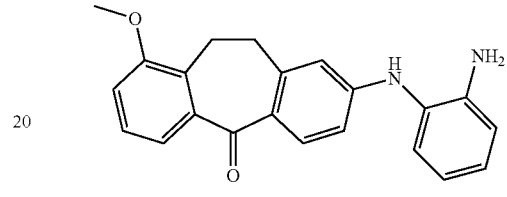

8-(2-Aminophenylamino)-1-methoxy-10,11-dihydrodibenzo[a,d]cyclohepten-5-one

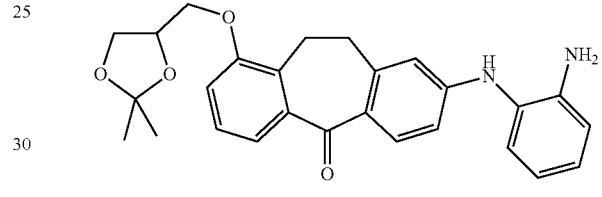

(S)-8-(2-Aminophenylamino)-1-(2,2-dimethyl-[1,3]dioxolan-4-ylmethoxy)-10,11-dihydrodibenzo[a,d]cyclohepten-5-one

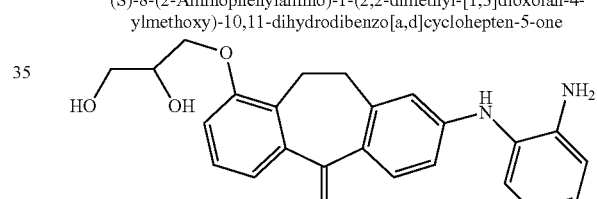

(R)-8-(2-Aminophenylamino)-1-(2,3-dihydroxy-propoxy)-10,11-dihydrodibenzo[a,d]cyclohepten-5-one General Method AA For the preparation of the test compounds, a mixture of aryl halide, aniline derivative, Pd(OAc)$_2$, phosphine ligand, Na—O-tert-butylate or K—O-tert-butylate, toluene and tert-BuOH is heated to 100° C. under an argon inert gas atmosphere and stirred at this temperature for the stated time. Thereafter, the mixture is cooled to room temperature, hydrolysis is carried out with 150 ml of H$_2$O, the mixture is extracted 3× with 200 ml of diethyl ether each time and the organic phase is filtered and concentrated in vacuo. Purification is carried out via flash chromatography.

General Method AB

For hydrolysis of the acetal in MeOH, the stated amount of H$_2$O and p-toluenesulfonic acid is added. The solution is heated to 50° C. under an argon inert gas atmosphere. After 6 h, the solution is cooled to room temperature and concentrated in vacuo. A yellow oil is obtained, which is dissolved again in ethyl acetate and 5% strength Na$_2$HCO$_3$ solution (50 ml). The organic phase is separated off and concentrated in vacuo. The diol precipitates out in the form of a white solid, which is recrystallized from methylene chloride/hexane.

General Method AC

For the preparation of the secondary amine, the stated amounts of the amino component are dissolved in a toluene/tert-butanol mixture in a dry 100 ml three-necked flask with a reflux condenser and bubble counter under an argon atmosphere, with heating. The stated amounts of the phosphine ligand (2-(dicyclohexylphosphino)-2',4',6'-triisopropylbiphenyl, K—O-tert-butylate, halogen component and Pd(OAc)$_2$ are now added and the mixture is refluxed at 110° C. under an argon atmosphere for 2-6 h under TLC monitoring. When the reaction has ended, the mixture is cooled to RT and filtered. The residue on the filter is washed several times with methylene chloride, methanol and ethyl acetate and the combined organic phases are concentrated in vacuo. The brown product mixture which thereby remains is purified by chromatography with hexane:ethyl acetate (3:1) over silica gel.

EXAMPLE 107

2-(2,4-Difluorophenylamino)-7-(3-morpholin-4-yl-propoxy)-10,11-dihydrodibenzo[a,d]-cyclohepten-5-one (55k)

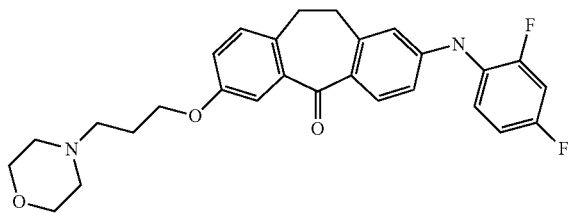 [SMILES: O=C1c2ccc(Nc3ccc(F)cc3F)cc2CCc2ccc(OCCCN3CCOCC3)cc21]

In accordance with general method AA, 0.67 g (1.8 mmol) of 2-chloro-7-(3-morpholin-4-yl-propoxy-10,11-dihydrodibenzo[a,d]-cyclohepten-5-one (36i), 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2',4',6'-triisopropyl-biphenyl, 0.60 g (6.2 mmol) of Na—O-tert-butylate, 5 ml of toluene and 1 ml of tert-BuOH are used. Reaction time: 1 h. Purification is carried out via flash chromatography (SiO$_2$, hexane/ethyl acetate 7+3). $C_{28}H_{28}F_2N_2O_3$ (Mr=478.54); yield 43%; m.p. 114° C.

IR (ATR)* 3313 (N—H), 2852, 1567, 1527, 1496, 1270, 1196, 1146, 1116, 1093, 961, 863, 816 cm$^{-1}$ $^1$H-NMR (DMSO-d6) δ in ppm: 1.79-1.92 (m, 2H, C2propoxy-H), 2.34-2.43 (m, 6H, C3/5-morpholinyl-H, C3propoxy-H), 2.99 (s, 4H, —CH2-CH2-), 3.55 (t, 4H, J=3.6 Hz, C2/6-morpholinyl-H), 4.01 (t, 2H, J=5.8 Hz, C1propoxy-H); 6.60 (s, 1H, C1-H), 6.73 (d, 1H, J=8.7 Hz, C3-H), 7.00-7.38 (m, 6H, C6-H, C8-H, C9-H, C3'-H, C5'-H, C6'-H), 7.94 (d, 1H, J=8.6 Hz, C4-H), 8.53 (s, 1H, —NH—)

$^{13}$C-NMR (DMSO-d6) δ in ppm: 26.2 (C2propoxy), 33.5 (C10), 36.2 (C11), 53.7 (2C, C3/5-morpholinyl), 55.1 (C3propoxy), 65.3 (C1propoxy), 66.5 (2C, C2/6-morpholinyl), 105.3 (dd, 1C, J1=24.1 Hz, J2=26.8 Hz, C3'), 112.2 (dd, 1C, J1=3.8 Hz, J2=22.4 Hz, C5'), 112.6 (C6), 113.8 (C3), 115.2 (C1), 119.2 (C8), 125.2 (dd, 1C, J1=4.2 Hz, J2=11.9 Hz, C1'), 126.4 (dd, 1C, J1=3.4 Hz, J2=9.8 Hz, C6'), 127.7 (C4a), 130.6 (C9), 133.8 (C5a), 134.5 (C4), 140.0 (C9a), 145.7 (C11a), 149.4 (C2), 156.0 (dd, 1C, J1=12.7 Hz, J2=248.3 Hz, C4'), 158.3 (C7), 158.8 (dd, 1C, J1=12.2 Hz, J2=242.2 Hz, C2'), 190.8 (C5)

EXAMPLE 108

2-(2,4-Difluorophenylamino)-8-(3-hydroxypropoxy)-10,11-dihydrodibenzo[a,d]-cyclohepten-5-one (12j)

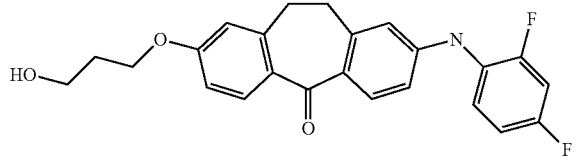 [SMILES: O=C1c2ccc(Nc3ccc(F)cc3F)cc2CCc2cc(OCCCO)ccc21]

In accordance with general method O, 0.65 g (1.8 mmol) of acetic acid 3-(8-chloro-5-oxo-10,11-dihydro-5H-dibenzo[a,d]cyclohepten-2-yloxy)-propyl ester, 0.25 g (1.9 mmol) of 2,4-difluoroaniline, 0.04 g of Pd(OAc)$_2$, 0.17 g of phosphine ligand and 0.74 g (7.7 mmol) of Na—O-tert-butylate are reacted in 10 ml of toluene and 2 ml of tert-BuOH. Yield: 42%; m.p.: 154° C.

$C_{24}H_{21}F_2NO_3$ (Mr=409.44); HPLC 8.7 min; 98.3%

IR (ATR) (cm$^{-1}$): 3359, 2918, 1605, 1581, 1529, 1270, 1240, 1118, 1098, 1055, 960, 843, 772, 692, 455.

$^1$H-NMR (DMSO-d6) δ in ppm: 1.86 (q, 2H, J=6.28 Hz, C2-H hydroxy-propoxy), 3.01 (dd, 4H, J1=12.45 Hz, J2=9.23 Hz, —CH2-CH2-), 3.55 (dd, 2H, J1=11.44 Hz, J2=5.97 Hz, C3-H hydroxypropoxy), 4.11 (t, 2H, J=6.30 Hz, C1-H hydroxypropoxy), 4.56 (t, 1H, J=5.11 Hz, —OH), 6.61 (s, 1H, C1-H), 6.73 (d, 1H, J=8.90 Hz, C3-H), 6.84-6.91 (m, 2H, C3'—/C6'-H), 7.03-7.14 (m, 1H, C5'-H), 7.29-7.42 (m, 2H, C7-/C9-H), 7.96 (d, 2H, J=8.71 Hz, C4-/C6-H), 8.49 (s, 1H, —NH—).

$^{13}$C-NMR (DMSO-d6) δ in ppm: 32.4 (C2 hydroxypropoxy), 35.2 (C11), 35.8 (C10), 57.5 (C3 hydroxypropoxy), 65.2 (C1 hydroxypropoxy), 105.3 (dd, J1=26.6 Hz, J2=23.9 Hz, C3'), 112.1 (dd, J1=26.6 Hz, J2=23.9 Hz, C5'), 112.5 (C7), 113.0 (C9), 113.6 (C3), 114.4 (C1), 125.4 (dd, J1=12.0 Hz, J2=3.6 Hz, C1'), 126.2 (dd, J1=9.6 Hz, J2=3.3 Hz, C6'), 128.3 (C4a), 131.2 (C5a), 133.7 (C6), 133.8 (C4), 145.2 (C9a), 145.3 (C2), 149.1 (C11a), 155.9 (dd, J1=246.3 Hz, J2=12.4 Hz, C4'), 158.6 (dd, J1=234.8 Hz, J2=11.8 Hz, C2'), 161.9 (C8), 189.1 (C5).

EXAMPLE 109

2-(2,4-Difluorophenylamino)-8-(2-hydroxyethoxy)-10,11-dihydrodibenzo[a,d]-cyclohepten-5-one (12k)

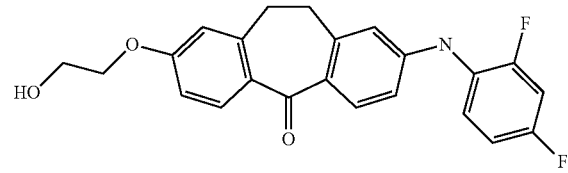 [SMILES: O=C1c2ccc(Nc3ccc(F)cc3F)cc2CCc2cc(OCCO)ccc21]

In accordance with general method O, 0.67 g (0.19 mmol) of acetic acid 2-(8-chloro-5-oxo-10,11-dihydro-5H-dibenzo[a,d]cyclohepten-2-yloxy)-ethyl ester, 0.26 g (0.0020 mol) of 2,4-difluoroaniline, 0.04 g of Pd(OAc)$_2$, 0.14 g of phosphine ligand and 0.70 g (7.3 mmol) of Na—O-tert-butylate are reacted in 10 ml of toluene and 2 ml of tert-BuOH. Yield: 20%; m.p.: 138° C.

$C_{23}H_{19}F_2NO_3$ (Mr=395.41); HPLC 8.1 min; 98.1%

IR (ATR) (cm$^{-1}$): 3406, 3283, 2919, 1596, 1535, 1495, 1343, 1297, 1265, 1239, 1210, 1186, 1108, 1093, 1077, 1042, 959, 857, 847, 781, 655, 497, 455.

$^1$H-NMR (DMSO-d6) δ in ppm: 2.97-3.07 (m, 4H, —CH2-CH2-), 3.68-3.76 (m, 2H, C2-H hydroxyethoxy), 4.06 (t, 2H, J=4.78 Hz, C1-H hydroxyethoxy), 4.89 (t, 1H, J=5.48 Hz, —OH), 6.61 (s, 1H, C1-H), 6.73 (d, 1H, J=8.53 Hz, C3), 6.85-6.92 (m, 2H, C3'-/C6'-H), 7.05-7.13 (m, 1H, C5'-H), 7.29-7.43 (m, 2H, J=8.71 Hz, C4-/C6-H), 8.47 (s, 1H, —NH—).

EXAMPLE 110

2-(2,4-Difluorophenylamino)-8-methoxy-10,11-dihydrodibenzo[a,d]cyclo-hepten-5-one (12a)

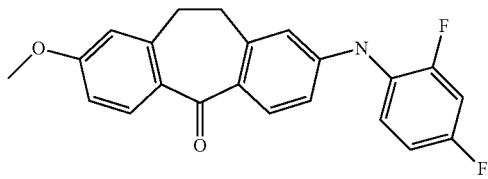 [SMILES: COc1ccc2c(c1)CCc1cc(Nc3ccc(F)cc3F)ccc1C2=O]

In accordance with general method O, 0.52 g (1.9 mmol) of 2-chloro-8-methoxy-10,11-dihydrodibenzo[a,d]cyclohepten-5-one, 0.30 g (2.3 mmol) of 2,4-difluoroaniline, 0.04 g of Pd(OAc)$_2$, 0.16 g of phosphine ligand and 0.86 g (8.9 mmol) of Na—O-tert-butylate are reacted in 10 ml of toluene and 2 ml of tert-BuOH. Purification is carried out by column chromatography (flash; SiO$_2$; hexane 90%/ethyl acetate 10%). Yield: 66%; m.p.: 157° C.

$C_{22}H_{17}F_2NO_2$ (Mr=365.38); HPLC 9.4 min, 99.9%; GC 34.6 min

MS m/z (%): 365 (100, M+), 350 (3, M+-CH3), 337 (5, M+-CO), 322 (14, 337-CH3), 208 (10, 350-O, -difluoroaniline), 194 (3, 322-O, -difluorobenzene), 178 (3, 322-OH, -difluoroaniline), 165 (14, 4-methoxy-2-methylbenzoic acid), 152 (4, 165-CH2).

IR (ATR) (cm$^{-1}$): 3302, 2913, 1581, 1494, 1261, 1238, 1138, 1093, 1033, 965, 954, 862, 846, 777, 729, 695, 563, 511, 444.

$^1$H-NMR (DMSO-d6) δ in ppm: 3.02 (dd, 4H, J1=13.73 Hz, J2=8.96 Hz, —CH2-CH2-), 3.82 (s, 3H, —OCH3), 6.61 (s, 1H, C1-H), 6.73 (d, 1H, J=8.64 Hz, C3-H), 6.84-6.92 (m, 2H, C3'-C6'-H), 7.04-7.13 (m, 1H, C5'-H), 7.34-7.42 (m, 2H, C7-/C9-H), 7.96 (d, 2H, J=8.64 Hz, C4-/C6-H), 8.49 (s, 1H, —NH—).

$^{13}$C-NMR (DMSO-d6) δ in ppm: 35.2 (C11), 35.8 (C10), 55.7 (—OCH3), 105.3 (dd, J1=26.5 Hz, J2=24.0 Hz, C3'), 112.1 (dd, J1=21.5 Hz, J2=3.7 Hz, C5'), 112.5 (C7), 112.7 (C9), 113.6 (C3), 113.9 (C1), 125.4 (dd, J1=12.1 Hz, J2=3.6 Hz, C1'), 126.3 (dd, J1=9.1 Hz, J2=3.3 Hz, C6'), 128.2 (C4a), 131.3 (C5a), 133.7 (C4), 133.8 (C6), 145.1 (C2), 145.3 (C11a), 149.1 (C9a), 155.9 (dd, J1=246.4 Hz, J2=12.5 Hz, C4'), 158.7 (dd, J1=241.6 Hz, J2=11.4 Hz, C2'), 162.4 (C8'), 189.1 (C5).

EXAMPLE 111

2-(2-Aminophenylamino)-8-methoxy-10,11-dihydrodibenzo[a,d]cyclohepten-5-one (12b)

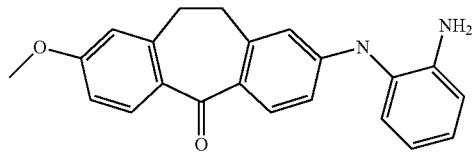 [SMILES: COc1ccc2c(c1)CCc1cc(Nc3ccccc3N)ccc1C2=O]

In accordance with general method O, 0.48 g (1.8 mmol) of 2-chloro-8-methoxy-10,11-dihydrodibenzo[a,d]cyclohepten-5-one, 1.05 g (9.7 mmol) of phenylenediamine, 0.04 g of Pd(OAc)$_2$, 0.20 g of phosphine ligand and 1.65 g (17 mmol) of Na—O-tert-butylate are reacted in 10 ml of toluene and 2 ml of tert-BuOH. Purification is carried out by column chromatography (flash; SiO$_2$; hexane 80%/ethyl acetate 20%). Yield: 35%; m.p.: 200° C.

$C_{22}H_{20}N_2O_2$ (Mr=344.42); HPLC 8.2 min; 99.6%; GC 63.6 min

MS m/z (%): 344 (100, M+), 329 (8, M+-CH3), 315 (5, M+-CO), 301 (9, 315-CH3), 195 (10, 315-O, -aminobenzene), 158 (11), 107 (7, diaminobenzene).

IR (ATR) (cm$^{-1}$): 311, 2921, 2852, 1287, 1262, 1240, 1206, 1153, 1092, 1031, 835, 744, 696, 595, 562, 489, 441.

$^1$H-NMR (DMSO-d6) δ in ppm: 2.98 (dd, 4H, J1=17.6 Hz, J2=8.96 Hz, —CH2-CH2-), 3.81 (s, 3H, —OCH3), 4.84 (s, 2H, —NH2), 6.47 (s, 1H, C1-H), 6.57-6.64 (m, 2H, C3'-/C6'-H), 6.76-6.91 (m, 5H, C3-/C7-/C9-H and C4'-/C5'-H), 7.91-7.98 (m, 3H, —NH— and C4-/C6-H).

$^{13}$C-NMR (DMSO-d6) δ in ppm: 35.2 (C11), 36.1 (C10), 55.7 (—OCH3), 112.0 (C7), 112.6 (C9), 112.8 (C3), 113.8 (C1), 115.8 (C3'), 116.8 (C4'), 125.4 (C4a), 126.1 (C6'), 126.3 (C5'), 126.7 (C5a), 131.6 (C1), 133.7 (C4), 133.9 (C6), 144.0 (C2'), 145.0 (C2), 145.4 (C11a), 150.8 (C9a), 162.2 (C8), 188.7 (C5).

EXAMPLE 112

2-(2,4-Difluoro-phenylamino)-7-[2-((R)-2,2-dimethyl-[1,3]dioxolan-4-yl)-ethoxy]-10,11-dihydrodibenzo[a,d]cyclohepten-5-one (55h)

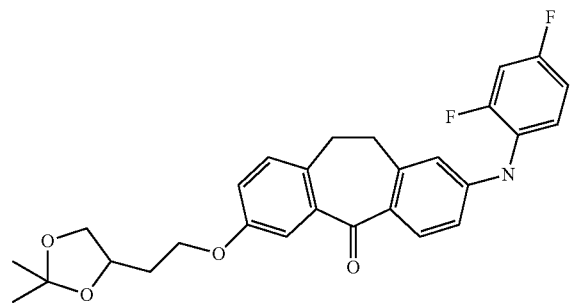 [SMILES: CC1(C)OCC(CCOc2ccc3c(c2)C(=O)c2ccc(Nc4ccc(F)cc4F)cc2CC3)O1]

In accordance with general method AA, 0.70 g (1.8 mmol) of 2-chloro-7-(2((R)-2,2-dimethyl-[1,3]dioxolan-4-yl)-ethoxy]-10,11-dihydrodibenzo[a,d]-cyclohepten-5-one (360, 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2'-, 4'-,6'-triisopropyl-biphenyl, 0.60 g (6.2 mmol) of Na—O-tert-butylate, 5 ml of toluene and 1 ml of tert-BuOH are used. Reaction time: 1 h. Purification is carried out via flash chromatography (SiO$_2$, hexane/ethyl acetate 7+3). Yield: 45%;

m.p.: 123° C.

C$_{28}$H$_{27}$F$_2$NO$_4$ (Mr=479.53)

IR (ATR)* 3307 (N—H), 1607, 1552, 1499, 1355, 1286, 1201, 1142, 1093, 1054, 962, 869, 786 cm$^{-1}$ $^1$H-NMR (DMSO-d6) δ in ppm: 1.25 (s, 3H, —CH3), 1.31 (s, 3H, —CH3), 1.89-1.98 (m, 2H, C2ethoxy-H), 2.99 (s, 4H, —CH2-CH2-), 3.52-3.59 (m, 1H, C5-dioxolanyl-H), 4.00-4.23 (m, 4H, C1ethoxy-H, C4-dioxolonyl-H, C5-dioxolanyl-H), 6.60 (s, 1H, C1-H), 6.73 (d, 1H, J=8.7 Hz, C3-H); 7.00-7.46 (m, 6H, C6-H, C8-H, C9-H, C3'-H, C5'-H, C6'-H), 7.94 (d, 1H, J=8.8 Hz, C4-H), 8.54 (s, 1H, —NH—)

$^{13}$C-NMR (DMSO-d6) δ in ppm: 26.0 (—CH3), 27.2 (—CH3), 33.3 (C2ethoxy), 33.5 (C10), 36.2 (C11), 65.0 (C1ethoxy), 69.0 (C5-dioxolanyl), 73.2 (C4-dioxolanyl), 105.3 (dd, 1C, J1=24.5 Hz, J2=26.7 Hz, C3'), 108.3 (C2-dioxolanyl), 112.2 (dd, 1C, J1=3.8 Hz, J2=22.2 Hz), 112.6 (C6), 113.8 (C3), 115.3 (C1), 119.0 (C8), 125.3 (dd, 1C, J1=3.8 Hz, J2=12.0 Hz, C1'), 126.4 (dd, 1C, J1=3.5 Hz, J2=9.8 Hz, C6'), 127.7 (C4a), 130.6 (C9), 133.8 (C5a), 134.7 (C4), 140.0 (C9a), 145.7 (C11a), 149.5 (C2), 156.0 (dd, 1C, J1=12.3 Hz, J2=248.0 Hz, C4'), 158.6 (C7); 158.8 (dd, 1C, J1=11.5 Hz, J2=242.9 Hz, C2'), 190.8 (C5)

EXAMPLE 113

2-(2,4-Difluorophenylamino)-7-methoxy-10,11-dihydrodibenzo[a,d]-cyclo-hepten-5-one (52b)

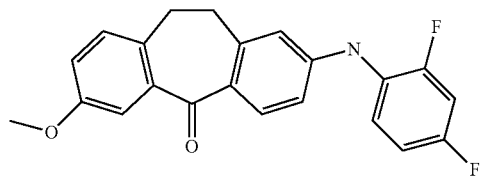 [SMILES: COc1ccc2c(c1)C(=O)c1ccc(Nc3ccc(F)cc3F)cc1CC2]

In accordance with general method AA, 0.50 g (1.8 mmol) of 2-chloro-7-methoxy-10,11-dihydrodibenzo[a,d]-cyclo-hepten-5-one (34), 0.25 g (1.9 mmol) of 2,4-difluoroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.70 g (6.2 mmol) of K—O-tert-butylate, 5 ml of toluene and 1 ml of tert-BuOH are used. Reaction time: 1 h. Purification is carried out via flash chromatography (SiO$_2$, hexane/ethyl acetate 8+2). Yield: 87%; melting point: 123-126° C. (decomposition)

C$_{22}$H$_{17}$F$_2$NO$_2$ (Mr=365.38); GC 31.4 min

MS m/z (%): 365 (100, M+), 350 (7, M$^+$-CH$_3$), 337 (11), 322 (6), 237 (4, M$^+$-2-(NH$_2$—, 4-F-aniline)), 208 (15), 194 (5), 178 (6), 165 (15), 152 (5)

IR (ATR) 3327 (N—H), 3074 (C—H), 2941-2842 (C—H), 1604, 1552, 1525, 1498, 1338, 1325, 1281, 1238, 854, 832, 786 cm$^{-1}$ $^1$H-NMR (DMSO-d6) δ in ppm: 2.99 (s, 4H, —CH2-CH2-), 3.76 (s, 3H, —OCH3), 6.61 (s, 1H, C1-H), 6.74 (d, 1H, J=8.7 Hz, C3-H), 7.00-7.47 (m, 6H, C6-H, C8-H, C9-H, C3'-H, C5'-H, C6'-H), 7.95 (d, 1H, J=8.8 Hz, C4-H), 8.55 (s, 1H, —NH—)

$^{13}$C-NMR (DMSO-d6) δ in ppm: 33.5 (C10), 36.2 (C11), 55.5 (—OCH3), 105.3 (dd, 1C, J1=24.3 Hz, J2=26.7 Hz, C3'), 112.2 (dd, 1C, J1=3.5 Hz, J2=21.8 Hz, C5'), 112.6 (C6), 113.9 (C3), 114.7 (C1), 118.6 (C8), 125.3 (dd, 1C, J1=3.8 Hz, J2=12.3 Hz, C1'), 126.4 (dd, 1C, J1=3.4 Hz, J2=9.6 Hz, C6'), 127.7 (C4a), 130.6 (C9), 133.8 (C5a), 134.6 (C4), 140.0 (C9a), 145.7 (C11a), 149.4 (C2), 156.0 (dd, 1C, J1=12.3 Hz, J2=248.1 Hz, C4'), 158.1 (C7), 158.8 (dd, 1C, J1=11.1 Hz, J2=143.1 Hz, C2'), 190.8 (C5)

EXAMPLE 114

7-Methoxy-2-(2,3,4-trifluorophenylamino)-10,11-dihydrodibenzo[a,d]-cyclo-hepten-5-one (52n)

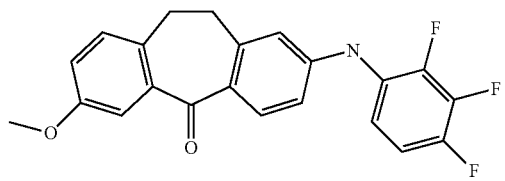 [SMILES: COc1ccc2c(c1)C(=O)c1ccc(Nc3ccc(F)c(F)c3F)cc1CC2]

In accordance with general method AA, 0.50 g (1.8 mmol) of 2-chloro-7-methoxy-10,11-dihydrodibenzo[a,d]-cyclo-hepten-5-one (34), 0.27 g (1.8 mmol) of 2,3,4-trifluoroaniline, 0.05 g (0.22 mmol) of Pd(OAc)$_2$, 0.10 g (0.21 mmol) of 2-(dicyclohexylphosphino)-2'-,4'-,6'-triisopropyl-biphenyl, 0.60 g (6.2 mmol) of Na—O-tert-butylate, 5 ml of toluene and 1 ml of tert-BuOH are used. Reaction time: 1 h. Purification is carried out via flash chromatography (SiO$_2$, hexane/ethyl acetate 8+2). Yield: 72%; melting point: 128° C.

C$_{22}$H$_{16}$F$_3$NO$_2$ (Mr=383.37); GC 32.0 min

MS m/z (%): 383 (100, M$^+$), 368 (7, M$^+$-CH$_3$), 355 (10), 340 (5), 237 (3), 208 (11), 194 (5), 178 (6), 165 (11)

IR (ATR)* 2930, 1578, 1492, 1355, 1265, 1035, 1000, 970, 839, 814 cm$^{-1}$ $^1$H-NMR (DMSO-d6) δ in ppm: 3.03 (s, 4H, —CH2-CH2-), 3.77 (s, 3H, —OCH$_3$), 6.95-7.47 (m, 7H, C1-H, C3-H, C6-H, C8-H, C9-H, C5'-H, C6'-H), 7.92 (d, 1H, J=8.6 Hz, C4-H), N—H-signal not visible.

$^{13}$C-NMR (DMSO-d6) δ in ppm: 33.3 (C10), 35.2 (C11), 55.6 (—OCH3), 113.6-114.0 (m, 1C, C1'); 114.3 (C6); 119.2 (C3), 119.8 (C1), 122.0 (C8), 125.0-125.2 (m, 1C, C5'), 129.9-130.2 (m, 1C, C6'); 131.0 (C4a), 132.6 (C9), 132.7-135.2 (C4'), 133.0 (C5a), 134.6 (C4), 139.4 (C9a), 145.1 (C11a), 149.0 (C2), 145.3-147.9 (m, 1C, C3'), 246.8-148.3 (m, 1C, C2'), 158.1 (C7), 192.3 (C5)

EXAMPLE 115

2-(2,4-Difluoro-phenylamino)-7-(R)-3,4-dihydroxybutoxy)-10,11-dihydrodibenzo[a,d]cyclohepten-5-one (55i)

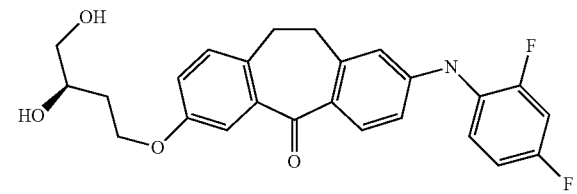 [SMILES: O=C1c2ccc(Nc3ccc(F)cc3F)cc2CCc2ccc(OCC[C@@H](O)CO)cc21]

In accordance with general method AB, 1.00 g (2.1 mmol) of 2-(2,4-difluoro-phenylamino)-7-[2-(R)-2,2-dimethyl-[1, 3]dioxolan-4-yl)ethoxy]-10,11-dihydrodibenzo[a,d]cyclo-hepten-5-one (55h), 40 ml of MeOH, 10 ml of H2O and 0.25 g (1.3 mmol) p-toluenesulfonic acid are used.

Yield: 54%; melting point: 123° C.; $C_{25}H_{23}F_2NO_4$ (Mr=439.46)

IR (ATR) 3310 (N—H), 2928, 1567, 1508, 1261, 1140, 1094, 1055, 964, 845, 808, 780 cm$^{-1}$ $^1$H-NMR (DMSO-d6) δ in ppm: 0.85 (s, 1H, —OH), 1.25 (s, 1H, —OH), 1.52-1.98 (m, 2H, C2butanoxy-H), 2.99 (s, 4H, —CH2-CH2-), 3.55-3.63 (m, 1H, C3butanoxy-H), 4.00-4.08 (m, 2H, C4butanoxy-H), 4.53-4.60 (m, 2H, C1butanoxy-H), 6.59 (s, 1H, C1-H), 6.72 (d, 1H, J=8.6 Hz, 1H, C3-H), 6.94-7.46 (m, 6H, C6-H, C8-H, C9-H, C3'-H, C5'-H, C6'-H), 7.94 (d, 1H, J=8.6 Hz, C4-H), 8.58 (s, 1H, —NH—)

$^{13}$C-NMR (DMSO-d6) δ in ppm: 33.5 (C11), 33.5 (C2butanoxy), 36.2 (C10), 65.1 (C1butanoxy), 66.3 (C4butanoxy), 68.4 (C3butanoxy), 105.3 (dd, 1C, J1=24.5 Hz, J2=27.2 Hz, C3') 112.2 (dd, 1C, J1=3.5 Hz, J2=21.8 Hz, C5'), 112.6 (C6), 113.8 (C3), 115.3 (C1), 119.1 (C8), 125.3 (dd, 1C, J1=3.1 Hz, J2=11.9 Hz, C1'), 126.4 (dd 1C, J1=3.4 Hz, J2=8.6 Hz, C6'), 127.8 (C4a), 130.6 (C9), 133.8 (C5a), 134.5 (C4), 139.9 (C9a), 145.7 (C11a), 149.4 (C2), 156.0 (dd, 1C, J1=19.2 Hz, J2=259.8 Hz, C4'), 157.5 (C7), 158.8 (dd, 1C, J1=16.1 Hz, J2=246.8 Hz, C2'), 190.8 (C5)

EXAMPLE 116

7-Chloro-3-(2,4-difluorophenylamino)-6,11-dihy-drodibenzo[b,e]oxepin-11-one (13)

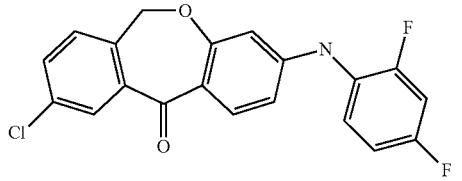 [SMILES: O=C1c2cc(Cl)ccc2COc2cc(Nc3ccc(F)cc3F)ccc21]

In accordance with general method AC, 0.5 g (1.92 mmol) of 3-amino-7-chloro-3,11-dihydrodibenzo[b,e]oxepin-11-one are dissolved in 15 ml of toluene, and 0.08 g of 2-(dicyclohexyl-phosphino)-2',4',6'-triisopropylbiphenyl, 0.37 g of 1-bromo-2,4-difluorobenzene, 0.70 g of K—O-tert-butylate, 2 ml of tert-BuOH and finally 2 spatula tips of Pd(OAc)$_2$ are added. The reaction mixture is now refluxed at 100° C. under an argon atmosphere for 4 h with TLC monitoring. The product mixture is purified by chromatography over silica gel with hexane:EtOAc (3:1).

Yield: 52 mg (7.2%); melting point: 207.9° C.

$C_{20}H_{12}ClF_2NO_2$ (MR=371.8 g/mol); GC (method 1): 21.43 min $^1$H-NMR (DMSO-d6): δ (in ppm)=8.77 (s, 1H, —NH—), 7.93 (d, 1H, J=8.96 Hz, aryl H), 7.74-7.66 (m, 2H, aryl H), 7.54-7.32 (m, 3H, aryl H), 7.10 (t, 1H, J=9.46 Hz, aryl H), 6.62 (d, 1H, J=8.08 Hz, aryl H), 6.24 (s, 1H, aryl H), 5.37 (s, 2H, CH2-O—)

$^{13}$C-NMR (DMSO-d6): δ (in ppm)=187.14 (C11), 163.05 (C4a), 160.14 (q, C2 NH-Ph, J1=148.56 Hz, J2=11.80), 155.26 (q, C4 NH-Ph, J1=152.75 Hz, J2=11.80), 127, 10 (q, C6 NH-Ph, J1=9.52 Hz, J2=3.04 Hz), 124.63 (q, C1 NH-Ph, J1=11.99 Hz, J2=3.23 Hz), 112.27 (q, C5 NH-Ph, J1=22.09 Hz, J2=3.81 Hz), 105.37 (q, C3 NH-Ph, J1=26.28 Hz, J2=24.00 Hz), 152.53 (C3), 143.11 (C6a), 133.54 (C8), 133.11 (C1), 132.81 (C7), 131.84 (C10a), 130.83 (C9), 128.12 (C10), 116.38 (C11a), 110.15 (C2), 101.75 (s, C4), 68.84 (C6)

MS: m/z (%): 371(100), 336(36), 316(6), 243(7), 215(8), 203(7), 152(16), 151(7), 139(8), 89(9), 63 (9)

IR (ATR): ν [cm$^{-1}$]=3306, 1593, 1552, 1512, 1295, 1269, 1141, 1120, 841, 763

The invention claimed is:

1. A compound of the formula I

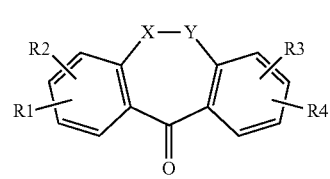

wherein
one of the ring atoms X and Y represents CH$_2$ and the other represents O, S, SO, SO$_2$ or NR5; or —X—Y— represents —CH$_2$—CH$_2$— or —CH═CH—;
R1 is chosen from
A) RO—, wherein R is chosen from:
  a) C$_1$-C$_6$-alkyl, which is substituted by 1, 2 or 3 hydroxyl or C$_1$-C$_6$-alkoxy groups;
  b) C$_1$-C$_6$-alkyl, which is substituted by a saturated or unsaturated, non-aromatic heterocyclic radical having 5 or 6 ring atoms, which contains 1, 2 or 3 hetero atoms which are chosen independently of each other from O, N and S, wherein the heterocyclic radical can optionally contain 1 or 2 hydroxy, C$_1$-C$_6$-alkoxy or C$_1$-C$_6$-alkyl substituents and can be condensed with a phenyl ring or a saturated or unsaturated carbocyclic radical having 5 or 6 ring atoms;
  c) a non-aromatic heterocyclic radical having 5 or 6 ring atoms, which contains 1 or 2 hetero atoms which are chosen independently of each other from O and N;
  d) C$_1$-C$_6$-alkyl;
  e) H;
  f) C$_1$-C$_6$-alkyl, which is substituted by NR6R7;
  g) CF$_3$SO$_2$—;
  h) C$_1$-C$_6$-alkylcarbonyloxy-C$_1$-C$_6$-alkyl; and
  i) (C3-C7-cycloalkyl)-C$_1$-C$_6$-alkyl, which can optionally contain 1 or 2 hydroxy, C$_1$-C$_6$-alkoxy or C$_1$-C$_6$-alkyl substituents on the cycloalkyl radical;
B) NR6R7;
C) tetrazolo; and
D) NR8CONR13R14;
R2 represents H or C$_1$-C$_6$-alkyl;
R3 is chosen from:

a)

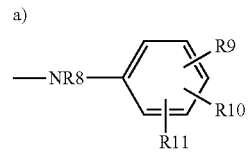

b)

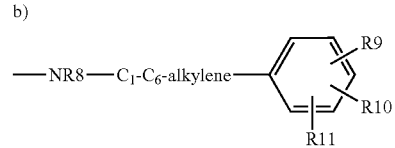

-continued c)
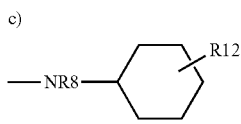

d)
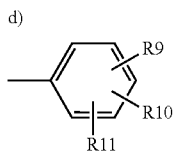

and e) —NH—$C_1$-$C_6$-alkylene-NR6R7

R4 represents H, halogen or $C_1$-$C_6$-alkyl;

R5 represents H or $C_1$-$C_6$-alkyl, which is substituted by 1, 2 or 3 hydroxyl or $C_1$-$C_6$-alkoxy groups;

R6 and R7, which can be identical or different, represent H or $C_1$-$C_6$-alkyl, which is substituted by 1, 2 or 3 hydroxyl or $C_1$-$C_6$-alkoxy groups;

R8 represents H or $C_1$-$C_6$-alkyl;

R9, R10 and R11, which can be identical or different, are chosen from:
a) H,
b) $NH_2$,
c) mono-$C_1$-$C_6$-alkylamino,
d) di-$C_1$-$C_6$-alkylamino,
e) $C_1$-$C_6$-alkyl,
f) $C_1$-$C_6$-alkoxy,
g) hydroxyl,
h) halogen,
i) $C_1$-$C_6$-alkyl, which is substituted by 1, 2 or 3 halogen atoms;
j) CONR6R7; and
k) $NO_2$;

R12 represents H or $NH_2$;

R13 and R14, which can be identical or different, represent H or $C_1$-$C_6$-alkyl, or together with the nitrogen atom to which they are bonded form a non-aromatic heterocyclic radical having 5 or 6 ring atoms, which contains 1 or 2 hetero atoms which are chosen independently of each other from O and N;

and the optical isomers, physiologically acceptable salts and solvates thereof.

2. The compound according to claim 1 of the formula Ia

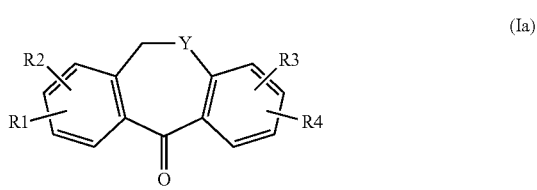
(Ia)

wherein Y represents O and R1, R2, R3 and R4 have the meanings given in claim 1.

3. The compound according to claim 1 of the formula Ib

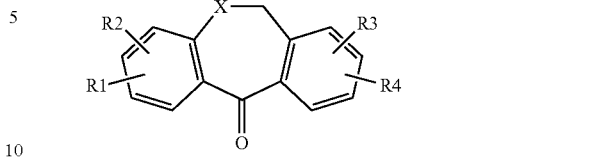
(Ib)

wherein X represents O and R1, R2, R3 and R4 have the meanings given in claim 1.

4. The compound according to claim 1 of the formula Ic

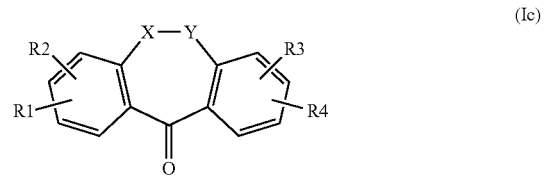
(Ic)

wherein —X—Y— represents —$CH_2$—$CH_2$— or —CH=CH— and R1, R2, R3 and R4 have the meanings given in claim 1.

5. The compound according claim 1, wherein R1 is chosen from $C_1$-$C_6$-alkyl which is substituted by 1, 2 or 3 hydroxyl groups, a saturated non-aromatic heterocyclic radical having 5 or 6 ring atoms, which contains 1 or 2 hetero atoms which are chosen independently of each other from O and N, and which can optionally contain 1 or 2 $C_1$-$C_6$-alkyl substituents, $C_1$-$C_6$-alkoxy, hydroxyl and NR6R7.

6. The compound according to claim 1, wherein R3 is chosen from b) 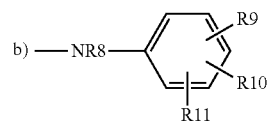

and e) phenyl.

7. The compound according to claim 6, wherein R9 and R10 independently of each other are chosen from H, $NH_2$, mono-$C_1$-$C_6$-alkylamino, di-$C_1$-$C_6$-alkylamino, halogen, $CF_3$, $C_1$-$C_6$-alkyl and $C_1$-$C_6$-alkoxy and R11 represents H or halogen.

8. The compound according to claim 6, wherein R3 represents a radical of the formula

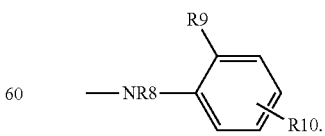

9. The compound according to claim 1, wherein R4 represents H.

10. The compound according to claim 1, wherein R6 and R7 represent H.

11. The compound according to claim 1 of the formula

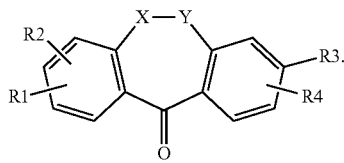

12. The compound according to claim 2 of the formula Iaa

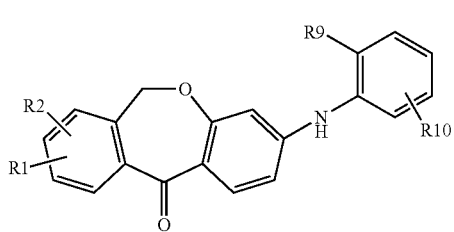

(Iaa)

wherein R1, R2, R9 and R10 have the meanings given in claim 1.

13. The compound according to claim 4 of the formula Ica:

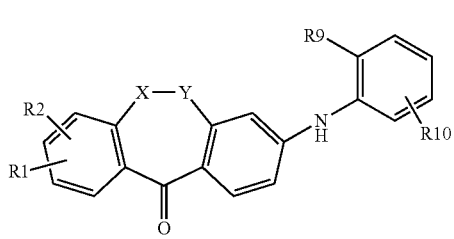

(Ica)

wherein
—X—Y— represents —CH₂—CH₂— or —CH═CH—
and R1, R2, R9 and R10 have the meanings given in claim 1.

14. The compound according to claim 1 selected from the group consisting of:

(1) 2-(2-aminoanilino)-7-methoxydibenzosuberone
(2) 2-(2-amino-4-fluoroanilino)-7-methoxydibenzosuberone
(3) 2-(2,4-difluoroanilino)-7-methoxydibenzosuberone
(4) 2-(2-chloro-4-fluoroanilino)-7-methoxydibenzosuberone
(5) 2-(2,4,5-trifluoroanilino)-7-methoxydibenzosuberone
(6) 2-(2-trifluoromethylanilino)-7-methoxydibenzosuberone
(7) 2-(anilino)-7-methoxydibenzosuberone
(8) 2-(2-methoxyanilino)-7-methoxydibenzosuberone
(9) 2-(3-methyl-4-fluoroanilino)-7-methoxydibenzosuberone
(10) 2-(2-amino-4-trifluoromethylanilino)-7-methoxydibenzosuberone
(11) 2-(phenyl)-7-methoxydibenzosuberone
(12) 2-(2,4-difluoroanilino)-7-methoxydibenzosuberenone
(13) 2-(2,4-difluoroanilino)-7-(S-1,2-isopropylideneglycer-3-yl)-10,11-dihydrodibenzo[a,d]-cyclohepten-5-one
(14) 2-(2,4-difluoroanilino)-7-(R-1,2-isopropylideneglycer-3-yl)-10,11-dihydrodibenzo[a,d]-cyclohepten-5-one
(15) 2-(2-aminoanilino)-7-(S-1,2-isopropylideneglycer-3-yl)-10,11-dihydrodibenzo[a,d]-cyclohepten-5-one
(16) 2-(2-aminoanilino)-7-(R-1,2-isopropylideneglycer-3-yl)-10,11-dihydrodibenzo[a,d]-cyclohepten-5-one
(17) 2-(2,4-difluoroanilino)-7-[2R-,3-dihydroxypropoxy]-10,11-dihydrodibenzo[a,d]-cyclohepten-5-one
(18) 2-(2,4-difluoroanilino)-7-[2S-,3-dihydroxypropoxy]-10,11-dihydrodibenzo[a,d]-cyclohepten-5-one
(19) 2-(2-aminoanilino-7-[2R-,3-dihydroxypropoxy]-10,11-dihydrodibenzo[a,d]-cyclohepten-5-one
(20) 2-(2-aminoanilino-7-[2S-,3-dihydroxypropoxy]-10,11-dihydrodibenzo[a,d]-cyclohepten-5-one
(21) 2-(2,4-difluoroanilino)-7-(2-hydroxy-ethoxy)-10,11-dihydrodibenzo[a,d]-cyclohepten-5-one
(22) 2-(2,4-difluoroanilino)-7-(3-hydroxy-propoxy)-10,11-dihydrodibenzo[a,d]-cyclohepten-5-one
(23) 2-(2,4-difluoroanilino)-7-(2-morpholin-4-yl-ethoxy)-10,11-dihydrodibenzo[a,d]-cyclohepten-5-one
(24) 2-(2-aminoanilino)-7-(2-morpholin-4-yl-ethoxy)-10,11-dihydrodibenzo[a,d]-cyclohepten-5-one
(25) 2-(2,4-difluoroanilino)-7-(2-tetrahydropyran-4-yloxy)-10,11-dihydrodibenzo[a,d]-cyclohepten-5-one
(26) (S)-2-(2,4-difluorophenylamino)-8-(2,2-dimethyl-[1,3]dioxolan-4-ylmethoxy)-10,11-dihydrodibenzo[a,d]cyclohepten-5-one
(27) (R)-2-(2,4-difluorophenylamino)-8-(2,3-dihydroxypropoxy)-10,11-dihydrodibenzo[a,d]cyclohepten-5-one
(28) (S)-2-(2-aminophenylamino)-8-(2,2-dimethyl-[1,3]dioxolan-4-ylmethoxy)-10,11-dihydrodibenzo[a,d]cyclohepten-5-one
(29) (R)-2-(2-aminophenylamino)-8-(2,3-dihydroxypropoxy)-10,11-dihydrodibenzo[a,d]cyclohepten-5-one
(30) 2-(2,4-difluorophenylamino)-8-(2-morpholin-4-yl-ethoxy)-10,11-dihydrodibenzo[a,d]cyclohepten-5-one
(31) 8-(2,4-difluorophenylamino)-1-hydroxy-10,11-dihydrodibenzo[a,d]cyclohepten-5-one
(32) 8-(2,4-difluorophenylamino)-1-methoxy-10,11-dihydrodibenzo[a,d]cyclohepten-5-one
(33) 8-(2-aminophenylamino)-1-methoxy-10,11-dihydrodibenzo[a,d]cyclohepten-5-one
(34) (S)-8-(2,4-difluorophenylamino)-1-(2,2-dimethyl-[1,3]dioxolan-4-ylmethoxy)-10,11-dihydrodibenzo[a,d]cyclohepten-5-one
(35) (R)-8-(2,4-difluorophenylamino)-1-(2,3-dihydroxypropoxy)-10,11-dihydrodibenzo-[a,d]cyclohepten-5-one
(36) (S)-8-(2-aminophenylamino)-1-(2,2-dimethyl-[1,3]dioxolan-4-ylmethoxy)-10,11-dihydrodibenzo[a,d]cyclohepten-5-one
(37) (R)-8-(2-aminophenylamino)-1-(2,3-dihydroxypropoxy)-10,11-dihydrodibenzo-[a,d]cyclo-hepten-5-one
(38) 8-(2,4-difluorophenylamino)-1-(tetrahydropyran-4-yloxy)-10,11-dihydrodibenzo[a,d]cyclohepten-5-one
(39) 8-(2,4-difluorophenylamino)-1-(2-morpholin-4-yl-ethoxy)-10,11-dihydrodibenzo-[a,d]cyclo-hepten-5-one
(40) 3-(2,4-difluorophenylamino)-8-amino-6H-dibenzo[b,e]oxepin-11-one
(41) 3-(2-aminophenylamino)-8-amino-6H-dibenzo[b,e]oxepin-11-one
(42) 8-amino-3-(2-methoxyphenylamino)-6H-dibenzo[b,e]oxepin-11-one

(43) 8-amino-3-(4-fluoro-2-methoxyphenylamino)-6H-dibenzo[b,e]-oxepin-11-one
(44) 8-amino-3-(2-amino-4-trifluoromethylphenylamino)-6H-dibenzo[b,e]oxepin-11-one
(45) 8-amino-3-(tetrazol-1-yl)-6H-dibenzo[b,e]oxepin-11-one
(46) 3-(2,4-difluorophenylamino)-8-tetrazol-1-yl-6H-dibenzo[b,e]oxepin-11-one
(47) 2-(2-methyl-4-Fluoroanilino)-7-methoxydibenzosuberone
(48) 2-(2-chloroanilino)-7-methoxydibenzosuberone
(49) 2-(2-amino-4-fluoroanilino)-7-hydroxy-10,11-dihydrodibenzo[a,d]-cyclohepten-5-one
(50) 2-(2,4-difluoroanilino)-7-hydroxy-10,11-dihydrodibenzo[a,d]-cyclohepten-5-one
(51) 2-(2-chloro-4-fluoroanilino)-7-hydroxy-10,11-dihydrodibenzo[a,d]-cyclohepten-5-one
(52) 2-(2-chloroanilino)-7-hydroxy-10,11-dihydrodibenzo[a,d]-cyclohepten-5-one
(53) 2-(anilino)-7-hydroxy-10,11-dihydrodibenzo[a,d]-cyclohepten-5-one
(54) 2-(2,4-difluoroanilino)-7-hydroxy-dibenzo[a,d]-cyclohepten-5-one
(55) 2-(2,4-difluoroanilino)-7-[3-(4-Hydroxypiperidin-4-yl-propoxy)]-10,11-dihydrodibenzo[a,d]-cyclohepten-5-one
(56) 3-(2-amino-4-fluorophenylamino)-8-nitro-6H-dibenzo[b,e]oxepin-11-one and
(57) morpholine-4-carboxylic acid [3-(2,4-difluorophenylamino)-1-oxo-6,11-dihydrodibenzo[b,e]oxepin-8-yl] amide.

15. A pharmaceutical composition containing at least one compound of the formula I according to claim 1, optionally together with physiologically acceptable excipients.

* * * * *